United States Patent
Strings-Ufombah et al.

(10) Patent No.: US 11,499,141 B2
(45) Date of Patent: Nov. 15, 2022

(54) ADENO-ASSOCIATED VIRUS (AAV) WITH MODIFIED PHOSPHOLIPASE DOMAIN

(71) Applicant: Benitec Biopharma Limited, North Sydney (AU)

(72) Inventors: Vanessa Strings-Ufombah, North Sydney (AU); Shih-Chu Kao, North Sydney (AU); Petrus W. Roelvink, North Sydney (AU)

(73) Assignee: Benitec IP Holdings Inc., Wilmington, DE (US)

( * ) Notice: Subject to any disclaimer, the term of this patent is extended or adjusted under 35 U.S.C. 154(b) by 443 days.

(21) Appl. No.: 16/642,967

(22) PCT Filed: Aug. 30, 2018

(86) PCT No.: PCT/IB2018/056651
§ 371 (c)(1),
(2) Date: Feb. 28, 2020

(87) PCT Pub. No.: WO2019/043630
PCT Pub. Date: Mar. 7, 2019

(65) Prior Publication Data
US 2020/0190481 A1    Jun. 18, 2020

Related U.S. Application Data

(60) Provisional application No. 62/553,028, filed on Aug. 31, 2017.

(51) Int. Cl.
*C12N 15/86* (2006.01)
*A61K 48/00* (2006.01)
*C12N 7/00* (2006.01)
*A61K 39/12* (2006.01)
*C07K 14/005* (2006.01)

(52) U.S. Cl.
CPC .............. *C12N 7/00* (2013.01); *C07K 14/005* (2013.01); *C12N 15/86* (2013.01); *C12N 2710/14044* (2013.01); *C12N 2750/14122* (2013.01); *C12N 2750/14143* (2013.01); *C12N 2750/14152* (2013.01)

(58) Field of Classification Search
CPC .. A61K 2300/00; C07K 14/005; C12N 15/86; C12N 2750/14143; A61P 31/14
See application file for complete search history.

(56) References Cited

FOREIGN PATENT DOCUMENTS

| CN | 102071206 A | 5/2011 |
|---|---|---|
| WO | 2005/072364 A2 | 8/2005 |
| WO | 2009/137006 A2 | 11/2009 |
| WO | 2019/043630 A1 | 3/2019 |

OTHER PUBLICATIONS

Urabe et al., "Scalable Generation of High-Titer Recombinant Adeno-Associated Virus Type 5 in Insect Cells" Journal ov Virology, 2006, 80(4):1874-1885.*
International Search Report, Int'l Application No. PCT/IB2018/056651, dated Nov. 28, 2018, 5 pages.
Urabe et al., "Scalable Generation of High-Titer Recombinant Adeno-Associated Virus Type 5 in Insect Cells," Journal of Virology, Feb. 2006, vol. 80, No. 4, pp. 1874-1885.
Written Opinion of the International Searching Authority, Int'l Application No. PCT/IB2018/056651, dated Nov. 26, 2018, 5 pages.
Popa-Wagner, R., et al., "Impact of VP1-Specific Protein Sequence Motifs on Adeno-Associated Virus Type 2 Intracellular Trafficking and Nuclear Entry", Journal of Virology, vol. 86, No. 17, p. 9163-9174, Sep. 2012.

* cited by examiner

*Primary Examiner* — Barry A Chestnut
(74) *Attorney, Agent, or Firm* — Goodwin Procter LLP

(57) ABSTRACT

The present disclosure relates generally to modified adeno-associated virus (AAV) from serotypes other than serotype 2, which have a viral capsid protein with a subunit 1 (VP1) sequence which is modified relative to the corresponding wildtype sequence. In particular, the modified AAVs of the disclosure comprise site-specific amino acid substitutions within the phospholipase A2 (PLA2) domain and flanking sequence relative to the corresponding wild-type sequence which improve functionality of the AAV when produced in insect cells. The present disclosure also relates to methods of producing the modified AAVs, reagents therefor, baculovirus expression systems and insect cells for producing said modified AAVs.

20 Claims, 11 Drawing Sheets
Specification includes a Sequence Listing.

SEQUENCE LISTING

<160> NUMBER OF SEQ ID NOS: 39

<210> SEQ ID NO 1
<211> LENGTH: 64
<212> TYPE: PRT
<213> ORGANISM: Artificial sequence
<220> FEATURE:
<223> OTHER INFORMATION: Modified consensus VP1 subsequence for AAV

```
                             serotypes
<220> FEATURE:
<221> NAME/KEY: MISC_FEATURE
<222> LOCATION: (15)..(15)
<223> OTHER INFORMATION: Xaa is Gly or Phe
<220> FEATURE:
<221> NAME/KEY: MISC_FEATURE
<222> LOCATION: (20)..(20)
<223> OTHER INFORMATION: Xaa is Arg or Lys
<220> FEATURE:
<221> NAME/KEY: MISC_FEATURE
<222> LOCATION: (29)..(29)
<223> OTHER INFORMATION: Xaa is Glu or Ala
<220> FEATURE:
<221> NAME/KEY: MISC_FEATURE
<222> LOCATION: (30)..(30)
<223> OTHER INFORMATION: Xaa is Val or Ala
<220> FEATURE:
<221> NAME/KEY: MISC_FEATURE
<222> LOCATION: (32)..(32)
<223> OTHER INFORMATION: Xaa is Arg or Leu
<220> FEATURE:
<221> NAME/KEY: MISC_FEATURE
<222> LOCATION: (36)..(36)
<223> OTHER INFORMATION: Xaa is Ile or Lys
<220> FEATURE:
<221> NAME/KEY: MISC_FEATURE
<222> LOCATION: (37)..(37)
<223> OTHER INFORMATION: Xaa is Ser or Ala
<220> FEATURE:
<221> NAME/KEY: MISC_FEATURE
<222> LOCATION: (39)..(39)
<223> OTHER INFORMATION: Xaa is Asn or Asp
<220> FEATURE:
<221> NAME/KEY: MISC_FEATURE
<222> LOCATION: (51)..(51)
<223> OTHER INFORMATION: Xaa is Lys or Arg
<220> FEATURE:
<221> NAME/KEY: MISC_FEATURE
<222> LOCATION: (61)..(61)
<223> OTHER INFORMATION: Xaa is Glu or Gln
<220> FEATURE:
<221> NAME/KEY: MISC_FEATURE
<222> LOCATION: (62)..(62)
<223> OTHER INFORMATION: Xaa is Lys or Arg

<400> SEQUENCE: 1

Ser Arg Gly Leu Val Leu Pro Gly Tyr Asn Tyr Leu Gly Pro Xaa Asn
1               5                   10                  15

Gly Leu Asp Xaa Gly Glu Pro Val Asn Glu Ala Asp Xaa Xaa Ala Xaa
            20                  25                  30

Glu His Asp Xaa Xaa Tyr Xaa Arg Gln Leu Asp Ser Gly Asp Asn Pro
        35                  40                  45

Tyr Leu Xaa Tyr Asn His Ala Asp Ala Glu Phe Gln Xaa Xaa Leu Lys
    50                  55                  60

<210> SEQ ID NO 2
<211> LENGTH: 64
<212> TYPE: PRT
<213> ORGANISM: Adeno-associated virus

<400> SEQUENCE: 2

Ala Arg Gly Leu Val Leu Pro Gly Tyr Asn Tyr Leu Gly Pro Gly Asn
1               5                   10                  15

Gly Leu Asp Arg Gly Glu Pro Val Asn Arg Ala Asp Glu Val Ala Arg
            20                  25                  30

Glu His Asp Ile Ser Tyr Asn Glu Gln Leu Glu Ala Gly Asp Asn Pro
        35                  40                  45

Tyr Leu Lys Tyr Asn His Ala Asp Ala Glu Phe Gln Glu Lys Leu Ala
    50                  55                  60
```

<210> SEQ ID NO 3
<211> LENGTH: 64
<212> TYPE: PRT
<213> ORGANISM: Adeno-associated virus

<400> SEQUENCE: 3

Ser Arg Gly Leu Val Leu Pro Gly Tyr Lys Tyr Leu Gly Pro Phe Asn
1               5                   10                  15

Gly Leu Asp Lys Gly Glu Pro Val Asn Glu Ala Asp Ala Ala Ala Leu
            20                  25                  30

Glu His Asp Lys Ala Tyr Asp Arg Gln Leu Asp Ser Gly Asp Asn Pro
        35                  40                  45

Tyr Leu Lys Tyr Asn His Ala Asp Ala Glu Phe Gln Glu Arg Leu Lys
    50                  55                  60

<210> SEQ ID NO 4
<211> LENGTH: 64
<212> TYPE: PRT
<213> ORGANISM: Adeno-associated virus

<400> SEQUENCE: 4

Arg Arg Gly Leu Val Leu Pro Gly Tyr Lys Tyr Leu Gly Pro Gly Asn
1               5                   10                  15

Gly Leu Asp Lys Gly Glu Pro Val Asn Glu Ala Asp Ala Ala Ala Leu
            20                  25                  30

Glu His Asp Lys Ala Tyr Asp Gln Gln Leu Lys Ala Gly Asp Asn Pro
        35                  40                  45

Tyr Leu Lys Tyr Asn His Ala Asp Ala Glu Phe Gln Glu Arg Leu Gln
    50                  55                  60

<210> SEQ ID NO 5
<211> LENGTH: 64
<212> TYPE: PRT
<213> ORGANISM: Adeno-associated virus

<400> SEQUENCE: 5

Ala Arg Gly Leu Val Leu Pro Gly Tyr Lys Tyr Leu Gly Pro Gly Asn
1               5                   10                  15

Gly Leu Asp Lys Gly Glu Pro Val Asn Ala Ala Asp Ala Ala Ala Leu
            20                  25                  30

Glu His Asp Lys Ala Tyr Asp Gln Gln Leu Lys Ala Gly Asp Asn Pro
        35                  40                  45

Tyr Leu Lys Tyr Asn His Ala Asp Ala Glu Phe Gln Gln Arg Leu Gln
    50                  55                  60

<210> SEQ ID NO 6
<211> LENGTH: 64
<212> TYPE: PRT
<213> ORGANISM: Adeno-associated virus

<400> SEQUENCE: 6

Ala Arg Gly Leu Val Leu Pro Gly Tyr Asn Tyr Leu Gly Pro Gly Asn
1               5                   10                  15

Gly Leu Asp Arg Gly Glu Pro Val Asn Arg Ala Asp Glu Val Ala Arg
            20                  25                  30

Glu His Asp Ile Ser Tyr Asn Glu Gln Leu Glu Ala Gly Asp Asn Pro
        35                  40                  45

Tyr Leu Lys Tyr Asn His Ala Asp Ala Glu Phe Gln Glu Lys Leu Ala

<210> SEQ ID NO 7
<211> LENGTH: 64
<212> TYPE: PRT
<213> ORGANISM: Adeno-associated virus

<400> SEQUENCE: 7

Gly Arg Gly Leu Val Leu Pro Gly Tyr Lys Tyr Leu Gly Pro Phe Asn
1               5                   10                  15

Gly Leu Asp Lys Gly Glu Pro Val Asn Ala Ala Asp Ala Ala Ala Leu
            20                  25                  30

Glu His Asp Lys Ala Tyr Asp Gln Gln Leu Lys Ala Gly Asp Asn Pro
        35                  40                  45

Tyr Leu Arg Tyr Asn His Ala Asp Ala Glu Phe Gln Glu Arg Leu Gln
    50                  55                  60

<210> SEQ ID NO 8
<211> LENGTH: 64
<212> TYPE: PRT
<213> ORGANISM: Adeno-associated virus

<400> SEQUENCE: 8

Gly Arg Gly Leu Val Leu Pro Gly Tyr Lys Tyr Leu Gly Pro Phe Asn
1               5                   10                  15

Gly Leu Asp Lys Gly Glu Pro Val Asn Ala Ala Asp Ala Ala Ala Leu
            20                  25                  30

Glu His Asp Lys Ala Tyr Asp Gln Gln Leu Lys Ala Gly Asp Asn Pro
        35                  40                  45

Tyr Leu Arg Tyr Asn His Ala Asp Ala Glu Phe Gln Glu Arg Leu Gln
    50                  55                  60

<210> SEQ ID NO 9
<211> LENGTH: 64
<212> TYPE: PRT
<213> ORGANISM: Adeno-associated virus

<400> SEQUENCE: 9

Gly Arg Gly Leu Val Leu Pro Gly Tyr Lys Tyr Leu Gly Pro Phe Asn
1               5                   10                  15

Gly Leu Asp Lys Gly Glu Pro Val Asn Ala Ala Asp Ala Ala Ala Leu
            20                  25                  30

Glu His Asp Lys Ala Tyr Asp Gln Gln Leu Gln Ala Gly Asp Asn Pro
        35                  40                  45

Tyr Leu Arg Tyr Asn His Ala Asp Ala Glu Phe Gln Glu Arg Leu Gln
    50                  55                  60

<210> SEQ ID NO 10
<211> LENGTH: 64
<212> TYPE: PRT
<213> ORGANISM: Adeno-associated virus

<400> SEQUENCE: 10

Ala Arg Gly Leu Val Leu Pro Gly Tyr Lys Tyr Leu Gly Pro Gly Asn
1               5                   10                  15

Gly Leu Asp Lys Gly Glu Pro Val Asn Ala Ala Asp Ala Ala Ala Leu
            20                  25                  30

Glu His Asp Lys Ala Tyr Asp Gln Gln Leu Lys Ala Gly Asp Asn Pro
        35                  40                  45

-continued

Tyr Leu Lys Tyr Asn His Ala Asp Ala Glu Phe Gln Glu Arg Leu Lys
    50                  55                  60

<210> SEQ ID NO 11
<211> LENGTH: 64
<212> TYPE: PRT
<213> ORGANISM: Adeno-associated virus

<400> SEQUENCE: 11

Gly Arg Gly Leu Val Leu Pro Gly Tyr Lys Tyr Leu Gly Pro Phe Asn
1               5                   10                  15

Gly Leu Asp Lys Gly Glu Pro Val Asn Ala Ala Asp Ala Ala Ala Leu
                20                  25                  30

Glu His Asp Lys Ala Tyr Asp Gln Gln Leu Lys Ala Gly Asp Asn Pro
            35                  40                  45

Tyr Leu Arg Tyr Asn His Ala Asp Ala Glu Phe Gln Glu Arg Leu Gln
    50                  55                  60

<210> SEQ ID NO 12
<211> LENGTH: 64
<212> TYPE: PRT
<213> ORGANISM: Adeno-associated virus

<400> SEQUENCE: 12

Gly Arg Gly Leu Val Leu Pro Gly Tyr Lys Tyr Leu Gly Pro Phe Asn
1               5                   10                  15

Gly Leu Asp Lys Gly Glu Pro Val Asn Ala Ala Asp Ala Ala Ala Leu
                20                  25                  30

Glu His Asp Lys Ala Tyr Asp Gln Gln Leu Lys Ala Gly Asp Asn Pro
            35                  40                  45

Tyr Leu Arg Tyr Asn His Ala Asp Ala Glu Phe Gln Glu Arg Leu Gln
    50                  55                  60

<210> SEQ ID NO 13
<211> LENGTH: 64
<212> TYPE: PRT
<213> ORGANISM: Adeno-associated virus

<400> SEQUENCE: 13

Gly Arg Gly Leu Val Leu Pro Gly Tyr Lys Tyr Leu Gly Pro Phe Asn
1               5                   10                  15

Gly Leu Asp Lys Gly Glu Pro Val Asn Glu Ala Asp Ala Ala Ala Leu
                20                  25                  30

Glu His Asp Lys Ala Tyr Asp Lys Gln Leu Glu Gln Gly Asp Asn Pro
            35                  40                  45

Tyr Leu Lys Tyr Asn His Ala Asp Ala Glu Phe Gln Gln Arg Leu Ala
    50                  55                  60

<210> SEQ ID NO 14
<211> LENGTH: 64
<212> TYPE: PRT
<213> ORGANISM: Adeno-associated virus

<400> SEQUENCE: 14

Gly Arg Gly Leu Val Leu Pro Gly Tyr Lys Tyr Leu Gly Pro Phe Asn
1               5                   10                  15

Gly Leu Asp Lys Gly Glu Pro Val Asn Ala Ala Asp Ala Ala Ala Leu
                20                  25                  30

Glu His Asp Lys Ala Tyr Asp Gln Gln Leu Lys Ala Gly Asp Asn Pro
            35                  40                  45

Tyr Leu Arg Tyr Asn His Ala Asp Ala Glu Phe Gln Glu Arg Leu Gln
        50                  55                  60

<210> SEQ ID NO 15
<211> LENGTH: 64
<212> TYPE: PRT
<213> ORGANISM: Artificial sequence
<220> FEATURE:
<223> OTHER INFORMATION: Modified VP1 subsequence for AAV serotype 1

<400> SEQUENCE: 15

Ser Arg Gly Leu Val Leu Pro Gly Tyr Asn Tyr Leu Gly Pro Gly Asn
1               5                   10                  15

Gly Leu Asp Arg Gly Glu Pro Val Asn Glu Ala Asp Glu Val Ala Arg
            20                  25                  30

Glu His Asp Ile Ser Tyr Asn Arg Gln Leu Asp Ser Gly Asp Asn Pro
        35                  40                  45

Tyr Leu Lys Tyr Asn His Ala Asp Ala Glu Phe Gln Glu Lys Leu Lys
        50                  55                  60

<210> SEQ ID NO 16
<211> LENGTH: 64
<212> TYPE: PRT
<213> ORGANISM: Artificial sequence
<220> FEATURE:
<223> OTHER INFORMATION: Modified VP1 subsequence for AAV serotype 3

<400> SEQUENCE: 16

Ser Arg Gly Leu Val Leu Pro Gly Tyr Lys Tyr Leu Gly Pro Gly Asn
1               5                   10                  15

Gly Leu Asp Lys Gly Glu Pro Val Asn Glu Ala Asp Ala Ala Ala Leu
            20                  25                  30

Glu His Asp Lys Ala Tyr Asp Arg Gln Leu Asp Ser Gly Asp Asn Pro
        35                  40                  45

Tyr Leu Lys Tyr Asn His Ala Asp Ala Glu Phe Gln Glu Arg Leu Lys
        50                  55                  60

<210> SEQ ID NO 17
<211> LENGTH: 64
<212> TYPE: PRT
<213> ORGANISM: Artificial sequence
<220> FEATURE:
<223> OTHER INFORMATION: Modified VP1 subsequence for AAV serotype 4

<400> SEQUENCE: 17

Ser Arg Gly Leu Val Leu Pro Gly Tyr Lys Tyr Leu Gly Pro Gly Asn
1               5                   10                  15

Gly Leu Asp Lys Gly Glu Pro Val Asn Glu Ala Asp Ala Ala Ala Leu
            20                  25                  30

Glu His Asp Lys Ala Tyr Asp Arg Gln Leu Asp Ser Gly Asp Asn Pro
        35                  40                  45

Tyr Leu Lys Tyr Asn His Ala Asp Ala Glu Phe Gln Gln Arg Leu Lys
        50                  55                  60

<210> SEQ ID NO 18
<211> LENGTH: 64
<212> TYPE: PRT
<213> ORGANISM: Artificial sequence
<220> FEATURE:
<223> OTHER INFORMATION: Modified VP1 subsequence for AAV serotype 5

<400> SEQUENCE: 18

```
Ser Arg Gly Leu Val Leu Pro Gly Tyr Asn Tyr Leu Gly Pro Gly Asn
1               5                   10                  15

Gly Leu Asp Arg Gly Glu Pro Val Asn Glu Ala Asp Glu Val Ala Arg
                20                  25                  30

Glu His Asp Ile Ser Tyr Asn Arg Gln Leu Asp Ser Gly Asp Asn Pro
                35                  40                  45

Tyr Leu Lys Tyr Asn His Ala Asp Ala Glu Phe Gln Glu Lys Leu Lys
        50                  55                  60
```

<210> SEQ ID NO 19
<211> LENGTH: 64
<212> TYPE: PRT
<213> ORGANISM: Artificial sequence
<220> FEATURE:
<223> OTHER INFORMATION: Modified VP1 subsequence for AAV serotype 6

<400> SEQUENCE: 19

```
Ser Arg Gly Leu Val Leu Pro Gly Tyr Lys Tyr Leu Gly Pro Phe Asn
1               5                   10                  15

Gly Leu Asp Lys Gly Glu Pro Val Asn Glu Ala Asp Ala Ala Ala Leu
                20                  25                  30

Glu His Asp Lys Ala Tyr Asp Arg Gln Leu Asp Ser Gly Asp Asn Pro
                35                  40                  45

Tyr Leu Arg Tyr Asn His Ala Asp Ala Glu Phe Gln Glu Arg Leu Lys
        50                  55                  60
```

<210> SEQ ID NO 20
<211> LENGTH: 64
<212> TYPE: PRT
<213> ORGANISM: Artificial sequence
<220> FEATURE:
<223> OTHER INFORMATION: Modified VP1 subsequence for AAV serotype 7

<400> SEQUENCE: 20

```
Ser Arg Gly Leu Val Leu Pro Gly Tyr Lys Tyr Leu Gly Pro Phe Asn
1               5                   10                  15

Gly Leu Asp Lys Gly Glu Pro Val Asn Gl

<210> SEQ ID NO 22
<211> LENGTH: 64
<212> TYPE: PRT
<213> ORGANISM: Artificial sequence
<220> FEATURE:
<223> OTHER INFORMATION: Modified VP1 subsequence for AAV serotype 9

<400> SEQUENCE: 22

Ser Arg Gly Leu Val Leu Pro Gly Tyr Lys Tyr Leu Gly Pro Gly Asn
1

```
Gly Leu Asp Lys Gly Glu Pro Val Asn Glu Ala Asp Ala Ala Ala Leu
            20                  25                  30

Glu His Asp Lys Ala Tyr Asp Arg Gln Leu Asp Ser Gly Asp Asn Pro
            35                  40                  45

Tyr Leu Lys Tyr Asn His Ala Asp Ala Glu Phe Gln Gln Arg Leu Lys
    50                  55                  60

<210> SEQ ID NO 26
<211> LENGTH: 64
<212> TYPE: PRT
<213> ORGANISM: Artificial sequence
<220> FEATURE:
<223> OTHER INFORMATION: Modified VP1 subsequence for AAV serotype 13

<400> SEQUENCE: 26

Ser Arg Gly Leu Val Leu Pro Gly Tyr Lys Tyr Leu Gly Pro Phe Asn
1

```
                210                 215                 220
Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
            245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
        275                 280                 285

Arg Leu Ile Asn Asn Tyr Trp Gly Phe Arg Pro Arg Ser Leu Arg Val
        290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
            325                 330                 335

Asp Asp Tyr Gln Leu Pro Tyr Val Val Gly Asn Gly Thr Glu Gly Cys
            340                 345                 350

Leu Pro Ala Phe Pro Pro Gln Val Phe Thr Leu Pro Gln Tyr Gly Tyr
        355                 360                 365

Ala Thr Leu Asn Arg Asp Asn Gly Asp Asn Pro Thr Glu Arg Ser Ser
        370                 375                 380

Phe Phe Cys Leu Glu Tyr Phe Pro Ser Lys Met Leu Arg Thr Gly Asn
385                 390                 395                 400

Asn Phe Glu Phe Thr Tyr Ser Phe Glu Glu Val Pro Phe His Cys Ser
            405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Ser Ala Thr Gly Ala Ile Gln
        435                 440                 445

Phe Gln Lys Asn Leu Ala Gly Arg Tyr Ala Asn Thr Tyr Lys Asn Trp
        450                 455                 460

Phe Pro Gly Pro Met Gly Arg Thr Gln Gly Trp Asn Thr Ser Ser Gly
465                 470                 475                 480

Ser Ser Thr Asn Arg Val Ser Val Asn Asn Phe Ser Val Ser Asn Arg
            485                 490                 495

Met Asn Leu Glu Gly Ala Ser Tyr Gln Val Asn Pro Gln Pro Asn Gly
            500                 505                 510

Met Thr Asn Thr Leu Gln Gly Ser Asn Arg Tyr Ala Leu Glu Asn Thr
        515                 520                 525

Met Ile Phe Asn Ala Gln Asn Ala Thr Pro Gly Thr Thr Ser Val Tyr
        530                 535                 540

Pro Glu Asp Asn Leu Leu Thr Ser Glu Ser Glu Thr Gln Pro Val
545                 550                 555                 560

Asn Arg Val Ala Tyr Asn Thr Gly Gly Gln Met Ala Thr Asn Ala Gln
            565                 570                 575

Asn Ala Thr Thr Ala Pro Thr Val Gly Thr Tyr Asn Leu Gln Glu Val
            580                 585                 590

Leu Pro Gly Ser Val Trp Met Glu Arg Asp Val Tyr Leu Gln Gly Pro
        595                 600                 605

Ile Trp Ala Lys Ile Pro Glu Thr Gly Ala His Phe His Pro Ser Pro
        610                 615                 620

Ala Met Gly Gly Phe Gly Leu Lys His Pro Pro Met Met Leu Ile
625                 630                 635                 640
```

```
Lys Asn Thr Pro Val Pro Gly Asn Ile Thr Ser Phe Ser Asp Val Pro
                645                 650                 655

Val Ser Ser Phe Ile Thr Gln Tyr Ser Thr Gly Gln Val Thr Val Glu
            660                 665                 670

Met Glu Trp Glu Leu Lys Lys Glu Asn Ser Lys Arg Trp Asn Pro Glu
        675                 680                 685

Ile Gln Tyr Thr Asn Asn Tyr Asn Asp Pro Gln Phe Val Asp Phe Ala
    690                 695                 700

Pro Asp Gly Ser Gly Glu Tyr Arg Thr Thr Arg Ala Ile Gly Thr Arg
705                 710                 715                 720

Tyr Leu Thr Arg Pro Leu
                725

<210> SEQ ID NO 28
<211> LENGTH: 735
<212> TYPE: PRT
<213> ORGANISM: Adeno-associated virus

<400> SEQUENCE: 28

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
```

```
                    275                 280                 285
Cys His Phe Ser Pro Arg Asp Trp Gln Arg Leu Ile Asn Asn Asn Trp
        290                 295                 300
Gly Phe Arg Pro Lys Arg Leu Asn Phe Lys Leu Phe Asn Ile Gln Val
305                 310                 315                 320
Lys Glu Val Thr Gln Asn Asp Gly Thr Thr Thr Ile Ala Asn Asn Leu
                325                 330                 335
Thr Ser Thr Val Gln Val Phe Thr Asp Ser Glu Tyr Gln Leu Pro Tyr
                340                 345                 350
Val Leu Gly Ser Ala His Gln Gly Cys Leu Pro Pro Phe Pro Ala Asp
                355                 360                 365
Val Phe Met Val Pro Gln Tyr Gly Tyr Leu Thr Leu Asn Asn Gly Ser
        370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Thr Phe Ser Tyr Thr Phe Glu
                405                 410                 415
Asp Val Pro Phe His Ser Ser Tyr Ala His Ser Gln Ser Leu Asp Arg
                420                 425                 430
Leu Met Asn Pro Leu Ile Asp Gln Tyr Leu Tyr Tyr Leu Ser Arg Thr
        435                 440                 445
Asn Thr Pro Ser Gly Thr Thr Thr Gln Ser Arg Leu Gln Phe Ser Gln
        450                 455                 460
Ala Gly Ala Ser Asp Ile Arg Asp Gln Ser Arg Asn Trp Leu Pro Gly
465                 470                 475                 480
Pro Cys Tyr Arg Gln Gln Arg Val Ser Lys Thr Ser Ala Asp Asn Asn
                485                 490                 495
Asn Ser Glu Tyr Ser Trp Thr Gly Ala Thr Lys Tyr His Leu Asn Gly
                500                 505                 510
Arg Asp Ser Leu Val Asn Pro Gly Pro Ala Met Ala Ser His Lys Asp
        515                 520                 525
Asp Glu Glu Lys Phe Phe Pro Gln Ser Gly Val Leu Ile Phe Gly Lys
        530                 535                 540
Gln Gly Ser Glu Lys Thr Asn Val Asp Ile Glu Lys Val Met Ile Thr
545                 550                 555                 560
Asp Glu Glu Glu Ile Arg Thr Thr Asn Pro Val Ala Thr Glu Gln Tyr
                565                 570                 575
Gly Ser Val Ser Thr Asn Leu Gln Arg Gly Asn Arg Gln Ala Ala Thr
                580                 585                 590
Ala Asp Val Asn Thr Gln Gly Val Leu Pro Gly Met Val Trp Gln Asp
        595                 600                 605
Arg Asp Val Tyr Leu Gln Gly Pro Ile Trp Ala Lys Ile Pro His Thr
        610                 615                 620
Asp Gly His Phe His Pro Ser Pro Leu Met Gly Gly Phe Gly Leu Lys
625                 630                 635                 640
His Pro Pro Pro Gln Ile Leu Ile Lys Asn Thr Pro Val Pro Ala Asn
                645                 650                 655
Pro Ser Thr Thr Phe Ser Ala Ala Lys Phe Ala Ser Phe Ile Thr Gln
                660                 665                 670
Tyr Ser Thr Gly Gln Val Ser Val Glu Ile Glu Trp Glu Leu Gln Lys
        675                 680                 685
Glu Asn Ser Lys Arg Trp Asn Pro Glu Ile Gln Tyr Thr Ser Asn Tyr
        690                 695                 700
```

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 29
<211> LENGTH: 736
<212> TYPE: PRT
<213> ORGANISM: Adeno-associated virus

<400> SEQUENCE: 29

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
            20                  25                  30

Lys Ala Asn Gln Gln His Gln Asp Asn Arg Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Ala Lys Thr Ala Pro Gly Lys Lys Arg
    130                 135                 140

Pro Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Lys Leu Ser Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr

```
                  340                 345                 350
Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
        370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Asn Arg Thr
        435                 440                 445

Gln Gly Thr Thr Ser Gly Thr Thr Asn Gln Ser Arg Leu Leu Phe Ser
    450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
            500                 505                 510

Gly Arg Asp Ser Leu Val Asn Pro Gly Pro Ala Met Ala Ser His Lys
        515                 520                 525

Asp Asp Glu Glu Lys Phe Phe Pro Met His Gly Asn Leu Ile Phe Gly
    530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
            580                 585                 590

Thr Arg Thr Val Asn Asp Gln Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Met Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Asn Leu
                725                 730                 735

<210> SEQ ID NO 30
<211> LENGTH: 734
<212> TYPE: PRT
<213> ORGANISM: Adeno-associated virus
```

<400> SEQUENCE: 30

```
Met Thr Asp Gly Tyr Leu Pro Asp Trp Leu Glu Asp Asn Leu Ser Glu
1               5                   10                  15

Gly Val Arg Glu Trp Ala Leu Gln Pro Gly Ala Pro Lys Pro Lys
            20                  25                  30

Ala Asn Gln Gln His Gln Asp Asn Ala Arg Gly Leu Val Leu Pro Gly
            35                  40                  45

Tyr Lys Tyr Leu Gly Pro Gly Asn Gly Leu Asp Lys Gly Glu Pro Val
        50                  55                  60

Asn Ala Ala Asp Ala Ala Ala Leu Glu His Asp Lys Ala Tyr Asp Gln
65                  70                  75                  80

Gln Leu Lys Ala Gly Asp Asn Pro Tyr Leu Lys Tyr Asn His Ala Asp
                85                  90                  95

Ala Glu Phe Gln Gln Arg Leu Gln Gly Asp Thr Ser Phe Gly Gly Asn
            100                 105                 110

Leu Gly Arg Ala Val Phe Gln Ala Lys Lys Arg Val Leu Glu Pro Leu
        115                 120                 125

Gly Leu Val Glu Gln Ala Gly Glu Thr Ala Pro Gly Lys Lys Arg Pro
130                 135                 140

Leu Ile Glu Ser Pro Gln Gln Pro Asp Ser Ser Thr Gly Ile Gly Lys
145                 150                 155                 160

Lys Gly Lys Gln Pro Ala Lys Lys Lys Leu Val Phe Glu Asp Glu Thr
                165                 170                 175

Gly Ala Gly Asp Gly Pro Pro Glu Gly Ser Thr Ser Gly Ala Met Ser
            180                 185                 190

Asp Asp Ser Glu Met Arg Ala Ala Gly Gly Ala Ala Val Glu Gly
        195                 200                 205

Gly Gln Gly Ala Asp Gly Val Gly Asn Ala Ser Gly Asp Trp His Cys
210                 215                 220

Asp Ser Thr Trp Ser Glu Gly His Val Thr Thr Thr Ser Thr Arg Thr
225                 230                 235                 240

Trp Val Leu Pro Thr Tyr Asn Asn His Leu Tyr Lys Arg Leu Gly Glu
                245                 250                 255

Ser Leu Gln Ser Asn Thr Tyr Asn Gly Phe Ser Thr Pro Trp Gly Tyr
            260                 265                 270

Phe Asp Phe Asn Arg Phe His Cys His Phe Ser Pro Arg Asp Trp Gln
        275                 280                 285

Arg Leu Ile Asn Asn Asn Trp Gly Met Arg Pro Lys Ala Met Arg Val
290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
            340                 345                 350

Leu Pro Pro Phe Pro Asn Asp Val Phe Met Val Pro Gln Tyr Gly Tyr
        355                 360                 365

Cys Gly Leu Val Thr Gly Asn Thr Ser Gln Gln Thr Asp Arg Asn
                370                 375                 380

Ala Phe Tyr Cys Leu Glu Tyr Phe Pro Ser Gln Met Leu Arg Thr Gly
385                 390                 395                 400

Asn Asn Phe Glu Ile Thr Tyr Ser Phe Glu Lys Val Pro Phe His Ser
```

```
                405                 410                 415
Met Tyr Ala His Ser Gln Ser Leu Asp Arg Leu Met Asn Pro Leu Ile
            420                 425                 430

Asp Gln Tyr Leu Trp Gly Leu Gln Ser Thr Thr Thr Gly Thr Thr Leu
        435                 440                 445

Asn Ala Gly Thr Ala Thr Asn Phe Thr Lys Leu Arg Pro Thr Asn
    450                 455                 460

Phe Ser Asn Phe Lys Lys Asn Trp Leu Pro Gly Pro Ser Ile Lys Gln
465                 470                 475                 480

Gln Gly Phe Ser Lys Thr Ala Asn Gln Asn Tyr Lys Ile Pro Ala Thr
                485                 490                 495

Gly Ser Asp Ser Leu Ile Lys Tyr Glu Thr His Ser Thr Leu Asp Gly
            500                 505                 510

Arg Trp Ser Ala Leu Thr Pro Gly Pro Pro Met Ala Thr Ala Gly Pro
        515                 520                 525

Ala Asp Ser Lys Phe Ser Asn Ser Gln Leu Ile Phe Ala Gly Pro Lys
    530                 535                 540

Gln Asn Gly Asn Thr Ala Thr Val Pro Gly Thr Leu Ile Phe Thr Ser
545                 550                 555                 560

Glu Glu Glu Leu Ala Ala Thr Asn Ala Thr Asp Thr Asp Met Trp Gly
                565                 570                 575

Asn Leu Pro Gly Gly Asp Gln Ser Asn Ser Asn Leu Pro Thr Val Asp
            580                 585                 590

Arg Leu Thr Ala Leu Gly Ala Val Pro Gly Met Val Trp Gln Asn Arg
        595                 600                 605

Asp Ile Tyr Tyr Gln Gly Pro Ile Trp Ala Lys Ile Pro His Thr Asp
    610                 615                 620

Gly His Phe His Pro Ser Pro Leu Ile Gly Gly Phe Gly Leu Lys His
625                 630                 635                 640

Pro Pro Pro Gln Ile Phe Ile Lys Asn Thr Pro Val Pro Ala Asn Pro
                645                 650                 655

Ala Thr Thr Phe Ser Ser Thr Pro Val Asn Ser Phe Ile Thr Gln Tyr
            660                 665                 670

Ser Thr Gly Gln Val Ser Val Gln Ile Asp Trp Glu Ile Gln Lys Glu
        675                 680                 685

Arg Ser Lys Arg Trp Asn Pro Glu Val Gln Phe Thr Ser Asn Tyr Gly
    690                 695                 700

Gln Gln Asn Ser Leu Leu Trp Ala Pro Asp Ala Ala Gly Lys Tyr Thr
705                 710                 715                 720

Glu Pro Arg Ala Ile Gly Thr Arg Tyr Leu Thr His His Leu
                725                 730

<210> SEQ ID NO 31
<211> LENGTH: 724
<212> TYPE: PRT
<213> ORGANISM: Adeno-associated virus

<400> SEQUENCE: 31

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
                20                  25                  30

Pro Asn Gln Gln His Gln Asp Gln Ala Arg Gly Leu Val Leu Pro Gly
            35                  40                  45
```

```
Tyr Asn Tyr Leu Gly Pro Gly Asn Gly Leu Asp Arg Gly Glu Pro Val
 50                  55                  60

Asn Arg Ala Asp Glu Val Ala Arg Glu His Asp Ile Ser Tyr Asn Glu
 65                  70                  75                  80

Gln Leu Glu Ala Gly Asp Asn Pro Tyr Leu Lys Tyr Asn His Ala Asp
                 85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
    210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
        275                 280                 285

Arg Leu Ile Asn Asn Tyr Trp Gly Phe Arg Pro Arg Ser Leu Arg Val
    290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
            340                 345                 350

Leu Pro Ala Phe Pro Pro Gln Val Phe Thr Leu Pro Gln Tyr Gly Tyr
        355                 360                 365

Ala Thr Leu Asn Arg Asp Asn Thr Glu Asn Pro Thr Glu Arg Ser Ser
    370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Asn Asn Thr Gly Gly Val Gln
        435                 440                 445

Phe Asn Lys Asn Leu Ala Gly Arg Tyr Ala Asn Thr Tyr Lys Asn Trp
450                 455                 460

Phe Pro Gly Pro Met Gly Arg Thr Gln Gly Trp Asn Leu Gly Ser Gly
```

```
            465                 470                 475                 480
        Val Asn Arg Ala Ser Val Ser Ala Phe Ala Thr Thr Asn Arg Met Glu
                            485                 490                 495

Leu Glu Gly Ala Ser Tyr Gln Val Pro Pro Gln Pro Asn Gly Met Thr
                            500                 505                 510

Asn Asn Leu Gln Gly Ser Asn Thr Tyr Ala Leu Glu Asn Thr Met Ile
                            515                 520                 525

Phe Asn Ser Gln Pro Ala Asn Pro Gly Thr Thr Ala Thr Tyr Leu Glu
                            530                 535                 540

Gly Asn Met Leu Ile Thr Ser Glu Ser Glu Thr Gln Pro Val Asn Arg
        545                 550                 555                 560

Val Ala Tyr Asn Val Gly Gly Gln Met Ala Thr Asn Asn Gln Ser Ser
                            565                 570                 575

Thr Thr Ala Pro Ala Thr Gly Thr Tyr Asn Leu Gln Glu Ile Val Pro
                            580                 585                 590

Gly Ser Val Trp Met Glu Arg Asp Val Tyr Leu Gln Gly Pro Ile Trp
                            595                 600                 605

Ala Lys Ile Pro Glu Thr Gly Ala His Phe His Pro Ser Pro Ala Met
                            610                 615                 620

Gly Gly Phe Gly Leu Lys His Pro Pro Pro Met Met Leu Ile Lys Asn
        625                 630                 635                 640

Thr Pro Val Pro Gly Asn Ile Thr Ser Phe Ser Asp Val Pro Val Ser
                            645                 650                 655

Ser Phe Ile Thr Gln Tyr Ser Thr Gly Gln Val Thr Val Glu Met Glu
                            660                 665                 670

Trp Glu Leu Lys Lys Glu Asn Ser Lys Arg Trp Asn Pro Glu Ile Gln
                            675                 680                 685

Tyr Thr Asn Asn Tyr Asn Asp Pro Gln Phe Val Asp Phe Ala Pro Asp
                            690                 695                 700

Ser Thr Gly Glu Tyr Arg Thr Thr Arg Pro Ile Gly Thr Arg Tyr Leu
        705                 710                 715                 720

Thr Arg Pro Leu

<210> SEQ ID NO 32
<211> LENGTH: 736
<212> TYPE: PRT
<213> ORGANISM: Adeno-associated virus

<400> SEQUENCE: 32

Met Ala Ala Asp Gly Tyr Leu Pro Asp Trp Leu Glu Asp Asn Leu Ser
        1               5                   10                  15

Glu Gly Ile Arg Glu Trp Trp Asp Leu Lys Pro Gly Ala Pro Lys Pro
                            20                  25                  30

Lys Ala Asn Gln Gln Lys Gln Asp Asp Gly Arg Gly Leu Val Leu Pro
                            35                  40                  45

Gly Tyr Lys Tyr Leu Gly Pro Phe Asn Gly Leu Asp Lys Gly Glu Pro
            50                  55                  60

Val Asn Ala Ala Asp Ala Ala Ala Leu Glu His Asp Lys Ala Tyr Asp
        65                  70                  75                  80

Gln Gln Leu Lys Ala Gly Asp Asn Pro Tyr Leu Arg Tyr Asn His Ala
                            85                  90                  95

Asp Ala Glu Phe Gln Glu Arg Leu Gln Glu Asp Thr Ser Phe Gly Gly
                            100                 105                 110

Asn Leu Gly Arg Ala Val Phe Gln Ala Lys Lys Arg Val Leu Glu Pro
```

```
            115                 120                 125
Phe Gly Leu Val Glu Glu Gly Ala Lys Thr Ala Pro Gly Lys Lys Arg
    130                 135                 140
Pro Val Glu Gln Ser Pro Gln Glu Pro Asp Ser Ser Ser Gly Ile Gly
145                 150                 155                 160
Lys Thr Gly Gln Gln Pro Ala Lys Lys Arg Leu Asn Phe Gly Gln Thr
                165                 170                 175
Gly Asp Ser Glu Ser Val Pro Asp Pro Gln Pro Leu Gly Glu Pro Pro
                180                 185                 190
Ala Thr Pro Ala Ala Val Gly Pro Thr Thr Met Ala Ser Gly Gly Gly
                195                 200                 205
Ala Pro Met Ala Asp Asn Asn Glu Gly Ala Asp Gly Val Gly Asn Ala
    210                 215                 220
Ser Gly Asn Trp His Cys Asp Ser Thr Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Ala Ser Thr Gly Ala Ser Asn Asp Asn His
                260                 265                 270
Tyr Phe Gly Tyr Ser Thr Pro Trp Gly Tyr Phe Asp Phe Asn Arg Phe
                275                 280                 285
His Cys His Phe Ser Pro Arg Asp Trp Gln Arg Leu Ile Asn Asn Asn
    290                 295                 300
Trp Gly Phe Arg Pro Lys Arg Leu Asn Phe Lys Leu Phe Asn Ile Gln
305                 310                 315                 320
Val Lys Glu Val Thr Thr Asn Asp Gly Val Thr Thr Ile Ala Asn Asn
                325                 330                 335
Leu Thr Ser Thr Val Gln Val Phe Ser Asp Ser Glu Tyr Gln Leu Pro
                340                 345                 350
Tyr Val Leu Gly Ser Ala His Gln Gly Cys Leu Pro Pro Phe Pro Ala
                355                 360                 365
Asp Val Phe Met Ile Pro Gln Tyr Gly Tyr Leu Thr Leu Asn Asn Gly
    370                 375                 380
Ser Gln Ala Val Gly Arg Ser Ser Phe Tyr Cys Leu Glu Tyr Phe Pro
385                 390                 395                 400
Ser Gln Met Leu Arg Thr Gly Asn Asn Phe Thr Phe Ser Tyr Thr Phe
                405                 410                 415
Glu Asp Val Pro Phe His Ser Ser Tyr Ala His Ser Gln Ser Leu Asp
                420                 425                 430
Arg Leu Met Asn Pro Leu Ile Asp Gln Tyr Leu Tyr Tyr Leu Asn Arg
    435                 440                 445
Thr Gln Asn Gln Ser Gly Ser Ala Gln Asn Lys Asp Leu Leu Phe Ser
    450                 455                 460
Arg Gly Ser Pro Ala Gly Met Ser Val Gln Pro Lys Asn Trp Leu Pro
465                 470                 475                 480
Gly Pro Cys Tyr Arg Gln Gln Arg Val Ser Lys Thr Lys Thr Asp Asn
                485                 490                 495
Asn Asn Ser Asn Phe Thr Trp Thr Gly Ala Ser Lys Tyr Asn Leu Asn
                500                 505                 510
Gly Arg Glu Ser Ile Ile Asn Pro Gly Thr Ala Met Ala Ser His Lys
                515                 520                 525
Asp Asp Lys Asp Lys Phe Phe Pro Met Ser Gly Val Met Ile Phe Gly
    530                 535                 540
```

```
Lys Glu Ser Ala Gly Ala Ser Asn Thr Ala Leu Asp Asn Val Met Ile
545                 550                 555                 560

Thr Asp Glu Glu Ile Lys Ala Thr Asn Pro Val Ala Thr Glu Arg
                565                 570                 575

Phe Gly Thr Val Ala Val Asn Leu Gln Ser Ser Thr Asp Pro Ala
            580                 585                 590

Thr Gly Asp Val His Val Met Gly Ala Leu Pro Gly Met Val Trp Gln
        595                 600                 605

Asp Arg Asp Val Tyr Leu Gln Gly Pro Ile Trp Ala Lys Ile Pro His
        610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735
```

<210> SEQ ID NO 33
<211> LENGTH: 746
<212> TYPE: PRT
<213> ORGANISM: Adeno-associated virus

<400> SEQUENCE: 33

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Ala Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
```

```
                180                 185                 190
Pro Ala Ala Pro Ser Ser Val Gly Ser Gly Thr Val Ala Ala Gly Gly
            195                 200                 205
Gly Ala Pro Met Ala Asp Asn Asn Glu Gly Ala Asp Gly Val Gly Asn
            210                 215                 220
Ala Ser Gly Asn Trp His Cys Asp Ser Thr Trp Leu Gly Asp Arg Val
225                 230                 235                 240
Ile Thr Thr Ser Thr Arg Thr Trp Ala Leu Pro Thr Tyr Asn Asn His
            245                 250                 255
Leu Tyr Lys Gln Ile Ser Ser Glu Thr Ala Gly Ser Thr Asn Asp Asn
            260                 265                 270
Thr Tyr Phe Gly Tyr Ser Thr Pro Trp Gly Tyr Phe Asp Phe Asn Arg
            275                 280                 285
Phe His Cys His Phe Ser Pro Arg Asp Trp Gln Arg Leu Ile Asn Asn
            290                 295                 300
Asn Trp Gly Phe Arg Pro Lys Lys Leu Arg Phe Lys Leu Phe Asn Ile
305                 310                 315                 320
Gln Val Lys Glu Val Thr Thr Asn Asp Gly Val Thr Thr Ile Ala Asn
            325                 330                 335
Asn Leu Thr Ser Thr Ile Gln Val Phe Ser Asp Ser Glu Tyr Gln Leu
            340                 345                 350
Pro Tyr Val Leu Gly Ser Ala His Gln Gly Cys Leu Pro Pro Phe Pro
            355                 360                 365
Ala Asp Val Phe Met Ile Pro Gln Tyr Gly Tyr Leu Thr Leu Asn Asn
            370                 375                 380
Gly Ser Gln Ser Val Gly Arg Ser Ser Phe Tyr Cys Leu Glu Tyr Phe
385                 390                 395                 400
Pro Ser Gln Met Leu Arg Thr Gly Asn Asn Phe Glu Phe Ser Tyr Ser
            405                 410                 415
Phe Glu Asp Val Pro Phe His Ser Ser Tyr Ala His Ser Gln Ser Leu
            420                 425                 430
Asp Arg Leu Met Asn Pro Leu Ile Asp Gln Tyr Leu Tyr Tyr Leu Ala
            435                 440                 445
Arg Thr Gln Ser Asn Pro Gly Gly Thr Ala Gly Asn Arg Glu Leu Gln
            450                 455                 460
Phe Tyr Gln Gly Gly Pro Ser Thr Met Ala Glu Gln Ala Lys Asn Trp
465                 470                 475                 480
Leu Pro Gly Pro Cys Phe Arg Gln Gln Arg Val Ser Lys Thr Leu Asp
            485                 490                 495
Gln Asn Asn Asn Ser Asn Phe Ala Trp Thr Gly Ala Thr Lys Tyr His
            500                 505                 510
Leu Asn Gly Arg Asn Ser Leu Val Asn Pro Gly Val Ala Met Ala Thr
            515                 520                 525
His Lys Asp Asp Glu Asp Arg Phe Phe Pro Ser Ser Gly Val Leu Ile
            530                 535                 540
Phe Gly Lys Thr Gly Ala Thr Asn Lys Thr Thr Leu Glu Asn Val Leu
545                 550                 555                 560
Met Thr Asn Glu Glu Glu Ile Arg Pro Thr Asn Pro Val Ala Thr Glu
            565                 570                 575
Glu Tyr Gly Ile Val Ser Ser Asn Leu Gln Gly Gln Arg Gly Asn Glu
            580                 585                 590
Ala Arg Val Arg Glu Ala Gln Ala Ala Gln Thr Gln Val Val Asn Asn
            595                 600                 605
```

```
Gln Gly Ala Leu Pro Gly Met Val Trp Gln Asn Arg Asp Val Tyr Leu
    610                 615                 620

Gln Gly Pro Ile Trp Ala Lys Ile Pro His Thr Asp Gly Asn Phe His
625                 630                 635                 640

Pro Ser Pro Leu Met Gly Gly Phe Gly Leu Lys His Pro Pro Pro Gln
                645                 650                 655

Ile Leu Ile Lys Asn Thr Pro Val Pro Ala Asn Pro Pro Glu Val Phe
            660                 665                 670

Thr Pro Ala Lys Phe Ala Ser Phe Ile Thr Gln Tyr Ser Thr Gly Gln
        675                 680                 685

Val Ser Val Glu Ile Glu Trp Glu Leu Gln Lys Glu Asn Ser Lys Arg
    690                 695                 700

Trp Asn Pro Glu Ile Gln Tyr Thr Ser Asn Phe Glu Lys Gln Thr Gly
705                 710                 715                 720

Val Asp Phe Ala Val Asp Ser Gln Gly Val Tyr Ser Glu Pro Arg Pro
                725                 730                 735

Ile Gly Thr Arg Tyr Leu Thr Arg Asn Leu
            740                 745

<210> SEQ ID NO 34
<211> LENGTH: 738
<212> TYPE: PRT
<213> ORGANISM: Adeno-associated virus

<400> SEQUENCE: 34

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
```

-continued

```
            225                 230                 235                 240
    Ile Thr Thr Ser Thr Arg Thr Trp Ala Leu Pro Thr Tyr Asn Asn His
                    245                 250                 255
    Leu Tyr Lys Gln Ile Ser Asn Gly Thr Ser Gly Ala Thr Asn Asp
                    260                 265                 270
    Asn Thr Tyr Phe Gly Tyr Ser Thr Pro Trp Gly Tyr Phe Asp Phe Asn
                    275                 280                 285
    Arg Phe His Cys His Phe Ser Pro Arg Asp Trp Gln Arg Leu Ile Asn
                    290                 295                 300
    Asn Asn Trp Gly Phe Arg Pro Lys Arg Leu Ser Phe Lys Leu Phe Asn
    305                 310                 315                 320
    Ile Gln Val Lys Glu Val Thr Gln Asn Glu Gly Thr Lys Thr Ile Ala
                    325                 330                 335
    Asn Asn Leu Thr Ser Thr Ile Gln Val Phe Thr Asp Ser Glu Tyr Gln
                    340                 345                 350
    Leu Pro Tyr Val Leu Gly Ser Ala His Gln Gly Cys Leu Pro Pro Phe
                    355                 360                 365
    Pro Ala Asp Val Phe Met Ile Pro Gln Tyr Gly Tyr Leu Thr Leu Asn
                    370                 375                 380
    Asn Gly Ser Gln Ala Val Gly Arg Ser Ser Phe Tyr Cys Leu Glu Tyr
    385                 390                 395                 400
    Phe Pro Ser Gln Met Leu Arg Thr Gly Asn Asn Phe Gln Phe Thr Tyr
                    405                 410                 415
    Thr Phe Glu Asp Val Pro Phe His Ser Ser Tyr Ala His Ser Gln Ser
                    420                 425                 430
    Leu Asp Arg Leu Met Asn Pro Leu Ile Asp Gln Tyr Leu Tyr Tyr Leu
                    435                 440                 445
    Ser Arg Thr Gln Thr Thr Gly Gly Thr Ala Asn Thr Gln Thr Leu Gly
                    450                 455                 460
    Phe Ser Gln Gly Gly Pro Asn Thr Met Ala Asn Gln Ala Lys Asn Trp
    465                 470                 475                 480
    Leu Pro Gly Pro Cys Tyr Arg Gln Gln Arg Val Ser Thr Thr Thr Gly
                    485                 490                 495
    Gln Asn Asn Asn Ser Asn Phe Ala Trp Thr Ala Gly Thr Lys Tyr His
                    500                 505                 510
    Leu Asn Gly Arg Asn Ser Leu Ala Asn Pro Gly Ile Ala Met Ala Thr
                    515                 520                 525
    His Lys Asp Asp Glu Glu Arg Phe Phe Pro Ser Asn Gly Ile Leu Ile
                    530                 535                 540
    Phe Gly Lys Gln Asn Ala Ala Arg Asp Asn Ala Asp Tyr Ser Asp Val
    545                 550                 555                 560
    Met Leu Thr Ser Glu Glu Ile Lys Thr Thr Asn Pro Val Ala Thr
                    565                 570                 575
    Glu Glu Tyr Gly Ile Val Ala Asp Asn Leu Gln Gln Asn Thr Ala
                    580                 585                 590
    Pro Gln Ile Gly Thr Val Asn Ser Gln Gly Ala Leu Pro Gly Met Val
                    595                 600                 605
    Trp Gln Asn Arg Asp Val Tyr Leu Gln Gly Pro Ile Trp Ala Lys Ile
                    610                 615                 620
    Pro His Thr Asp Gly Asn Phe His Pro Ser Pro Leu Met Gly Gly Phe
    625                 630                 635                 640
    Gly Leu Lys His Pro Pro Gln Ile Leu Ile Lys Asn Thr Pro Val
                    645                 650                 655
```

-continued

```
Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu
```

<210> SEQ ID NO 35
<211> LENGTH: 736
<212> TYPE: PRT
<213> ORGANISM: Adeno-associated virus

<400> SEQUENCE: 35

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285
```

-continued

Phe His Cys His Phe Ser Pro Arg Asp Trp Gln Arg Leu Ile Asn Asn
            290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
                355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
                435                 440                 445

Lys Thr Ile Asn Gly Ser Gly Gln Asn Gln Gln Thr Leu Lys Phe Ser
            450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
            530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
690                 695                 700

```
Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
            725                 730                 735

<210> SEQ ID NO 36
<211> LENGTH: 738
<212> TYPE: PRT
<213> ORGANISM: Adeno-associated virus

<400> SEQUENCE: 36

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
            85                  90                  95

Asp Ala Glu Phe Gln Glu Arg Leu Gln Glu Asp Thr Ser Phe Gly Gly
        100                 105                 110

Asn Leu Gly Arg Ala Val Phe Gln Ala Lys Lys Arg Val Leu Glu Pro
    115                 120                 125

Leu Gly Leu Val Glu Glu Ala Ala Lys Thr Ala Pro Gly Lys Lys Arg
130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
            165                 170                 175

Thr Gly Glu Ser Glu Ser Val Pro Asp Pro Gln Pro Ile Gly Glu Pro
        180                 185                 190

Pro Ala Gly Pro Ser Gly Leu Gly Ser Gly Thr Met Ala Ala Gly Gly
    195                 200                 205

Gly Ala Pro Met Ala Asp Asn Asn Glu Gly Ala Asp Gly Val Gly Ser
210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
            245                 250                 255

Leu Tyr Lys Gln Ile Ser Asn Gly Thr Ser Gly Gly Ser Thr Asn Asp
        260                 265                 270

Asn Thr Tyr Phe Gly Tyr Ser Thr Pro Trp Gly Tyr Phe Asp Phe Asn
    275                 280                 285

Arg Phe His Cys His Phe Ser Pro Arg Asp Trp Gln Arg Leu Ile Asn
290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
            325                 330                 335

Asn Asn Leu Thr Ser Thr Ile Gln Val Phe Thr Asp Ser Glu Tyr Gln
        340                 345                 350
```

Leu Pro Tyr Val Leu Gly Ser Ala His Gln Gly Cys Leu Pro Pro Phe
         355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Phe Tyr Cys Leu Glu Tyr
385                 390                 395                 400

Phe Pro Ser Gln Met Leu Arg Thr Gly Asn Asn Phe Glu Phe Ser Tyr
                 405                 410                 415

Thr Phe Glu Asp Val Pro Phe His Ser Ser Tyr Ala His Ser Gln Ser
                 420                 425                 430

Leu Asp Arg Leu Met Asn Pro Leu Ile Asp Gln Tyr Leu Tyr Tyr Leu
                 435                 440                 445

Ser Arg Thr Gln Ser Thr Gly Gly Thr Gln Gly Thr Gln Gln Leu Leu
                 450                 455                 460

Phe Ser Gln Ala Gly Pro Ala Asn Met Ser Ala Gln Ala Lys Asn Trp
465                 470                 475                 480

Leu Pro Gly Pro Cys Tyr Arg Gln Gln Arg Val Ser Thr Thr Leu Ser
                 485                 490                 495

Gln Asn Asn Asn Ser Asn Phe Ala Trp Thr Gly Ala Thr Lys Tyr His
                 500                 505                 510

Leu Asn Gly Arg Asp Ser Leu Val Asn Pro Gly Val Ala Met Ala Thr
                 515                 520                 525

His Lys Asp Asp Glu Glu Arg Phe Phe Pro Ser Ser Gly Val Leu Met
                 530                 535                 540

Phe Gly Lys Gln Gly Ala Gly Arg Asp Asn Val Asp Tyr Ser Ser Val
545                 550                 555                 560

Met Leu Thr Ser Glu Glu Glu Ile Lys Thr Thr Asn Pro Val Ala Thr
                 565                 570                 575

Glu Gln Tyr Gly Val Val Ala Asp Asn Leu Gln Gln Ala Asn Thr Gly
                 580                 585                 590

Pro Ile Val Gly Asn Val Asn Ser Gln Gly Ala Leu Pro Gly Met Val
                 595                 600                 605

Trp Gln Asn Arg Asp Val Tyr Leu Gln Gly Pro Ile Trp Ala Lys Ile
                 610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                 645                 650                 655

Pro Ala Asp Pro Pro Thr Thr Phe Ser Gln Ala Lys Leu Ala Ser Phe
                 660                 665                 670

Ile Thr Gln Tyr Ser Thr Gly Gln Val Ser Val Glu Ile Glu Trp Glu
                 675                 680                 685

Leu Gln Lys Glu Asn Ser Lys Arg Trp Asn Pro Glu Ile Gln Tyr Thr
                 690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                 725                 730                 735

Asn Leu

<210> SEQ ID NO 37
<211> LENGTH: 733
<212> TYPE: PRT

<213> ORGANISM: Adeno-associated virus

<400> SEQUENCE: 37

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Leu Glu Ser Pro Gln Glu Pro Asp Ser Ser Gly Ile Gly Lys
145                 150                 155                 160

Lys Gly Lys Gln Pro Ala Arg Lys Arg Leu Asn Phe Glu Glu Asp Thr
                165                 170                 175

Gly Ala Gly Asp Gly Pro Pro Glu Gly Ser Asp Thr Ser Ala Met Ser
            180                 185                 190

Ser Asp Ile Glu Met Arg Ala Ala Pro Gly Gly Asn Ala Val Asp Ala
        195                 200                 205

Gly Gln Gly Ser Asp Gly Val Gly Asn Ala Ser Gly Asp Trp His Cys
    210                 215                 220

Asp Ser Thr Trp Ser Glu Gly Lys Val Thr Thr Thr Ser Thr Arg Thr
225                 230                 235                 240

Trp Val Leu Pro Thr Tyr Asn Asn His Leu Tyr Leu Arg Leu Gly Thr
                245                 250                 255

Thr Ser Ser Ser Asn Thr Tyr Asn Gly Phe Ser Thr Pro Trp Gly Tyr
            260                 265                 270

Phe Asp Phe Asn Arg Phe His Cys His Phe Ser Pro Arg Asp Trp Gln
        275                 280                 285

Arg Leu Ile Asn Asn Asn Trp Gly Leu Arg Pro Lys Ala Met Arg Val
    290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
            340                 345                 350

Leu Pro Pro Phe Pro Asn Asp Val Phe Met Val Pro Gln Tyr Gly Tyr
        355                 360                 365

Cys Gly Ile Val Thr Gly Glu Asn Gln Asn Gln Thr Asp Arg Asn Ala
    370                 375                 380

Phe Tyr Cys Leu Glu Tyr Phe Pro Ser Gln Met Leu Arg Thr Gly Asn
385                 390                 395                 400

```
Asn Phe Glu Met Ala Tyr Asn Phe Glu Lys Val Pro Phe His Ser Met
            405                 410                 415

Tyr Ala His Ser Gln Ser Leu Asp Arg Leu Met Asn Pro Leu Leu Asp
        420                 425                 430

Gln Tyr Leu Trp His Leu Gln Ser Thr Thr Ser Gly Glu Thr Leu Asn
            435                 440                 445

Gln Gly Asn Ala Ala Thr Thr Phe Gly Lys Ile Arg Ser Gly Asp Phe
    450                 455                 460

Ala Phe Tyr Arg Lys Asn Trp Leu Pro Gly Pro Cys Val Lys Gln Gln
465                 470                 475                 480

Arg Phe Ser Lys Thr Ala Ser Gln Asn Tyr Lys Ile Pro Ala Ser Gly
                485                 490                 495

Gly Asn Ala Leu Leu Lys Tyr Asp Thr His Tyr Thr Leu Asn Asn Arg
            500                 505                 510

Trp Ser Asn Ile Ala Pro Gly Pro Pro Met Ala Thr Ala Gly Pro Ser
        515                 520                 525

Asp Gly Asp Phe Ser Asn Ala Gln Leu Ile Phe Pro Gly Pro Ser Val
            530                 535                 540

Thr Gly Asn Thr Thr Thr Ser Ala Asn Asn Leu Leu Phe Thr Ser Glu
545                 550                 555                 560

Glu Glu Ile Ala Ala Thr Asn Pro Arg Asp Thr Asp Met Phe Gly Gln
                565                 570                 575

Ile Ala Asp Asn Asn Gln Asn Ala Thr Thr Ala Pro Ile Thr Gly Asn
            580                 585                 590

Val Thr Ala Met Gly Val Leu Pro Gly Met Val Trp Gln Asn Arg Asp
        595                 600                 605

Ile Tyr Tyr Gln Gly Pro Ile Trp Ala Lys Ile Pro His Ala Asp Gly
    610                 615                 620

His Phe His Pro Ser Pro Leu Ile Gly Phe Gly Leu Lys His Pro
625                 630                 635                 640

Pro Pro Gln Ile Phe Ile Lys Asn Thr Pro Val Pro Ala Asn Pro Ala
                645                 650                 655

Thr Thr Phe Thr Ala Ala Arg Val Asp Ser Phe Ile Thr Gln Tyr Ser
            660                 665                 670

Thr Gly Gln Val Ala Val Gln Ile Glu Trp Glu Ile Glu Lys Glu Arg
        675                 680                 685

Ser Lys Arg Trp Asn Pro Glu Val Gln Phe Thr Ser Asn Tyr Gly Asn
    690                 695                 700

Gln Ser Ser Met Leu Trp Ala Pro Asp Thr Thr Gly Lys Tyr Thr Glu
705                 710                 715                 720

Pro Arg Val Ile Gly Ser Arg Tyr Leu Thr Asn His Leu
                725                 730

<210> SEQ ID NO 38
<211> LENGTH: 742
<212> TYPE: PRT
<213> ORGANISM: Adeno-associated virus

<400> SEQUENCE: 38

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Gly Arg Gly Leu Val Leu Pro
        35                  40                  45
```

```
Gly Tyr Lys Tyr Leu Gly Pro Phe Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Lys Gln Leu Glu Gln Gly Asp Asn Pro Tyr Leu Lys Tyr Asn His Ala
                    85                  90                  95

Asp Ala Glu Phe Gln Gln Arg Leu Ala Thr Asp Thr Ser Phe Gly Gly
                100                 105                 110

Asn Leu Gly Arg Ala Val Phe Gln Ala Lys Lys Arg Ile Leu Glu Pro
            115                 120                 125

Leu Gly Leu Val Glu Glu Gly Val Lys Thr Ala Pro Gly Lys Lys Arg
    130                 135                 140

Pro Leu Glu Lys Thr Pro Asn Arg Pro Thr Asn Pro Asp Ser Gly Lys
145                 150                 155                 160

Ala Pro Ala Lys Lys Lys Gln Lys Asp Gly Glu Pro Ala Asp Ser Ala
                165                 170                 175

Arg Arg Thr Leu Asp Phe Glu Asp Ser Gly Ala Gly Asp Gly Pro Pro
                180                 185                 190

Glu Gly Ser Ser Ser Gly Glu Met Ser His Asp Ala Glu Met Arg Ala
            195                 200                 205

Ala Pro Gly Gly Asn Ala Val Glu Ala Gly Gln Gly Ala Asp Gly Val
    210                 215                 220

Gly Asn Ala Ser Gly Asp Trp His Cys Asp Ser Thr Trp Ser Glu Gly
225                 230                 235                 240

Arg Val Thr Thr Thr Ser Thr Arg Thr Trp Val Leu Pro Thr Tyr Asn
                245                 250                 255

Asn His Leu Tyr Leu Arg Ile Gly Thr Thr Ala Asn Ser Asn Thr Tyr
                260                 265                 270

Asn Gly Phe Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
    290                 295                 300

Gly Leu Arg Pro Lys Ser Met Arg Val Lys Ile Phe Asn Ile Gln Val
305                 310                 315                 320

Lys Glu Val Thr Thr Ser Asn Gly Glu Thr Thr Val Ala Asn Asn Leu
                325                 330                 335

Thr Ser Thr Val Gln Ile Phe Ala Asp Ser Thr Tyr Glu Leu Pro Tyr
                340                 345                 350

Val Met Asp Ala Gly Gln Glu Gly Ser Phe Pro Pro Phe Pro Asn Asp
            355                 360                 365

Val Phe Met Val Pro Gln Tyr Gly Tyr Cys Gly Val Val Thr Gly Lys
    370                 375                 380

Asn Gln Asn Gln Thr Asp Arg Asn Ala Phe Tyr Cys Leu Glu Tyr Phe
385                 390                 395                 400

Pro Ser Gln Met Leu Arg Thr Gly Asn Asn Phe Glu Val Ser Tyr Gln
                405                 410                 415

Phe Glu Lys Val Pro Phe His Ser Met Tyr Ala His Ser Gln Ser Leu
                420                 425                 430

Asp Arg Met Met Asn Pro Leu Leu Asp Gln Tyr Leu Trp His Leu Gln
            435                 440                 445

Ser Thr Thr Thr Gly Asn Ser Leu Asn Gln Gly Thr Ala Thr Thr Thr
    450                 455                 460
```

```
Tyr Gly Lys Ile Thr Thr Gly Asp Phe Ala Tyr Tyr Arg Lys Asn Trp
465                 470                 475                 480

Leu Pro Gly Ala Cys Ile Lys Gln Gln Lys Phe Ser Lys Asn Ala Asn
                485                 490                 495

Gln Asn Tyr Lys Ile Pro Ala Ser Gly Gly Asp Ala Leu Leu Lys Tyr
            500                 505                 510

Asp Thr His Thr Thr Leu Asn Gly Arg Trp Ser Asn Met Ala Pro Gly
        515                 520                 525

Pro Pro Met Ala Thr Ala Gly Ala Gly Asp Ser Asp Phe Ser Asn Ser
    530                 535                 540

Gln Leu Ile Phe Ala Gly Pro Asn Pro Ser Gly Asn Thr Thr Thr Ser
545                 550                 555                 560

Ser Asn Asn Leu Leu Phe Thr Ser Glu Glu Glu Ile Ala Thr Thr Asn
                565                 570                 575

Pro Arg Asp Thr Asp Met Phe Gly Gln Ile Ala Asp Asn Asn Gln Asn
                580                 585                 590

Ala Thr Thr Ala Pro His Ile Ala Asn Leu Asp Ala Met Gly Ile Val
                595                 600                 605

Pro Gly Met Val Trp Gln Asn Arg Asp Ile Tyr Tyr Gln Gly Pro Ile
    610                 615                 620

Trp Ala Lys Val Pro His Thr Asp Gly His Phe His Pro Ser Pro Leu
625                 630                 635                 640

Met Gly Gly Phe Gly Leu Lys His Pro Pro Pro Gln Ile Phe Ile Lys
                645                 650                 655

Asn Thr Pro Val Pro Ala Asn Pro Asn Thr Thr Phe Ser Ala Ala Arg
                660                 665                 670

Ile Asn Ser Phe Leu Thr Gln Tyr Ser Thr Gly Gln Val Ala Val Gln
            675                 680                 685

Ile Asp Trp Glu Ile Gln Lys Glu His Ser Lys Arg Trp Asn Pro Glu
        690                 695                 700

Val Gln Phe Thr Ser Asn Tyr Gly Thr Gln Asn Ser Met Leu Trp Ala
705                 710                 715                 720

Pro Asp Asn Ala Gly Asn Tyr His Glu Leu Arg Ala Ile Gly Ser Arg
                725                 730                 735

Phe Leu Thr His His Leu
            740

<210> SEQ ID NO 39
<211> LENGTH: 733
<212> TYPE: PRT
<213> ORGANISM: Adeno-associated virus

<400> SEQUENCE: 39

Met Thr Asp Gly Tyr Leu Pro Asp Trp Leu Glu Asp Asn Leu Ser Glu
1               5                   10                  15

Gly Val Arg Glu Trp Trp Ala Leu Gln Pro Gly Ala Pro Lys Pro Lys
            20                  25                  30

Ala Asn Gln Gln His Gln Asp Asn Ala Arg Gly Leu Val Leu Pro Gly
        35                  40                  45

Tyr Lys Tyr Leu Gly Pro Gly Asn Gly Leu Asp Lys Gly Glu Pro Val
    50                  55                  60

Asn Ala Ala Asp Ala Ala Ala Leu Glu His Asp Lys Ala Tyr Asp Gln
65                  70                  75                  80

Gln Leu Lys Ala Gly Asp Asn Pro Tyr Leu Lys Tyr Asn His Ala Asp
                85                  90                  95
```

```
Ala Glu Phe Gln Glu Arg Leu Gln Glu Asp Thr Ser Phe Gly Gly Asn
            100                 105                 110

Leu Gly Arg Ala Val Phe Gln Ala Lys Lys Arg Ile Leu Glu Pro Leu
        115                 120                 125

Gly Leu Val Glu Glu Ala Ala Lys Thr Ala Pro Gly Lys Lys Arg Pro
    130                 135                 140

Val Glu Gln Ser Pro Ala Glu Pro Asp Ser Ser Gly Ile Gly Lys
145                 150                 155                 160

Ser Gly Gln Gln Pro Ala Arg Lys Arg Leu Asn Phe Gly Gln Thr Gly
                165                 170                 175

Asp Thr Glu Ser Val Pro Asp Pro Gln Pro Leu Gly Gln Pro Pro Ala
            180                 185                 190

Ala Pro Ser Gly Val Gly Ser Thr Thr Met Ala Ser Gly Gly Gly Ala
        195                 200                 205

Pro Met Ala Asp Asn Asn Glu Gly Ala Asp Gly Val Gly Asn Ser Ser
    210                 215                 220

Gly Asn Trp His Cys Asp Ser Gln Trp Leu Gly Asp Arg Val Ile Thr
225                 230                 235                 240

Thr Ser Thr Arg Thr Trp Ala Leu Pro Thr Tyr Asn Asn His Leu Tyr
                245                 250                 255

Lys Gln Ile Ser Ser Gln Ser Gly Ala Thr Asn Asp Asn His Tyr Phe
            260                 265                 270

Gly Tyr Ser Thr Pro Trp Gly Tyr Phe Asp Phe Asn Arg Phe His Cys
        275                 280                 285

His Phe Ser Pro Arg Asp Trp Gln Arg Leu Ile Asn Asn Asn Trp Gly
    290                 295                 300

Phe Arg Pro Lys Arg Leu Asn Phe Lys Leu Phe Asn Ile Gln Val Lys
305                 310                 315                 320

Glu Val Thr Gln Asn Asp Gly Thr Thr Thr Ile Ala Asn Asn Leu Thr
                325                 330                 335

Ser Thr Val Gln Val Phe Thr Asp Ser Glu Tyr Gln Leu Pro Tyr Val
            340                 345                 350

Leu Gly Ser Ala His Gln Gly Cys Leu Pro Pro Phe Pro Ala Asp Val
        355                 360                 365

Phe Met Val Pro Gln Tyr Gly Tyr Leu Thr Leu Asn Asn Gly Ser Gln
    370                 375                 380

Ala Val Gly Arg Ser Ser Phe Tyr Cys Leu Glu Tyr Phe Pro Ser Gln
385                 390                 395                 400

Met Leu Arg Thr Gly Asn Asn Phe Gln Phe Ser Tyr Thr Phe Glu Asp
                405                 410                 415

Val Pro Phe His Ser Ser Tyr Ala His Ser Gln Ser Leu Asp Arg Leu
            420                 425                 430

Met Asn Pro Leu Ile Asp Gln Tyr Leu Tyr Tyr Leu Asn Arg Thr Gln
        435                 440                 445

Thr Ala Ser Gly Thr Gln Gln Ser Arg Leu Leu Phe Ser Gln Ala Gly
    450                 455                 460

Pro Thr Ser Met Ser Leu Gln Ala Lys Asn Trp Leu Pro Gly Pro Cys
465                 470                 475                 480

Tyr Arg Gln Gln Arg Leu Ser Lys Gln Ala Asn Asp Asn Asn Asn Ser
                485                 490                 495

Asn Phe Pro Trp Thr Gly Ala Thr Lys Tyr His Leu Asn Gly Arg Asp
            500                 505                 510
```

-continued

```
Ser Leu Val Asn Pro Gly Pro Ala Met Ala Ser His Lys Asp Asp Lys
        515                 520                 525

Glu Lys Phe Phe Pro Met His Gly Thr Leu Ile Phe Gly Lys Glu Gly
    530                 535                 540

Thr Asn Ala Asn Ala Asp Leu Glu Asn Val Met Ile Thr Asp Glu
545                 550                 555                 560

Glu Glu Ile Arg Thr Thr Asn Pro Val Ala Thr Glu Gln Tyr Gly Thr
                565                 570                 575

Val Ser Asn Asn Leu Gln Asn Ser Asn Ala Gly Pro Thr Thr Gly Thr
            580                 585                 590

Val Asn His Gln Gly Ala Leu Pro Gly Met Val Trp Gln Asp Arg Asp
        595                 600                 605

Val Tyr Leu Gln Gly Pro Ile Trp Ala Lys Ile Pro His Thr Asp Gly
    610                 615                 620

His Phe His Pro Ser Pro Leu Met Gly Gly Phe Gly Leu Lys His Pro
625                 630                 635                 640

Pro Pro Gln Ile Met Ile Lys Asn Thr Pro Val Pro Ala Asn Pro Pro
                645                 650                 655

Thr Asn Phe Ser Ala Ala Lys Phe Ala Ser Phe Ile Thr Gln Tyr Ser
            660                 665                 670

Thr Gly Gln Val Ser Val Glu Ile Glu Trp Glu Leu Gln Lys Glu Asn
        675                 680                 685

Ser Lys Arg Trp Asn Pro Glu Ile Gln Tyr Thr Ser Asn Tyr Asn Lys
    690                 695                 700

Ser Val Asn Val Asp Phe Thr Val Asp Thr Asn Gly Val Tyr Ser Glu
705                 710                 715                 720

Pro Arg Pro Ile Gly Thr Arg Tyr Leu Thr Arg Asn Leu
                725                 730
```

ADENO-ASSOCIATED VIRUS (AAV) WITH MODIFIED PHOSPHOLIPASE DOMAIN

CROSS-REFERENCE TO RELATED APPLICATIONS

This application is a U.S. National Phase Application of International Application No. PCT/IB2018/05661 filed Aug. 30, 2018, which claims the benefit of U.S. Provisional Application Ser. No. 62/553,028, filed Aug. 31, 2017, which are incorporated herein by reference in their entirety.

REFERENCE TO A SEQUENCE LISTING SUBMITTED ELECTRONICALLY VIA EFS-WEB

This application includes a Sequence Listing submitted electronically via EFS-Web (name: "4226.006PC01_Sequence_Listing_ST25.txt"; size: 100,400 bytes; and created on: Aug. 22, 2018), which is hereby incorporated by reference in its entirety.

TECHNICAL FIELD

The present disclosure relates generally to adeno-associated virus (AAV) having a viral capsid protein with a modified phospholipase domain, and methods of producing same using a baculovirus expression system in insect cells.

BACKGROUND

Adeno-associated virus (AAV) is one of the most promising viral vectors for human gene therapy. AAV contains a ssDNA genome of approximately 4.7 kb which expresses two ORFs; one encodes the viral coat proteins VP1, VP2 and VP3 as well as the Assembly Associated Protein or Assembly Activated Protein (AAP) and the second encodes four viral replicase components; the ORFs are flanked by two Inverted Terminal Repeats (ITRs). The ITRs are recognised by the viral rep proteins where they play a crucial role in genome replication and loading of newly synthesized genomes in nascent viral capsids. Recombinant AAV particles can be prepared using vectors where a Gene of Interest (GOI) is cloned between the two ITRs and viral cap and rep proteins are provided in trans.

Recombinant AAV particles retain the ability to efficiently infect dividing as well as non-dividing human cells. Viral particles are thought to enter the nucleus where the genome persists as an episome and continues to express any transgenes present in the recombinant vector for extended periods, months to years. Importantly, even though AAV infection is common, the virus is not generally thought to be associated with any disease. Moreover, there are a number of AAV serotypes, typically termed serotypes 1-12, which differ in their tissue tropisms. In view of these advantages, recombinant adeno-associated virus (rAAV) is being evaluated in gene therapy clinical trials for a number of human diseases.

There are two main types of production systems for recombinant AAV: (1) conventional production systems using mammalian cell lines (e.g., HEK293 cells, COS cells, HeLa cells, KB cells); and (2) more recently, production systems using insect cells.

The mammalian production system typically involves a triple transfection where three plasmids are transfected into mammalian cell lines, these plasmids encode i) AAV rep and coat proteins ii) helper functions derived from adenovirus and iii) a gene of interest flanked by ITRs. The AAV rep and ITR sequences are typically derived from the AAV2 serotype, as well as CAP sequences, although sequences from other serotypes can be substituted to create pseudotyped viral particles, the choice of viral capsid proteins reflecting the desired tissue tropisms.

Mammalian production systems suffer from several drawbacks. The most important drawback for therapeutic use is difficulties associated with large scale transfection of adherent mammalian cells and consequent poor scalability of AAV production systems. Furthermore, there is a risk that a vector for clinical use that is produced in a mammalian cell culture will be contaminated with undesirable, and perhaps pathogenic, material present in the mammalian host cell.

As an alternative to mammalian productions systems, insect cells can be used for the production of AAV using baculovirus vectors. Baculoviruses infect insect cells where they replicate episomally and through the use of baculovirus-derived promoters can drive extremely high levels of transgene expression in infected cells. Typically insect cells are co-infected with two recombinant baculoviruses, one expressing AAV cap and rep proteins and the second containing the GOI flanked by ITRs, viral helper functions are not required.

The principal advantage of using insect cells for production of AAV is scalability, since insect cells have been adapted to grow in suspension culture without supplements such as Fetal Calf Serum. However, insect cell production systems also have several drawbacks, including difficulties in achieving the correct stoichiometry of the three AAV capsid proteins (VP1, VP2 and VP3), passaging instability of the baculovirus expression vectors and, most significantly, low functionality of the resultant AAVs compared to corresponding AAVs produced in conventional mammalian cells.

The functionality of AAVs produced in insects cell varies according to the AAV serotype. For example, Urabe et al. (2006) *J. Virol.* 80(4):1874-1885 reported that AAV5 particles produced in the baculovirus system in insect cell have a poor activity in contrast to AAV2 produced in the same system. It has since been recognised that AAV2 retains activity of the phospholipase domain (PLA) in subunit 1 (VP1) of its viral capsid protein when produced from a baculovirus expression system in insect cells, thereby enabling the virus to escape the endosomal compartment and reach the cell cytoplasm. Urabe et al. partially addressed this problem by constructing chimeric AAV2/5 VP1 proteins, wherein a N-terminal portion of at least 49 amino acids of AAV5 VP1 is replaced with the corresponding part of AAV2 VP1 in order to improve the functionality of the virions. However, given the interest in using AAVs in human gene therapy, there is still a need in the art for alternative and/or improved methods of producing recombinant AAVs (from serotypes other than AAV2) in insect cells, wherein the AAVs are capable of escaping the endosome following cellular internalisation.

It is to be understood that any discussion of public documents, acts, materials, devices, articles or the like included herein is solely for the purpose of providing a context for the present invention. It is not to be taken as an admission that any or all of these matters were common general knowledge in the field relevant to the present invention as it existed before the priority date of any claim of this application.

SUMMARY

The present disclosure is based on the unexpected finding by the inventors that the endosomal escape activity of AAVs from serotypes other than serotype 2, produced from a baculovirus expression system in insect cells, can be restored or improved by making amino acid substitutions at specific sites within the phospholipase domain and flanking region. Specifically, the inventors have shown for the first time that it is possible to restore or improve the endosomal escape activity of two representative AAV serotypes, serotypes 8 and 9, by substituting amino acids at up to six residue positions with the amino acids from AAV serotype 2 at the corresponding positions. In this regard, the present inventors have shown that it is not necessary to swap the entire PLA domain with that of AAV2 to produce chimeric AAVs, nor is it necessary to produce AAVs expressing mosaic capsids comprising the wildtype VP1/PLA sequence and that of AAV2 e.g., AAV2/WT VP1, as has been the strategy employed to date to improve functionality of AAVs produced in insect cells. Thus, the inventors have provided a novel approach by which endosomal escape activity of recombinant non-serotype 2 AAVs produced in insect cells can be restored or improved without having to replace entire domain and/or subunit sequences within the wildtype viral capsid protein of the respective AAV.

Accordingly, the present disclosure provides a nucleic acid molecule comprising a polynucleotide sequence encoding an adeno-associated virus (AAV) viral capsid protein, wherein the viral capsid protein comprises a modified subunit 1 (VP1) sequence comprising a serine at position 1, a glutamic acid at position 26, an arginine at position 40, an aspartic acid at position 43, a serine at position 44 and a lysine at position 64, wherein the amino acid positions are defined relative to the sequence set forth in SEQ ID NO: 1, wherein the amino acids at any one or more of positions 1, 26, 40, 43, 44 and 64 are modified relative to a corresponding wildtype sequence, and wherein no additional amino acids other than those at said any one or more positions 1, 26, 40, 43, 44 and 64 are modified relative to the corresponding wildtype sequence.

In one example, the viral capsid protein is from AAV serotype 1. In one example, the viral capsid protein is from AAV serotype 3. In one example, the viral capsid protein is from AAV serotype 4. In one example, the viral capsid protein is from AAV serotype 5. In one example, the viral capsid protein is from AAV serotype 6. In one example, the viral capsid protein is from AAV serotype 7. In one example, the viral capsid protein is from AAV serotype 8. In one example, the viral capsid protein is from AAV serotype 9. In one example, the viral capsid protein is from AAV serotype 10. In one example, the viral capsid protein is from AAV serotype 11. In one example, the viral capsid protein is from AAV serotype 12. In one example, the viral capsid protein is from AAV serotype 13.

In one example, the viral capsid protein is selected from the group consisting of:

a viral capsid protein from AAV1 wherein the modified VP1 sequence comprises the sequence set forth in SEQ ID NO: 15

(ii) a viral capsid protein from AAV3 wherein the modified VP1 sequence comprises the sequence set forth in SEQ ID NO: 16;

(iii) a viral capsid protein from AAV4 wherein the modified VP1 sequence comprises the sequence set forth in SEQ ID NO: 17;

(iv) a viral capsid protein from AAV5 wherein the modified VP1 sequence comprises the sequence set forth in SEQ ID NO: 18;

(v) a viral capsid protein from AAV6 wherein the modified VP1 sequence comprises the sequence set forth in SEQ ID NO: 19;

(vi) a viral capsid protein from AAV7 wherein the modified VP1 sequence comprises the sequence set forth in SEQ ID NO: 20;

(vii) a viral capsid protein from AAV8 wherein the modified VP1 sequence comprises the sequence set forth in SEQ ID NO: 21;

(viii) a viral capsid protein from AAV9 wherein the modified VP1 sequence comprises the sequence set forth in SEQ ID NO: 22;

(ix) a viral capsid protein from AAV10 wherein the modified VP1 sequence comprises the sequence set forth in SEQ ID NO: 23;

(x) a viral capsid protein from AAV11 wherein the modified VP1 sequence comprises the sequence set forth in SEQ ID NO: 24;

(xi) a viral capsid protein from AAV12 wherein the modified VP1 sequence comprises the sequence set forth in SEQ ID NO: 25; and (xii) a viral capsid protein from AAV13 wherein the modified VP1 sequence comprises the sequence set forth in SEQ ID NO: 26.

In one example, the viral capsid protein is from AAV1 wherein the modified VP1 sequence comprises the sequence set forth in SEQ ID NO: 15.

In one example, the viral capsid protein is from AAV3 wherein the modified VP1 sequence comprises the sequence set forth in SEQ ID NO: 16.

In one example, the viral capsid protein is from AAV4 wherein the modified VP1 sequence comprises the sequence set forth in SEQ ID NO: 17.

In one example, the viral capsid protein is from AAV5 wherein the modified VP1 sequence comprises the sequence set forth in SEQ ID NO: 18.

In one example, the viral capsid protein is from AAV6 wherein the modified VP1 sequence comprises the sequence set forth in SEQ ID NO: 19.

In one example, the viral capsid protein is from AAV7 wherein the modified VP1 sequence comprises the sequence set forth in SEQ ID NO: 20.

In one example, the viral capsid protein is from AAV8 wherein the modified VP1 sequence comprises the sequence set forth in SEQ ID NO: 21.

In one example, the viral capsid protein is from AAV9 wherein the modified VP1 sequence comprises the sequence set forth in SEQ ID NO: 22.

In one example, the viral capsid protein is from AAV10 wherein the modified VP1 sequence comprises the sequence set forth in SEQ ID NO: 23.

In one example, the viral capsid protein is from AAV11 wherein the modified VP1 sequence comprises the sequence set forth in SEQ ID NO: 24.

In one example, the viral capsid protein is from AAV12 wherein the modified VP1 sequence comprises the sequence set forth in SEQ ID NO: 25.

In one example, the viral capsid protein is from AAV13 wherein the modified VP1 sequence comprises the sequence set forth in SEQ ID NO: 26.

In each of the foregoing examples, the viral capsid protein may comprise subunit 2 (VP2) and subunit 3 (VP3) sequences from the same AAV serotype as the modified VP1.

In one example, the nucleotide sequence encoding the AAV viral capsid protein is operably-linked to a promoter for expression in an insect cell. In one example, the promoter is a polyhedron promoter. In another example, the promoter is a p10 promoter.

The nucleic acid molecule may also comprise a polynucleotide sequence encoding at least one large AAV replication (Rep) protein selected from Rep78 and Rep68 and at least one small AAV Rep protein selected from Rep52 and Rep40. In one example, the nucleic acid molecule comprises a polynucleotide sequence encoding Rep78 and Rep52. In one example, the nucleic acid molecule comprises a polynucleotide sequence encoding Rep78 and Rep40. In one example, the nucleic acid molecule comprises a polynucleotide sequence encoding Rep68 and Rep52. In one example, the nucleic acid molecule comprises a polynucleotide sequence encoding Rep68 and Rep40. In one example, the nucleic acid molecule comprises a polynucleotide sequence encoding Rep78, Rep68, Rep52 and Rep40. In each of the foregoing examples, the Rep proteins may be from the same AAV serotype as the viral capsid protein. Alternatively, the Rep proteins may be from a different AAV serotype to that of the viral capsid protein e.g., the Rep proteins may be from AAV serotype 2.

The polynucleotide sequence encoding the Rep proteins may be operably-linked to a promoter for expression of the Rep proteins in an insect cell. In one example, polynucleotide sequence encoding the Rep proteins is operably-linked to a polyhedron promoter. In one example, polynucleotide sequence encoding the Rep proteins is operably-linked to a p10 promoter.

In each of the foregoing examples, the nucleic acid molecule may comprise a polynucleotide encoding an assembly-activating protein (AAP). For example, the AAP may be encoded by a different open reading frame to that encoding the viral capsid protein.

The present disclosure also provides a baculovirus vector comprising the nucleic acid molecule as described herein.

The present disclosure also provides a plurality of baculovirus vectors comprising:
(i) a first baculovirus vector comprising the nucleic acid molecule as described herein, wherein the nucleic acid molecule encodes an AAV viral capsid protein and Rep proteins as described herein; and
(ii) a second baculovirus vector comprising a polynucleotide encoding a protein or RNA of interest flanked by AAV inverted terminal repeat (ITR) sequences.

In one example, the AAV ITR sequences are from the same serotype as the viral capsid protein. In another example, the AAV ITR sequences are from a serotype other than that of the viral capsid protein. In one particular example, the AAV ITR sequences are from AAV serotype 2.

The present disclosure also provides a plurality of baculovirus vectors comprising:
(i) a first baculovirus vector comprising the nucleic acid molecule as described herein, wherein the nucleic acid molecule encodes an AAV viral capsid protein as described herein;
(ii) second baculovirus vector comprising a polynucleotide sequence encoding at least one large AAV replication (Rep) protein selected from Rep78 and Rep68 and at least one small AAV Rep protein selected from Rep52 and Rep40; and
(iii) a third baculovirus vector comprising a polynucleotide encoding a protein or RNA of interest flanked by AAV inverted terminal repeat (ITR) sequences.

In one example, the second baculovirus vector comprises a polynucleotide sequence encoding Rep78 and Rep52. In one example, the second baculovirus vector comprises a polynucleotide sequence encoding Rep78 and Rep40. In one example, the second baculovirus vector comprises a polynucleotide sequence encoding Rep68 and Rep52. In one example, the second baculovirus vector comprises a polynucleotide sequence encoding Rep68 and Rep40. In one example, the second baculovirus vector comprises a polynucleotide sequence encoding Rep78, Rep68, Rep52 and Rep40. In each of the foregoing examples, the Rep proteins may be from the same AAV serotype as the viral capsid protein encoded by the nucleic acid molecule in the first baculovirus vector. Alternatively, the Rep proteins may be from a different AAV serotype to that of the viral capsid protein encoded by the nucleic acid molecule in the first baculovirus vector e.g., the Rep proteins may be from AAV serotype 2.

In each of the foregoing examples, the polynucleotide sequence encoding the Rep proteins within the second baculovirus vector may be operably-linked to a promoter for expression of the Rep proteins in an insect cell. In one example, polynucleotide sequence encoding the Rep proteins within the second baculovirus vector is operably-linked to a polyhedron promoter. In one example, polynucleotide sequence encoding the Rep proteins within the second baculovirus vector is operably-linked to a p10 promoter.

In one example, the third baculovirus vector comprises AAV ITR sequences from the same serotype as the viral capsid protein encoded by the nucleic acid molecule in the first baculovirus vector. In another example, the third baculovirus vector comprises AAV ITR sequences from a serotype other than that of the viral capsid protein encoded by the nucleic acid molecule in the first baculovirus vector. In one particular example, the AAV ITR sequences are from AAV serotype 2.

At least one of the baculovirus vectors comprises a polynucleotide encoding an assembly-activating protein (AAP) for an AAV. In one example, the AAP may be encoded by a polynucleotide sequence comprised within the first baculovirus vector. In one example, the AAP may be encoded by a polynucleotide sequence comprised within the second baculovirus vector. In another example, the AAP may be encoded by a polynucleotide sequence comprised within the third baculovirus vector.

The present disclosure also provides an insect cell comprising the nucleic acid as described herein.

The present disclosure also provides an insect cell comprising a baculovirus vector or a plurality of baculovirus vectors as described herein.

In one example, the polynucleotide sequence encoding the AAV viral capsid protein and/or the polynucleotide sequence encoding the Rep proteins is/are expressed from episomally replicating recombinant baculovirus genomes.

Alternatively, or in addition, the polynucleotide encoding a protein or RNA of interest flanked by AAV inverted terminal repeat (ITR) sequences is expressed from episomally replicating recombinant baculovirus genomes.

The present disclosure also provides a method for producing adeno-associated virus (AAV) in an insect cell comprising:
(i) culturing the insect cell as described herein in culture media under conditions sufficient for the cells to produce AAV; and optionally
(ii) recovering the AAV from the culture media and/or cells.

The present disclosure also provides a method for producing adeno-associated virus (AAV) in an insect cell comprising:

(i) co-infecting an insect cell with: a first baculovirus having a genome comprising the nucleic acid molecule described herein, which encodes an AAV viral capsid protein and Rep proteins as described herein; and a second baculovirus having a genome comprising a polynucleotide encoding a protein or RNA of interest flanked by AAV inverted terminal repeat (ITR) sequences e.g., ITR sequences from AAV serotype2;

(ii) culturing the insect cell infected with the baculoviruses at (i) in culture media under conditions sufficient for the cells to produce AAV; and optionally (iii) recovering the AAV from the culture media and/or cells.

In one example, the method of producing the AAV comprises recovering the AAV from the culture media and/or cells. In another example, the method of producing the AAV comprises recovering the AAV from the culture media and/or cells and then purifying the AAV. In one example, the AAV are recovered from the cells. In one example, the AAV are recovered from the culture media. In one example, the AAV are recovered from the cell and culture media.

The genome of at least one of the first and second baculoviruses will comprise a polynucleotide encoding an assembly-activating protein (AAP) for an AAV. In one example, the AAP may be encoded by a polynucleotide sequence comprised within the genome of the first baculovirus. In one example, the AAP may be encoded by a polynucleotide sequence comprised within the genome of the second baculovirus.

The present disclosure also provides a method for producing adeno-associated virus (AAV) in an insect cell comprising:

(i) co-infecting an insect cell with: a first baculovirus having a genome comprising the nucleic acid molecule as described herein, wherein the nucleic acid molecule encodes an AAV viral capsid protein as described herein; a second baculovirus having a genome comprising a polynucleotide sequence encoding at least one large AAV replication (Rep) protein selected from Rep78 and Rep68 and at least one small AAV Rep protein selected from Rep52 and Rep40; and a third baculovirus having a genome comprising a polynucleotide encoding a protein or RNA of interest flanked by AAV inverted terminal repeat (ITR) sequences;

(ii) culturing the insect cell infected with the baculoviruses at (i) in culture media under conditions sufficient for the cells to produce AAV; and optionally (iii) recovering the AAV from the culture media and/or cells.

In one example, the second baculovirus vector with which the insect cell is infected comprises a polynucleotide sequence encoding Rep78 and Rep52. In one example, the second baculovirus vector with which the insect cell is infected comprises a polynucleotide sequence encoding Rep78 and Rep40. In one example, the second baculovirus vector with which the insect cell is infected comprises a polynucleotide sequence encoding Rep68 and Rep52. In one example, the second baculovirus vector with which the insect cell is infected comprises a polynucleotide sequence encoding Rep68 and Rep40. In one example, the second baculovirus vector with which the insect cell is infected comprises a polynucleotide sequence encoding Rep78, Rep68, Rep52 and Rep40. In each of the foregoing examples, the Rep proteins may be from the same AAV serotype as the viral capsid protein encoded by the nucleic acid molecule in the first baculovirus vector. Alternatively, the Rep proteins may be from a different AAV serotype to that of the viral capsid protein encoded by the nucleic acid molecule in the first baculovirus vector e.g., the Rep proteins may be from AAV serotype 2.

In each of the foregoing examples, the polynucleotide sequence encoding the Rep proteins within the second baculovirus vector may be operably-linked to a promoter for expression of the Rep proteins in an insect cell. In one example, polynucleotide sequence encoding the Rep proteins within the second baculovirus vector is operably-linked to a polyhedron promoter. In one example, polynucleotide sequence encoding the Rep proteins within the second baculovirus vector is operably-linked to a p10 promoter.

In one example, the third baculovirus vector which the insect cell is infected comprises AAV ITR sequences from the same serotype as the viral capsid protein encoded by the nucleic acid molecule in the first baculovirus vector. In another example, the third baculovirus vector which the insect cell is infected comprises AAV ITR sequences from a serotype other than that of the viral capsid protein encoded by the nucleic acid molecule in the first baculovirus vector. In one particular example, the AAV ITR sequences are from AAV serotype 2.

In one example, the Rep proteins encoded by the genome of the second baculovirus vector and the ITR sequences encoded by the genome of the third baculovirus vector are from AAV serotype 2.

The genome of at least one of the first, second and third baculoviruses will comprise a polynucleotide encoding an assembly-activating protein (AAP) for an AAV. In one example, the AAP may be encoded by a polynucleotide sequence comprised within the genome of the first baculovirus. In one example, the AAP may be encoded by a polynucleotide sequence comprised within the genome of the second baculovirus. In one example, the AAP may be encoded by a polynucleotide sequence comprised within the genome of the third baculovirus.

In one example, the method of producing the AAV comprises recovering the AAV from the culture media and/or cells. In another example, the method of producing the AAV comprises recovering the AAV from the culture media and/or cells and then purifying the AAV. In one example, the AAV are recovered from the cells. In one example, the AAV are recovered from the culture media. In one example, the AAV are recovered from the cell and culture media.

The present disclosure also provides an adeno-associated virus (AAV) produced by the method described herein.

Also provided is an adeno-associated virus (AAV) comprising a viral capsid protein comprising a modified subunit 1 (VP1) sequence comprising a serine at position 1, a glutamic acid at position 26, an arginine at position 40, an aspartic acid at position 43, a serine at position 44 and a lysine at position 64, wherein the amino acid positions are defined relative to the sequence set forth in SEQ ID NO: 1, wherein the amino acids at any one or more of positions 1, 26, 40, 43, 44 and 64 are modified relative to a corresponding wildtype sequence, and wherein no additional amino acids other than those at said any one or more positions 1, 26, 40, 43, 44 and 64 are modified relative to the corresponding wildtype sequence.

In one example, the amino acids at any two or more of positions 1, 26, 40, 43, 44 and 64 are modified relative to a corresponding wildtype sequence as described herein. In one example, the amino acids at any three or more of positions 1, 26, 40, 43, 44 and 64 are modified relative to a corresponding wildtype sequence as described herein. In one example, the amino acids at any four or more of positions 1, 26, 40, 43, 44 and 64 are modified relative to a corresponding wildtype sequence as described herein. In one example, the amino acids at any five or more of positions 1, 26, 40, 43, 44 and 64 are modified relative to a corresponding wildtype sequence as described herein. In one example, the amino acids at each of positions 1, 26, 40, 43, 44 and 64 are modified relative to a corresponding wildtype sequence as described herein.

A viral capsid protein comprising a modified VP1 sequence has been described herein, and any example thereof shall be taken to apply mutatis mutandis to the AAVs of the disclosure unless specifically stated otherwise.

In one example, the AAV is selected from the group consisting of:

(i) an AAV serotype 1, wherein the modified VP1 sequence comprises the sequence set forth in SEQ ID NO: 15;

(ii) an AAV serotype 3, wherein the modified VP1 sequence comprises the sequence set forth in SEQ ID NO: 16;

(iii) an AAV serotype 4, wherein the modified VP1 sequence comprises the sequence set forth in SEQ ID NO: 17;

(iv) an AAV serotype 5, wherein the modified VP1 sequence comprises the sequence set forth in SEQ ID NO: 18;

(v) an AAV serotype 6, wherein the modified VP1 sequence comprises the sequence set forth in SEQ ID NO: 19;

(vi) an AAV serotype 7, wherein the modified VP1 sequence comprises the sequence set forth in SEQ ID NO: 20;

(vii) an AAV serotype 8, wherein the modified VP1 sequence comprises the sequence set forth in SEQ ID NO: 21;

(viii) an AAV serotype 9, wherein the modified VP1 sequence comprises the sequence set forth in SEQ ID NO: 22;

(ix) an AAV serotype 10, wherein the modified VP1 sequence comprises the sequence set forth in SEQ ID NO: 23;

(x) an AAV serotype 11, wherein the modified VP1 sequence comprises the sequence set forth in SEQ ID NO: 24;

(xi) an AAV serotype 12, wherein the modified VP1 sequence comprises the sequence set forth in SEQ ID NO: 25; and (xii) an AAV serotype 13, wherein the modified VP1 sequence comprises the sequence set forth in SEQ ID NO: 26.

In one example, the AAV is an AAV serotype 1, wherein the modified VP1 sequence comprises the sequence set forth in SEQ ID NO: 15.

In one example, the AAV is an AAV serotype 3, wherein the modified VP1 sequence comprises the sequence set forth in SEQ ID NO: 16.

In one example, the AAV is an AAV serotype 4, wherein the modified VP1 sequence comprises the sequence set forth in SEQ ID NO: 17.

In one example, the AAV is an AAV serotype 5, wherein the modified VP1 sequence comprises the sequence set forth in SEQ ID NO: 18.

In one example, the AAV is an AAV serotype 6, wherein the modified VP1 sequence comprises the sequence set forth in SEQ ID NO: 19.

In one example, the AAV is an AAV serotype 7, wherein the modified VP1 sequence comprises the sequence set forth in SEQ ID NO: 20.

In one example, the AAV is an AAV serotype 8, wherein the modified VP1 sequence comprises the sequence set forth in SEQ ID NO: 21.

In one example, the AAV is an AAV serotype 9, wherein the modified VP1 sequence comprises the sequence set forth in SEQ ID NO: 22.

In one example, the AAV is an AAV serotype 10, wherein the modified VP1 sequence comprises the sequence set forth in SEQ ID NO: 23.

In one example, the AAV is an AAV serotype 11, wherein the modified VP1 sequence comprises the sequence set forth in SEQ ID NO: 24.

In one example, the AAV is an AAV serotype 12, wherein the modified VP1 sequence comprises the sequence set forth in SEQ ID NO: 25.

In one example, the AAV is an AAV serotype 13, wherein the modified VP1 sequence comprises the sequence set forth in SEQ ID NO: 26.

The present disclosure also provides a method of improving functionality of an adeno-associated virus (AAV) from a serotype other than serotype 2 which is produced in an insect cell, comprising modifying VP1 sequence within a viral capsid protein of the AAV relative to the corresponding wildtype sequence by substituting one or more amino acids at position 1, 26, 40, 43, 44 and 64 only, wherein the residue positions are determined relative to the sequence set forth in SEQ ID NO: 1, such that the viral capsid protein comprises a serine at position 1, a glutamic acid at position 26, an arginine at position 40, an aspartic acid at position 43, a serine at position 44 and a lysine at position 64, and wherein the AAV have improved functionality relative to the corresponding wildtype AAV which has not been modified and which is produced in insect cells. The improved functionality of the AAV will preferably be due to an improved ability of the AAV to escape the endosomal compartment of a cell following internalisation i.e., improved endosomal escape activity. AAV viral capsid proteins comprising modified VP1 sequences have been described herein, and any example thereof shall be taken to apply mutatis mutandis to the method of producing same as described herein unless specifically stated otherwise.

In one example, the method comprises modifying any two or more amino acids at positions 1, 26, 40, 43, 44 and 64 relative to a corresponding wildtype sequence as described herein. In one example, the method comprises modifying any three or more amino acids at positions 1, 26, 40, 43, 44 and 64 relative to a corresponding wildtype sequence as described herein. In one example, the method comprises modifying any four or more amino acids at positions 1, 26, 40, 43, 44 and 64 relative to a corresponding wildtype sequence as described herein. In one example, the method comprises modifying any five or more amino acids at positions 1, 26, 40, 43, 44 and 64 relative to a corresponding wildtype sequence as described herein. In one example, the method comprises modifying the amino acids at positions 1, 26, 40, 43, 44 and 64 relative to a corresponding wildtype sequence as described herein.

In one example, the method comprises modifying the VP1 sequence of a viral capsid protein of AAV relative to the corresponding wildtype sequence, such that:

(i) when the AAV is of serotype 1, the viral capsid protein includes a VP1 sequence comprising the sequence set forth in SEQ ID NO: 15;

(ii) when the AAV is of serotype 3, the viral capsid protein includes a VP1 sequence comprising the sequence set forth in SEQ ID NO: 16;

(iii) when the AAV is of serotype 4, the viral capsid protein includes a VP1 sequence comprising the sequence set forth in SEQ ID NO: 17;

(iv) when the AAV is of serotype 5, the viral capsid protein includes a VP1 sequence comprising the sequence set forth in SEQ ID NO: 18;

(v) when the AAV is of serotype 6, the viral capsid protein includes a VP1 sequence comprising the sequence set forth in SEQ ID NO: 19;

(vi) when the AAV is of serotype 7, the viral capsid protein includes a VP1 sequence comprising the sequence set forth in SEQ ID NO: 20;

(vii) when the AAV is of serotype 8, the viral capsid protein includes a VP1 sequence comprising the sequence set forth in SEQ ID NO: 21;

(viii) when the AAV is of serotype 9, the viral capsid protein includes a VP1 sequence comprising the sequence set forth in SEQ ID NO: 22;

(ix) when the AAV is of serotype 10, the viral capsid protein includes a VP1 sequence comprising the sequence set forth in SEQ ID NO: 23;

(x) when the AAV is of serotype 11, the viral capsid protein includes a VP1 sequence comprising the sequence set forth in SEQ ID NO: 24;

(xi) when the AAV is of serotype 12, the viral capsid protein includes a VP1 sequence comprising the sequence set forth in SEQ ID NO: 25; and (xii) when the AAV is of serotype 13, the viral capsid protein includes a VP1 sequence comprising the sequence set forth in SEQ ID NO: 26.

In one example, the method comprises modifying the VP1 sequence of a viral capsid protein of AAV1 relative to the corresponding wildtype sequence, such that the viral capsid protein includes a VP1 sequence comprising the sequence set forth in SEQ ID NO: 15.

In one example, the method comprises modifying the VP1 sequence of a viral capsid protein of AAV3 relative to the corresponding wildtype sequence, such that the viral capsid protein includes a VP1 sequence comprising the sequence set forth in SEQ ID NO: 16.

In one example, the method comprises modifying the VP1 sequence of a viral capsid protein of AAV4 relative to the corresponding wildtype sequence, such that the viral capsid protein includes a VP1 sequence comprising the sequence set forth in SEQ ID NO: 17.

In one example, the method comprises modifying the VP1 sequence of a viral capsid protein of AAV5 relative to the corresponding wildtype sequence, such that the viral capsid protein includes a VP1 sequence comprising the sequence set forth in SEQ ID NO: 18.

In one example, the method comprises modifying the VP1 sequence of a viral capsid protein of AAV6 relative to the corresponding wildtype sequence, such that the viral capsid protein includes a VP1 sequence comprising the sequence set forth in SEQ ID NO: 19.

In one example, the method comprises modifying the VP1 sequence of a viral capsid protein of AAV7 relative to the corresponding wildtype sequence, such that the viral capsid protein includes a VP1 sequence comprising the sequence set forth in SEQ ID NO: 20.

In one example, the method comprises modifying the VP1 sequence of a viral capsid protein of AAV8 relative to the corresponding wildtype sequence, such that the viral capsid protein includes a VP1 sequence comprising the sequence set forth in SEQ ID NO: 21.

In one example, the method comprises modifying the VP1 sequence of a viral capsid protein of AAV9 relative to the corresponding wildtype sequence, such that the viral capsid protein includes a VP1 sequence comprising the sequence set forth in SEQ ID NO: 22.

In one example, the method comprises modifying the VP1 sequence of a viral capsid protein of AAV10 relative to the corresponding wildtype sequence, such that the viral capsid protein includes a VP1 sequence comprising the sequence set forth in SEQ ID NO: 23.

In one example, the method comprises modifying the VP1 sequence of a viral capsid protein of AAV11 relative to the corresponding wildtype sequence, such that the viral capsid protein includes a VP1 sequence comprising the sequence set forth in SEQ ID NO: 24.

In one example, the method comprises modifying the VP1 sequence of a viral capsid protein of AAV12 relative to the corresponding wildtype sequence, such that the viral capsid protein includes a VP1 sequence comprising the sequence set forth in SEQ ID NO: 25.

In one example, the method comprises modifying the VP1 sequence of a viral capsid protein of AAV13 relative to the corresponding wildtype sequence, such that the viral capsid protein includes a VP1 sequence comprising the sequence set forth in SEQ ID NO: 26.

KEY TO THE SEQUENCE LISTING

Figure 1:
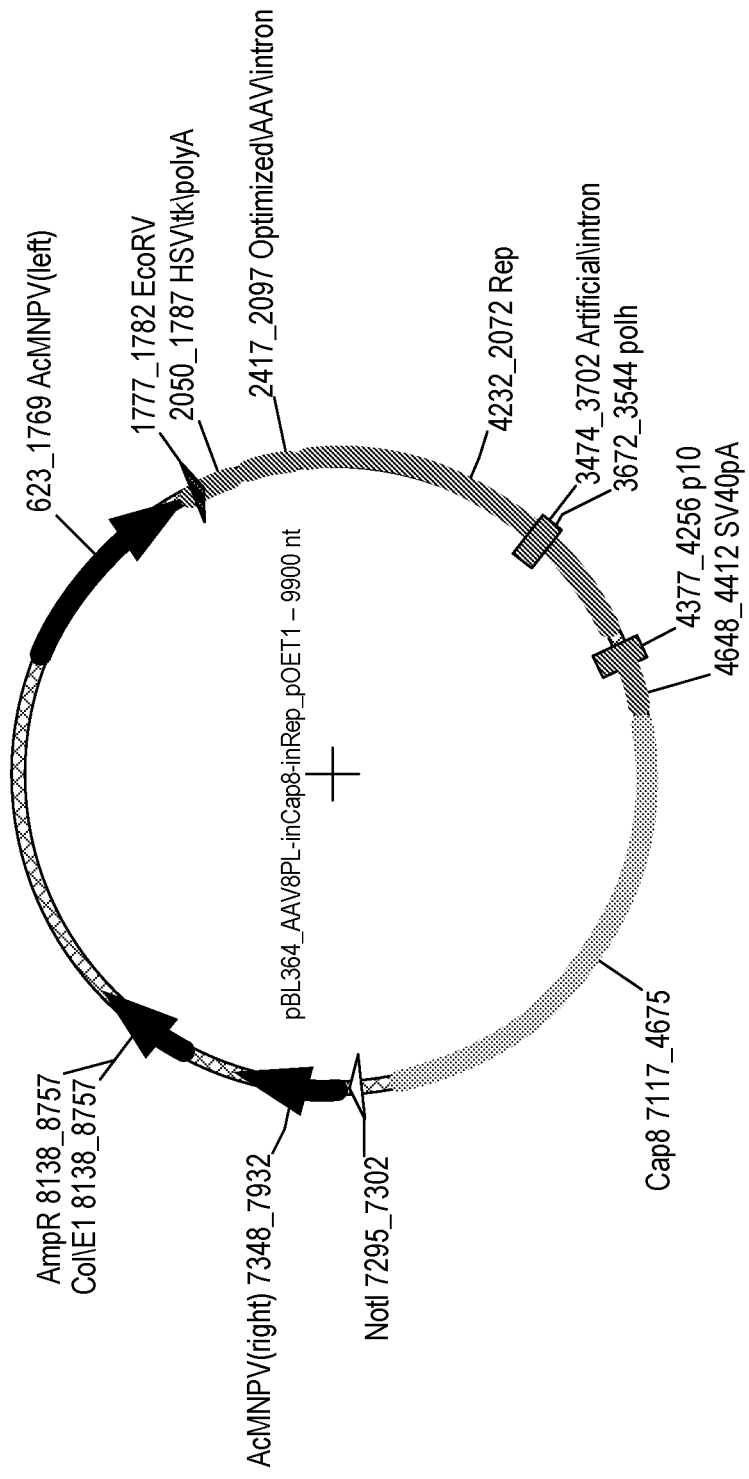
FIG. 1 is a vector map for the DNA construct designated BacAAV8-Rep-VPmod. This DNA construct was designed to express both AAV Rep proteins and the modified AAV8 capsid in insect cells. The vector backbone is a baculovirus vector pOET1 backbone (Oxford Expression Technologies) and was used to prepare AAV containing the modified AAV8 capsid protein in insect cells.

SEQ ID NO: 1: Modified consensus VP1 subsequence for AAV serotypes, comprising the PLA2 domain and flanking sequence.

SEQ ID NO: 2: VP1 subsequence for AAV serotype 1, comprising the PLA2 domain and flanking sequence.

SEQ ID NO: 3: VP1 subsequence for AAV serotype 2, comprising the PLA2 domain and flanking sequence.

SEQ ID NO: 4: VP1 subsequence for AAV serotype 3, comprising the PLA2 domain and flanking sequence.

SEQ ID NO: 5: VP1 subsequence for AAV serotype 4, comprising the PLA2 domain and flanking sequence.

SEQ ID NO: 6: VP1 subsequence for AAV serotype 5, comprising the PLA2 domain and flanking sequence.

SEQ ID NO: 7: VP1 subsequence for AAV serotype 6, comprising the PLA2 domain and flanking sequence.

SEQ ID NO: 8: VP1 subsequence for AAV serotype 7, comprising the PLA2 domain and flanking sequence.

SEQ ID NO: 9: VP1 subsequence for AAV serotype 8, comprising the PLA2 domain and flanking sequence.

SEQ ID NO: 10: VP1 subsequence for AAV serotype 9, comprising the PLA2 domain and flanking sequence.

SEQ ID NO: 11: VP1 subsequence for AAV serotype 10, comprising the PLA2 domain and flanking sequence.

SEQ ID NO: 12: VP1 subsequence for AAV serotype 11, comprising the PLA2 domain and flanking sequence.

SEQ ID NO: 13: VP1 subsequence for AAV serotype 12, comprising the PLA2 domain and flanking sequence.

SEQ ID NO: 14: VP1 subsequence for AAV serotype 13, comprising the PLA2 domain and flanking sequence.

SEQ ID NO: 15: Modified VP1 subsequence for AAV serotype 1, comprising the PLA2 domain and flanking sequence.

SEQ ID NO: 16: Modified VP1 subsequence for AAV serotype 3, comprising the PLA2 domain and flanking sequence.

SEQ ID NO: 17: Modified VP1 subsequence for AAV serotype 4, comprising the PLA2 domain and flanking sequence.

SEQ ID NO: 18: Modified VP1 subsequence for AAV serotype 5, comprising the PLA2 domain and flanking sequence.

SEQ ID NO: 19: Modified VP1 subsequence for AAV serotype 6, comprising the PLA2 domain and flanking sequence.

SEQ ID NO: 20: Modified VP1 subsequence for AAV serotype 7, comprising the PLA2 domain and flanking sequence.

SEQ ID NO: 21: Modified VP1 subsequence for AAV serotype 8, comprising the PLA2 domain and flanking sequence.

SEQ ID NO: 22: Modified VP1 subsequence for AAV serotype 9, comprising the PLA2 domain and flanking sequence.

SEQ ID NO: 23: Modified VP1 subsequence for AAV serotype 10, comprising the PLA2 domain and flanking sequence.

SEQ ID NO: 24: Modified VP1 subsequence for AAV serotype 11, comprising the PLA2 domain and flanking sequence.

SEQ ID NO: 25: Modified VP1 subsequence for AAV serotype 12, comprising the PLA2 domain and flanking sequence.

SEQ ID NO: 26: Modified VP1 subsequence for AAV serotype 13, comprising the PLA2 domain and flanking sequence.

SEQ ID NO: 27: VP1 amino acid sequence for AAV serotype 1.

SEQ ID NO: 28: VP1 amino acid sequence for AAV serotype 2.

SEQ ID NO: 29: VP1 amino acid sequence for AAV serotype 3.

SEQ ID NO: 30: VP1 amino acid sequence for AAV serotype 4.

SEQ ID NO: 31: VP1 amino acid sequence for AAV serotype 5.

SEQ ID NO: 32: VP1 amino acid sequence for AAV serotype 6.

SEQ ID NO: 33: VP1 amino acid sequence for AAV serotype 7.

SEQ ID NO: 34: VP1 amino acid sequence for AAV serotype 8.

SEQ ID NO: 35: VP1 amino acid sequence for AAV serotype 9.

SEQ ID NO: 36: VP1 amino acid sequence for AAV serotype 10.

SEQ ID NO: 37: VP1 amino acid sequence for AAV serotype 11.

SEQ ID NO: 38: VP1 amino acid sequence for AAV serotype 12.

SEQ ID NO: 39: VP1 amino acid sequence for AAV serotype 13.

DETAILED DESCRIPTION

General

Throughout this specification, unless specifically stated otherwise or the context requires otherwise, reference to a single step, feature, composition of matter, group of steps or group of features or compositions of matter shall be taken to encompass one and a plurality (i.e. one or more) of those steps, features, compositions of matter, groups of steps or groups of features or compositions of matter.

Those skilled in the art will appreciate that the present disclosure is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific examples described herein, which are intended for the purpose of exemplification only. Functionally-equivalent products, compositions and methods are clearly within the scope of the present disclosure.

Any example of the present disclosure herein shall be taken to apply mutatis mutandis to any other example of the disclosure unless specifically stated otherwise.

Unless specifically defined otherwise, all technical and scientific terms used herein shall be taken to have the same meaning as commonly understood by one of ordinary skill in the art (for example, in cell culture, molecular genetics, immunology, immunohistochemistry, protein chemistry, and biochemistry).

Unless otherwise indicated, the recombinant DNA, recombinant protein, cell culture, and immunological techniques utilized in the present disclosure are standard procedures, well known to those skilled in the art. Such techniques are described and explained throughout the literature in sources such as, J. Perbal, A Practical Guide to Molecular Cloning, John Wiley and Sons (1984), J. Sambrook et al. Molecular Cloning: A Laboratory Manual, Cold Spring Harbor Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbor Laboratory, (1988), and J. E. Coligan et al. (editors) Current Protocols in Immunology, John Wiley & Sons (including all updates until present).

Throughout this specification, unless the context requires otherwise, the word "comprise", or variations such as "comprises" or "comprising", is understood to imply the inclusion of a stated step or element or integer or group of steps or elements or integers but not the exclusion of any other step or element or integer or group of elements or integers.

The term "and/or", e.g., "X and/or Y" shall be understood to mean either "X and Y" or "X or Y" and shall be taken to provide explicit support for both meanings or for either meaning.

Selected Definitions

As used herein, the term "Adeno-Associated Virus" or "AAV" relates to a group of viruses within the Parvoviridae family which contain a short (approx. 4.7 kb) single-stranded DNA genome and which depend on the presence of a helper virus, such as an Adenovirus for their replication. Also contemplated by the present disclosure are vectors derived from AAV i.e. gene transfer vehicles.

As used herein, the term "serotype", as used in the context of AAV, is a distinction used to refer to an AAV having a capsid that is serologically distinct from other AAV serotypes. Serologic distinctiveness is determined on the basis of the lack of cross-reactivity between antibodies to one AAV as compared to another AAV. Such cross-reactivity differences are usually due to differences in capsid protein sequences/antigenic determinants (e.g., due to VP1, VP2, and/or VP3 sequence differences of AAV serotypes).

As used herein in the context of an AAV, the term "viral capsid protein", "capsid protein", "capsid polypeptide" or similar relates to a polypeptide of the AAV having the activity of self-assembly to produce the proteinaceous shell of an AAV particle, also referred to as coat protein or VP protein. It is comprised of three subunits, VP1, VP2 and VP3, which are typically expressed from a single nucleic acid molecule, and which interact together to form a capsid of an icosahedral symmetry. The capsid structure of AAV is described in BERNARD N. FIELDS et al., VIROLOGY, volume 2, chapters 69 & 70 (4th ed., Lippincott-Raven Publishers).

As used herein, the term "operably-linked" or "operable linkage" (or similar) refers to a linkage of polynucleotide elements in a functional relationship. A nucleic acid or polynucleotide sequence is "operably-linked" when it is placed into a functional relationship with another nucleic acid sequence. For instance, a transcription regulatory sequence e.g., a promoter, enhancer or other expression control element, that is art-recognized, will be operably-linked to a coding sequence if it affects the transcription of that coding sequence.

As used herein, the term "promoter" refers generally to a DNA sequence that is involved in recognition and binding of DNA-dependent RNA polymerase and other proteins (transacting transcription factors) to initiate and control transcription of one or more coding sequences, and is generally located upstream of the coding sequence with respect to the direction of transcription.

As used herein, the term "inverted terminal repeat" or "ITR", in the plural or singular, refers to sequence located at one end of a vector that can form a hairpin structure when used in combination with a complementary sequence that is located at the opposing end of the vector. The pair of inverted terminal repeats is involved in rescue of AAV DNA, replication and packaging in the host genome. The ITRs are also required for efficient encapsidation of the AAV DNA and generation of fully assembled AAV particles.

The term "improved functionality" or similar as used in the context of AAV of the disclosure comprising modified capsid protein or VP1 sequences, shall be understood to mean that the AAV comprising the modified capsid protein or VP1 sequence has an improved endosomal escape activity relative to a wildtype AAV of the same serotype which has not been modified and which is produced in insect cells. As used herein, the term "endosomal escape activity", endosome escape activity", or similar, shall be understood to mean the ability of an AAV to escape from the endosomal compartment following cellular internalisation. In the context of AAV functionality, it will be appreciated that an AAV which is unable to escape from the endosome following cellular internalisation is not functional, particularly in the context of gene therapy.

DNA Constructs for Production of Modified AAV

The present disclosure relates generally to AAV having a modified viral capsid protein, in particular comprising a modified VP1 sequence and associated phospholipase A2 (PLA2) domain, which have improved or restored functionality (relative to the corresponding wildtype AAV) when produced in insect cells. The present disclosure also relates to the production of such modified AAVs and the use of same as vectors for the introduction and/or expression of exogenous nucleic acids in mammalian cells, such as in the case of gene therapy.

AAV normally infects humans (e.g., serotypes 1, 2, 3, 4, 5, 6, 7, 8, 9, 10, 11, 12, 13) or primates (e.g., serotypes 1 and 4). The genomic organization of all known AAV serotypes is very similar. The genome of AAV is a linear, single-stranded DNA molecule that is generally less than about 5,000 nucleotides (nt) in length. Inverted terminal repeats (ITRs) flank the unique coding nucleotide sequences for the non-structural replication (Rep) proteins and the structural (VP) proteins. The VP proteins (VP1, VP2 and VP3) form the capsid. The AAV capsid assembly requires expression of the assembly-activating protein (AAP), which is encoded by an in frame open reading frame of the capsid gene that lies within the coding sequences of the VP2 and VP3 ORFs (Sonntag et al., (2010) PNAS, 107(22):10220-10225). The terminal 145 nt are self-complementary and are organized so that an energetically stable intramolecular duplex forming a T-shaped hairpin may be formed i.e., the inverted terminal repeat (ITR). These hairpin structures function as an origin for viral DNA replication, serving as primers for the cellular DNA polymerase complex. Following infection of wildtype AAV (wtAAV) in mammalian cells, the Rep genes (i.e. Rep78 and Rep52) are expressed from the P5 promoter and the P19 promoter, respectively. The Rep78 protein has a function in the replication of the viral genome, whereas the Rep52 protein mobilizes the nascent genome into the viral particle. A splicing event in the Rep ORF results in the expression of four Rep proteins (i.e. Rep78, Rep68, Rep52 and Rep40). However, it has been shown that the unspliced mRNA, encoding Rep78 and Rep52 proteins, in mammalian cells are sufficient for AAV vector production. Also in insect cells the Rep78 and Rep52 proteins suffice for AAV vector production. The three capsid proteins, VP1, VP2 and VP3 are expressed from a single VP reading frame from the p40 promoter.

Of particular importance to functionality of AAV (particularly those produced in insect cells) is the VP1 subunit, which contains a conserved phospholipase A2 (PLA2) motif, the activity of which has been shown to be required for endosome exit after which the viral genome transfers into the nucleus of the host cell. Although AAV of serotype 2 has been shown to retain PLA2 activity when expressed in insect cells and thereby retain its functionality, AAV of other serotypes have defective PLA2 activity despite the general conservation of this domain across Parvoviridae. This defective PLA2 activity has limited the ability to produce functional AAV, other than serotype 2, in insect cells. A number of approaches have been employed to address this problem to varying effect, including the construction of chimeric AAV2/5 VP1 proteins, wherein the AAV VP1 sequence, or an N-terminal portion thereof containing the PLA2 motif, is replaced with the corresponding sequence of AAV2 VP1 (domain swapping). Also reported is the production of AAV2 VP1-based mosaics resulting in AAV expressing both wildtype and serotype 2 VP1 sequence. Although these approaches have been reported to improve functionality to varying degrees when expressed in insect cells, the baculovirus system to produce AAV vectors in insect cells for use in the clinical setting is still limited. In the present disclosure, a novel approach involving site specific modification to the AAV VP1 sequence is described, which has been shown to improve subsequent functionality of AAV from serotypes other than AAV2 when expressed from a baculovirus system in insect cells. The improved functionality is conferred by the ability of the virion to escape the endosomal compartment.

Accordingly, the present disclosure provides a nucleic acid molecule comprising a polynucleotide sequence encoding an adeno-associated virus (AAV) viral capsid protein, wherein the viral capsid protein comprises a modified subunit 1 (VP1) sequence comprising a serine at position 1, a glutamic acid at position 26, an arginine at position 40, an aspartic acid at position 43, a serine at position 44 and a lysine at position 64, wherein the amino acid positions are defined relative to the sequence set forth in SEQ ID NO: 1, wherein the amino acids at any one or more of positions 1, 26, 40, 43, 44 and 64 are modified relative to a corresponding wildtype sequence, and wherein no additional amino acids other than those at said any one or more positions 1, 26, 40, 43, 44 and 64 are modified relative to the corresponding wildtype sequence.

In one example, the amino acids at any two, three, four, five or six of positions 1, 26, 40, 43, 44 and 64 of the sequence set forth in SEQ ID NO: 1 are modified relative to a corresponding wildtype sequence as described herein.

The polynucleotide sequence encoding the AAV capsid protein may be from any one of the AAVs which normally infects humans, other than serotype 2 (e.g., serotypes 1, 3, 4, 5, 6, 7, 8, 9, 10, 11, 12, 13). In one example, the viral capsid protein is from AAV serotype 1. In one example, the viral capsid protein is from AAV serotype 3. In one example, the viral capsid protein is from AAV serotype 4. In one example, the viral capsid protein is from AAV serotype 5. In one example, the viral capsid protein is from AAV serotype 6. In one example, the viral capsid protein is from AAV serotype 7. In one example, the viral capsid protein is from AAV serotype 8. In one example, the viral capsid protein is from AAV serotype 9. In one example, the viral capsid protein is from AAV serotype 10. In one example, the viral capsid protein is from AAV serotype 11. In one example, the viral capsid protein is from AAV serotype 12. In one example, the viral capsid protein is from AAV serotype 13.

The polynucleotide sequence encoding the AAV capsid protein may encode a modified VP1 comprising a sequence set forth in any one of SEQ ID NOs:15-26. In one example, the viral capsid protein is from AAV1 and the modified VP1 sequence comprises the sequence set forth in SEQ ID NO: 15. In one example, the viral capsid protein is from AAV3 and the modified VP1 sequence comprises the sequence set forth in SEQ ID NO: 16. In one example, the viral capsid protein is from AAV4 and the modified VP1 sequence comprises the sequence set forth in SEQ ID NO: 17. In one example, the viral capsid protein is from AAV5 and the modified VP1 sequence comprises the sequence set forth in SEQ ID NO: 18. In one example, the viral capsid protein is from AAV6 and the modified VP1 sequence comprises the sequence set forth in SEQ ID NO: 19. In one example, the viral capsid protein is from AAV7 and the modified VP1 sequence comprises the sequence set forth in SEQ ID NO: 20. In one example, the viral capsid protein is from AAV8 and the modified VP1 sequence comprises the sequence set forth in SEQ ID NO: 21. In one example, the viral capsid protein is from AAV9 and the modified VP1 sequence comprises the sequence set forth in SEQ ID NO: 22. In one example, the viral capsid protein is from AAV10 and the modified VP1 sequence comprises the sequence set forth in SEQ ID NO: 23. In one example, the viral capsid protein is from AAV11 and the modified VP1 sequence comprises the sequence set forth in SEQ ID NO: 24. In one example, the viral capsid protein is from AAV12 and the modified VP1 sequence comprises the sequence set forth in SEQ ID NO: 25. In one example, the viral capsid protein is from AAV13 and the modified VP1 sequence comprises the sequence set forth in SEQ ID NO: 26.

In each of the foregoing examples, the viral capsid protein may comprise subunit 2 (VP2) and subunit 3 (VP3) sequences from the same AAV serotype as the modified VP1. Preferably the VP1, VP2 and VP3 are expressed from the same ORF.

The nucleotide sequence encoding the AAV viral capsid protein as described herein may be operably-linked to a promoter which is suitable for expression of the capsid protein in an insect cell. Suitable promoters for expression in insect cells are known in the art and contemplated for use herein. In this regard, methodologies for molecular engineering and expression of polypeptides in insect cells have been previously described, for example, in Summers and Smith, A Manual of Methods for Baculovirus Vectors and Insect Culture Procedures, Texas Agricultural Experimental Station Bull. No. 7555, College Station, Tex. (1986); Luckow., In Prokop et al., Cloning and Expression of Heterologous Genes in Insect Cells with Baculovirus Vectors' Recombinant DNA Technology and Applications, 97-152 (1991); King, L. A and R. D. Possee, The baculovirus expression system, Chapman and Hall, United Kingdom (1992); O'Reilly, D. R., L. K. Miller, V. A Luckow, Baculovirus Expression Vectors: A Laboratory Manual, New York (1992); W. H. Freeman and Richardson, C. D., Baculovirus Expression Protocols, Methods in Molecular Biology, volume 39 (1992); U.S. Pat. No. 4,745,051; US2003148506; WO2003/074714; Kotin R M (2011) *Hum. Mol. Genet.,* 20(R1):R2-R6; Aucoin et al., (2006) *Biotechnol. Bioeng.* 95(6):1081-1092; and van Oers et al., (2015) *J. Gen. Virol.* 96:6-23. Promoters and other such regulatory element which are known in the art are clearly contemplated for use in the nucleic acid of the disclosure. In one particular example, the promoter is a polyhedron promoter or a p10 promoter.

As described herein, the AAV capsid assembly requires expression of the non-structural protein, assembly-activating protein (AAP). Accordingly, in each of the foregoing examples, the nucleic acid molecule as described herein may comprise a polynucleotide encoding an AAP.

As described herein, AAV genome comprises Rep genes (i.e. Rep78 and Rep52), the proteins encoded by which function in the replication of the viral genome. A splicing event in the Rep ORF results in the expression of four Rep proteins (i.e. Rep78, Rep68, Rep52 and Rep40). However, it has been shown that the unspliced mRNA, encoding Rep78 and Rep52 proteins, in insect cells is sufficient for AAV vector production. Accordingly, in one example, the nucleic acid molecule of the disclosure also comprises a polynucleotide sequence encoding at least one large AAV replication Rep protein selected from Rep78 and Rep68 and at least one small AAV Rep protein selected from Rep52 and Rep40. In one example, the nucleic acid molecule described herein comprises a polynucleotide sequence encoding Rep78 and Rep52. In one example, the nucleic acid molecule described herein comprises a polynucleotide sequence encoding Rep78 and Rep40. In one example, the nucleic acid molecule described herein comprises a polynucleotide sequence encoding Rep68 and Rep52 from the same AAV serotype as the viral capsid protein. In one example, the nucleic acid molecule described herein comprises a polynucleotide sequence encoding Rep68 and Rep40. In one example, the nucleic acid molecule described herein comprises a polynucleotide sequence encoding Rep78, Rep68, Rep52 and Rep40. In each of the foregoing examples, the respective small and large Rep proteins may be from the same AAV serotype as the viral capsid protein. Alternatively, the respective small and large Rep proteins may be from an AAV serotype other than that of the viral capsid protein e.g., the Rep proteins may be from AAV serotype 2.

The polynucleotide sequences encoding the Rep proteins may be operably-linked to a promoter which is suitable for expression of the Rep proteins in an insect cell. Suitable promoters for expression in insect cells are known in the art and contemplated for use herein. In one particular example, the promoter may be a polyhedron promoter or a p10 promoter. The nucleotide sequences encoding the respective Rep proteins may be operably-linked to the same promoter. Alternatively, each sequence encoding a Rep protein may operably-linked to its own promoter.

Nucleic acids encoding the modified VP1 sequences may be designed in silico e.g., based on wildtype AAV sequences or naturally occurring variant AAV sequences derived from wildtype AAV sequences, and DNA constructs comprising the nucleic acid sequence may synthesized using methods known in the art. Alternatively, or in addition, modifications to the VP1 sequence relative to the corresponding wild-type VP1 sequence as described herein (or naturally occurring variant AAV sequences derived from those wildtype AAV sequences) may be achieved by application of well-known genetic engineering techniques such as described e.g. in Sambrook and Russell (2001) "Molecular Cloning: A Laboratory Manual (3rd edition), Cold Spring Harbor Laboratory, Cold Spring Harbor Laboratory Press, New York. Various further modifications of VP coding sequence are known to the skilled artisan which could either increase yield of VP and virion or have other desired effects, such as altered tropism or reduce antigenicity of the virion. These modifications are within the scope of the present disclosure.

AAV sequences that may be used in the present disclosure e.g., for the production of AAV with modified VP1 sequences in insect cells as described herein, can be derived from the genome of any AAV serotype. Generally, AAV serotypes have genomic sequences of significant homology at the amino acid and the nucleic acid levels, provide an identical set of genetic functions, produce virions which are physically and functionally similar, and replicate and assemble by practically identical mechanisms (with the specific exemption of the activity of the PLA2 domain described herein). Suitable nucleic acid and protein sequences for AAV for use in the design and production of the modified AAVs of the present disclosure are publically available. VP1 sequences for wildtype AAVs known to infect humans (and which are contemplated herein) are described in Chen et al., (2013) *J. Vir.* 87(11):6391-6405. Human or simian adeno-associated virus (AAV) serotypes are preferred sources of AAV nucleotide sequences for use in the context of the present disclosure, and more preferably AAV serotypes which normally infects humans (e.g., serotypes 1, 2, 3, 4, 5, 6, 7, 8, 9, 10, 11, 12 and 13). Capsid polypeptide sequences for AAV serotypes 1-13 are known in the art, for example, AAV1 (Genbank Acc. No:

AAD27757.1, GI:4689097), AAV2 (Genbank Acc. No: AAC03780.1, GP.2906023), AAV3 (Genbank Acc. No: AAC55049.1, GI: 1408469), AAV4 (Genbank Acc. No: AAC58045.1, GL2337940), AAV5 (Genbank Acc. No: AAD13756.1, GI-4249658), AAV10 (Genbank Acc. No: AAT46337.1, GL48728343), AAV11 (Genbank Acc. No: AAT46339.1, GI:48728346), AAV12 (Genbank Acc. No: ABI16639.1, GI: 112379656), or AAV13 (Genbank Acc. No: ABZ10812.1, GI: 167047087). The polypeptide sequences for AAV capsid proteins for serotypes 1-13 are also set forth in SEQ ID NO: 27-39 herein. Furthermore, the complete genomes for AAV from serotypes 1-13 are known in the art, for example, AAV1 (NCBI Reference Sequence NC_002077.1), AAV2 (GenBank Acc. No: J01901.1), AAV3 (Genbank Acc. No: AF028705.1), AAV4 (NCBI Reference Sequence: NC_001829.1), AAV5 (NCBI Reference Sequence: NC_006152.1), AAV6 (GenBank: AF028704.1), AAV7 (NCBI Reference Sequence: NC_006260.1), AAV8 (NCBI Reference Sequence: NC_006261.1), AAV9 (GenBank Acc. No: AY530579.1), AAV10 (Genbank Acc. No: AY631965.1), AAV11 (Genbank Acc. No: AY631966.1) or AAV12 (Genbank Acc. No: DQ813647.1), or AAV13 (Genbank Acc. No: EU285562.1).

The present disclosure also provides an AAV capsid protein comprising the modified VP1 sequence encoded by the nucleic acid of the disclosure.

Baculovirus Vectors for Production of Modified AAV

The present disclosure also provides the nucleic acid molecule of the disclosure in an insect cell-compatible vector i.e., a baculovirus vector. In particular, the present disclosure provides a baculovirus vector comprising the nucleic acid molecule encoding AAV viral capsid protein with the modified VP1 sequence as described herein.

The present disclosure also provides a plurality of baculovirus vectors comprising:

(i) a first baculovirus vector comprising the nucleic acid molecule encoding AAV viral capsid protein with the modified VP1 sequence as described herein; and (ii) a second baculovirus vector comprising a polynucleotide encoding a protein or RNA of interest flanked by AAV inverted terminal repeat (ITR) sequences.

In one example, the AAV ITR sequences are from the same serotype as the viral capsid protein encoded by the nucleic acid molecule within the first baculovirus vector. In another example, the AAV ITR sequences are from another AAV serotype e.g., AAV2.

Typically, the polynucleotide encoding the protein or RNA of interest, inclusive of the flanking ITRs, is 5,000 nucleotides (nt) or less in length. However, polynucleotide encoding oversized DNA, i.e. more than 5,000 nt in length, are also contemplated. An oversized DNA is herein understood as a DNA exceeding the maximum AAV packaging limit of 5 kbp. Therefore, the generation of AAV vectors able to produce recombinant proteins or RNAs that are usually encoded by larger genomes than 5.0 kb may also be feasible.

The polynucleotide encoding the protein or RNA of interest for expression in a mammalian cell will be located within the baculovirus vector such that it will be replicated and incorporated into an AAV genome replicated in the insect cell. Any nucleotide sequence can be incorporated for later expression in a mammalian cell transfected with the AAV produced in accordance with the present disclosure, as long as the constructs remain within the packaging capacity of the AAV virion. The polynucleotide sequence may, for example, encode a protein of interest or it may express an RNAi agent i.e., an RNA molecule that is capable of RNA interference such as e.g., a shRNA (short hairpin RNA) or a short hairpin micro RNA (shmiR). In one example, the polynucleotide encoding a protein or RNA of interest encodes a plurality of proteins of interest, a plurality of RNAi agents, or one or more proteins of interest and one or more RNAi agents. The protein of interest for expression in a mammalian cell may be a therapeutic gene product. A therapeutic gene product can be a polypeptide, or an RNA molecule (such as a shRNA or shmiR as described herein), or other gene product that, when expressed in a target cell, provides a desired therapeutic effect such as e.g., ablation of an undesired activity e.g., the ablation of an infected cell, or the complementation of a genetic defect e.g., causing a deficiency in an enzymatic activity. Alternatively, or in addition, the protein of interest encoded by the polynucleotide may serve as marker proteins to assess cell transformation and expression. Suitable marker proteins for this purpose are e.g., the fluorescent protein GFP or firefly luciferase. Sources for obtaining these marker genes and methods for their use are provided in Sambrook and Russel (2001) "Molecular Cloning: A Laboratory Manual (3rd edition), Cold Spring Harbor Laboratory, Cold Spring Harbor Laboratory Press, New York.

In accordance with an example in which the first baculovirus vector does not encode AAV Rep proteins, the plurality of baculovirus vectors further comprises:

(iii) a third baculovirus vector comprising a polynucleotide sequence encoding at least one large AAV Rep protein selected from Rep78 and Rep68 and at least one small AAV Rep protein selected from Rep52 and Rep40.

For example, the third baculovirus vector may comprise a polynucleotide sequence encoding Rep78 and Rep52. For example, the third baculovirus vector may comprise a polynucleotide sequence encoding Rep78 and Rep40. For example, the third baculovirus vector may comprise a polynucleotide sequence encoding Rep68 and Rep52. For example, the third baculovirus vector may comprise a polynucleotide sequence encoding Rep68 and Rep40. For example, the third baculovirus vector may comprise a polynucleotide sequence encoding Rep78, Rep68, Rep52 and Rep40. In each of the foregoing examples describing the third baculovirus vector, the respective small and large Rep proteins may be from the same AAV serotype as the viral capsid protein encoded by the first baculovirus vector. Alternatively, the respective small and large Rep proteins may be from an AAV serotype other than that of the viral capsid protein encoded by the first baculovirus vector e.g., the Rep proteins may be from AAV serotype 2. In this regard, Rep sequences are particularly conserved among most serotypes and it has been reported that Rep sequences efficiently cross-complement in insect cells.

In each of the foregoing examples describing the plurality of baculovirus vectors, the polynucleotide sequence encoding the Rep proteins within the third baculovirus vector may be operably-linked to a promoter for expression of the Rep proteins in an insect cell. Suitable promoters for expression of proteins in insect cells have been described and shall be taken to apply mutatis mutandis to examples of the disclosure describing baculovirus vectors unless specifically stated otherwise.

At least one of the baculovirus vectors in the plurality will comprise a polynucleotide encoding the assembly-activating protein (AAP) as required for the AAV capsid assembly. In one example, the baculovirus vector encoding the capsid protein comprises a polynucleotide encoding an AAP. In alternative example, the baculovirus encoding the Rep proteins and/or the baculovirus encoding the protein or RNA of interest, comprises a polynucleotide encoding an AAP.

Baculoviral vectors and methods for their production and use are known in the art and described in the above cited references on molecular engineering of insect cells.

Insect Cells

Also provided herein is an insect cell comprising a nucleic acid molecule of the disclosure encoding an AAV viral capsid protein with the modified VP1 sequence as described herein.

The insect cell will also preferably comprise (i) a polynucleotide sequence encoding at least one large AAV Rep protein selected from Rep78 and Rep68 and at least one small AAV Rep protein selected from Rep52 and Rep40, and (ii) a polynucleotide encoding a protein or RNA of interest flanked by AAV ITR sequences. Specific combinations of large and small Rep proteins, as well as suitable ITRs, have been described herein e.g., in the context of baculovirus vectors of the disclosure, and shall be taken to apply mutatis mutandis to examples of the disclosure describing insect cells unless specifically stated otherwise. Likewise, polynucleotides encoding proteins or RNAs of interest for incorporation into the genome of an AAV produced by the insect cell have been described herein e.g., in the context of the baculovirus vectors of the disclosure, and shall be taken to apply mutatis mutandis to examples of the disclosure describing insect cells unless specifically stated otherwise.

Preferably, each of (i) the nucleic acid molecule of the disclosure encoding an AAV viral capsid protein with the modified VP1 sequence as described herein, (ii) the polynucleotide encoding the Rep proteins, and (iii) the polynucleotide encoding the protein or RNA of interest flanked by AAV ITR sequences, are introduced into a baculovirus vector and used to infect the insect cell. Preferably, at least one of (i) to (iii) will also comprise a polynucleotide encoding the assembly-activating protein (AAP) AAV capsid assembly. Thus, the insect cell described herein shall comprise the components necessary to enable expression and assembly of AAV virion which are infective and stable. In one example, the insect cells may comprise episomally replicating recombinant baculoviruses.

The present disclosure also provides an insect cell comprising a baculovirus vector or plurality of baculovirus vectors as described herein which is capable of producing AAV virion which are infective and stable. In one example, the insect cell has been transformed or transfected with the baculovirus vector or plurality of baculovirus vectors as described herein. In accordance with an example in which the insect cell has been transformed or transfected with the baculovirus vector or plurality of baculovirus vectors of the disclosure, each of (i) the nucleic acid molecule of the disclosure encoding an AAV viral capsid protein with the modified VP1 sequence as described herein, (ii) the polynucleotide encoding the Rep proteins, and (iii) the polynucleotide encoding the protein or RNA of interest flanked by AAV ITR sequences, will be expressed from episomally replicating recombinant baculovirus genomes.

Any insect cell which allows for replication of baculovirus and which can be maintained in culture can be used in accordance with the present disclosure. For example, the cell line used can be from Spodoptera frupperda, Drosophila cell lines, or mosquito cell lines e.g., Aedes albopictus derived cell lines. Preferred insect cells or cell lines are cells from the insect species which are susceptible to baculovirus infection, including e.g., expresSF+®, Drosophila Schneider 2 (S2) cells, Se301, SeIZD2109, SeUCR1, Sf9, SP900+, Sf21, BTI-TN-5B1-4, MG-I, 5 Tn368, HzAm1, Ha2302, and Hz2E5.

Methods of Producing Modified AAVs

The present disclosure also provides a method of producing an AAV comprising a capsid protein with a modified VP1 sequence in which the nucleic acid encoding the modified VP1 sequence as described herein is expressed within an insect cell and an AAV is assembled therein. In one example, the present disclosure provides a method for producing AAV in an insect cell comprising:

(i) culturing an insect cell as described herein in culture media under conditions sufficient for the cells to produce AAV; and optionally (ii) recovering the AAV from the culture media and/or cells.

In another example, the present disclosure provides a method for producing AAV in an insect cell comprising:

(i) co-infecting an insect cell with: a first baculovirus vector having a genome comprising the nucleic acid molecule of the disclosure encoding an AAV viral capsid protein with the modified VP1 sequence described herein, and comprising a polynucleotide sequence encoding at least one large AAV replication (Rep) protein selected from Rep78 and Rep68 and at least one small AAV Rep protein selected from Rep52 and Rep40; and a second baculovirus vector having a genome comprising a polynucleotide encoding a protein or RNA of interest flanked by AAV inverted terminal repeat (ITR) sequences as described herein;

(ii) culturing the insect cell infected with the baculovirus vectors at (i) in culture media under conditions sufficient for the cells to produce AAV; and optionally (iii) recovering the AAV from the culture media and/or cells.

In another example, the present disclosure provides a method for producing AAV in an insect cell comprising:

(i) co-infecting an insect cell with: a first baculovirus vector having a genome comprising the nucleic acid molecule of the disclosure encoding an AAV viral capsid protein with the modified VP1 sequence as described herein; a second baculovirus vector having a genome comprising a polynucleotide sequence encoding at least one large AAV replication (Rep) protein selected from Rep78 and Rep68 and at least one small AAV Rep protein selected from Rep52 and Rep40; and a third baculovirus vector having a genome comprising a polynucleotide encoding a protein or RNA of interest flanked by AAV ITR sequences;

(ii) culturing the insect cell infected with the baculovirus vectors at (i) in culture media under conditions sufficient for the cells to produce AAV; and optionally (iii) recovering the AAV from the culture media or cells.

In each of the foregoing examples, the Rep proteins may be from the same AAV serotype as the viral capsid protein. Alternatively, the Rep proteins may be from a different AAV serotype to that of the viral capsid protein e.g., the Rep proteins may be from AAV serotype 2.

Similarly, in each of the foregoing examples, the ITR sequences may be from the same AAV serotype as the viral capsid protein. Alternatively, the ITR sequences may be from a different AAV serotype to that of the viral capsid protein e.g., the ITR sequences may be from AAV serotype 2.

At least one of the baculovirus vectors in the plurality will also comprise a polynucleotide encoding the assembly-activating protein (AAP) for AAV capsid assembly. In one example, the baculovirus vector encoding the capsid protein comprises a polynucleotide encoding an AAP. In an alternative example, the baculovirus encoding the Rep proteins and/or the baculovirus encoding the protein or RNA of interest, comprises a polynucleotide encoding an AAP.

In accordance with examples in which the method comprises infecting insect cells with baculovirus vectors described herein, any conventional method known in the art may be employed. Suitable culture media and conditions for the production of virus, such as AAV, in insect cell are known in art and are contemplated herein. For example, methodology for molecular engineering and expression of AAV and polypeptides in insect cells is described, for example, in Summers and Smith, A Manual of Methods for Baculovirus Vectors and Insect Culture Procedures, Texas Agricultural Experimental Station Bull. No. 7555, College Station, Tex. (1986); Luckow., In Prokop et al., Cloning and Expression of Heterologous Genes in Insect Cells with Baculovirus Vectors' Recombinant DNA Technology and Applications, 97-152 (1991); King, L. A and R. D. Possee, The baculovirus expression system, Chapman and Hall, United Kingdom (1992); O'Reilly, D. R., L. K. Miller, V. A Luckow, Baculovirus Expression Vectors: A Laboratory Manual, New York (1992); W. H. Freeman and Richardson, C. D., Baculovirus Expression Protocols, Methods in Molecular Biology, volume 39 (1992); U.S. Pat. No. 4,745, 051; US2003148506; WO2003/074714; Kotin R M (2011) *Hum. Mol. Genet.*, 20(R1):R2-R6; Aucoin et al., (2006) *Biotechnol. Bioeng.* 95(6):1081-1092; and van Oers et al., (2015) *J. Gen. Virol.* 96:6-23.

Suitable large and small Rep proteins, ITR sequences, and proteins or RNAs of interest, have been described herein e.g., in the context of baculovirus vectors of the disclosure, and shall be taken to apply mutatis mutandis to examples of the disclosure describing methods of producing AAV unless specifically stated otherwise. In one example, the methods described herein comprise co-transfecting the insect cell with the plurality of baculovirus vectors of the disclosure.

In each of the foregoing examples describing methods of producing AAV, the polynucleotide sequence encoding the Rep proteins within the baculovirus vector may be operably-linked to a promoter (and optionally other regulatory elements) for expression of the Rep proteins in an insect cell. Likewise, the polynucleotide sequence encoding the protein or RNA of interest flanked by AAV ITR sequences may be operably-linked to a promoter (and optionally other regulatory elements) for expression in an insect cell. Suitable promoters for expression in insect cells are known in the art and have been described herein and shall be taken to apply mutatis mutandis to examples of the disclosure describing methods of producing AAV unless specifically stated otherwise. In one example, the promoter is a polyhedron promoter or a p10 promoter.

In one example, the method of producing the AAV comprises the step of recovering the AAV from the culture media and/or cells. In another example, the method of producing the AAV comprises the steps of recovering the AAV from the culture media and/or cells and then purifying the AAV. In one example, the AAV are recovered from the cells. In one example, the AAV are recovered from the culture media. In one example, the AAV are recovered from the cell and culture media. Suitable methods for recovery and purification of AAV from culture media and/or cells are known in the art and contemplated for use herein. For example, the method may comprise iodixanol-based density gradient purification followed by Cesium Chloride (CsCl) gradient centrifugation. For example, the method may comprise affinity-purification of the AAV using an anti-AAV antibody, preferably an immobilized antibody. The anti-AAV antibody may be an monoclonal antibody. A particularly suitable antibody is a single chain camelid antibody or a fragment thereof as e.g. obtainable from camels or llamas (see e.g. Muyldermans et al., (2001) *Biotechnol.* 74: 277-302). The antibody for affinity-purification of AAV is preferably one that specifically binds an epitope on a AAV capsid protein, such as an epitope that is present on capsid protein of more than one AAV serotype (to enable purification of AAV from different serotypes).

The construction and purification of recombinant AAV has been described previously. See, e.g., U.S. Pat. Nos. 5,173,414, 5,139,941, 5,863,541, and 5,869,305, 6,057,152, 6,376,237; Rabinowitz et al., (2002) *J. Virol.* 76:791-801; and Bowles et al., (2003) *J. Virol.* 77:423-432. Such methods as have been described are contemplated for use herein.

The present disclosure also provides an AAV comprising a viral capsid protein with a modified VP1 sequence which is produced by a method described herein.

The present disclosure also provides a method of improving functionality of an AAV from a serotype other than serotype 2 which is produced in an insect cell, the method comprising modifying a VP1 sequence of an AAV viral capsid protein relative to the corresponding wildtype sequence by substituting one or more amino acids at position 1, 26, 40, 43, 44 and 64 such that the viral capsid protein comprises one or more of a serine at position 1, a glutamic acid at position 26, an arginine at position 40, an aspartic acid at position 43, a serine at position 44 and/or a lysine at position 64, wherein the residue positions are determined relative to the sequence set forth in SEQ ID NO: 1, wherein no additional amino acids other than those at positions 1, 26, 40, 43, 44 and/or 64 are modified relative to the corresponding wildtype sequence, and wherein the AAV has improved functionality when produced in insect cells relative to the corresponding wildtype AAV which has not been modified when produced in insect cells. The improved functionality of the AAV will be due to an ability of the AAV to escape the endosomal compartment following cellular internalization. AAV viral capsid proteins comprising modified VP1 sequences have been described herein, and any example thereof shall be taken to apply mutatis mutandis to the method of improving functionality of an AAV as described herein unless specifically stated otherwise.

In one example, the method of improving functionality of an AAV comprises modifying any two or more of the amino acids at positions 1, 26, 40, 43, 44 and 64 of the VP1 sequence relative to a corresponding wildtype sequence as described herein, such that the viral capsid protein comprises two or more of a serine at position 1, a glutamic acid at position 26, an arginine at position 40, an aspartic acid at position 43, a serine at position 44 and/or a lysine at position 64, wherein the residue positions are determined relative to the sequence set forth in SEQ ID NO: 1. In one example, the method of improving functionality of an AAV comprises modifying any three or more of the amino acids at positions 1, 26, 40, 43, 44 and 64 of the VP1 sequence relative to a corresponding wildtype sequence as described herein, such that the viral capsid protein comprises three or more of a serine at position 1, a glutamic acid at position 26, an arginine at position 40, an aspartic acid at position 43, a serine at position 44 and/or a lysine at position 64, wherein the residue positions are determined relative to the sequence set forth in SEQ ID NO: 1. In one example, the method of improving functionality of an AAV comprises modifying any four or more of the amino acids at positions 1, 26, 40, 43, 44 and 64 of the VP1 sequence relative to a corresponding wildtype sequence as described herein, such that the viral capsid protein comprises four or more of a serine at position 1, a glutamic acid at position 26, an arginine at position 40, an aspartic acid at position 43, a serine at position 44 and/or a lysine at position 64, wherein the residue positions are determined relative to the sequence set forth in SEQ ID NO: 1. In one example, the method of improving functionality of an AAV comprises modifying any five or more of the amino acids at positions 1, 26, 40, 43, 44 and 64 of the VP1 sequence relative to a corresponding wildtype sequence as described herein, such that the viral capsid protein comprises five or more of a serine at position 1, a glutamic acid at position 26, an arginine at position 40, an aspartic acid at position 43, a serine at position 44 and/or a lysine at position 64, wherein the residue positions are determined relative to the sequence set forth in SEQ ID NO: 1. In one example, the method of improving functionality of an AAV comprises modifying each of the amino acids at positions 1, 26, 40, 43, 44 and 64 of the VP1 sequence relative to a corresponding wildtype sequence as described herein, such that the viral capsid protein comprises a serine at position 1, a glutamic acid at position 26, an arginine at position 40, an aspartic acid at position 43, a serine at position 44 and a lysine at position 64, wherein the residue positions are determined relative to the sequence set forth in SEQ ID NO: 1.

The method of the present disclosure may provide an AAV with a viral capsid protein having a VP1 sequence comprising the sequence set forth in any one of SEQ ID NOs: 15-26. The AAV may be from any serotype which normally infects humans (e.g., serotypes 1, 2, 3, 4, 5, 6, 7, 8, 9, 10, 11, 12, 13).

In one example, the method comprises modifying the VP1 sequence of a viral capsid protein of AAV relative to the corresponding wildtype sequence, such that:

(i) when the AAV is of serotype 1, the viral capsid protein includes a VP1 sequence comprising the sequence set forth in SEQ ID NO: 15;

(ii) when the AAV is of serotype 3, the viral capsid protein includes a VP1 sequence comprising the sequence set forth in SEQ ID NO: 16;

(iii) when the AAV is of serotype 4, the viral capsid protein includes a VP1 sequence comprising the sequence set forth in SEQ ID NO: 17;

(iv) when the AAV is of serotype 5, the viral capsid protein includes a VP1 sequence comprising the sequence set forth in SEQ ID NO: 18;

(v) when the AAV is of serotype 6, the viral capsid protein includes a VP1 sequence comprising the sequence set forth in SEQ ID NO: 19;

(vi) when the AAV is of serotype 7, the viral capsid protein includes a VP1 sequence comprising the sequence set forth in SEQ ID NO: 20;

(vii) when the AAV is of serotype 8, the viral capsid protein includes a VP1 sequence comprising the sequence set forth in SEQ ID NO: 21;

(viii) when the AAV is of serotype 9, the viral capsid protein includes a VP1 sequence comprising the sequence set forth in SEQ ID NO: 22;

(ix) when the AAV is of serotype 10, the viral capsid protein includes a VP1 sequence comprising the sequence set forth in SEQ ID NO: 23;

(x) when the AAV is of serotype 11, the viral capsid protein includes a VP1 sequence comprising the sequence set forth in SEQ ID NO: 24;

(xi) when the AAV is of serotype 12, the viral capsid protein includes a VP1 sequence comprising the sequence set forth in SEQ ID NO: 25; and (xii) when the AAV is of serotype 13, the viral capsid protein includes a VP1 sequence comprising the sequence set forth in SEQ ID NO: 26.

In one example, the method comprises modifying the VP1 sequence of a viral capsid protein of AAV1 relative to the corresponding wildtype sequence, such that the viral capsid protein includes a VP1 sequence comprising the sequence set forth in SEQ ID NO: 15. In one example, the method comprises modifying the VP1 sequence of a viral capsid protein of AAV3 relative to the corresponding wildtype sequence, such that the viral capsid protein includes a VP1 sequence comprising the sequence set forth in SEQ ID NO: 16. In one example, the method comprises modifying the VP1 sequence of a viral capsid protein of AAV4 relative to the corresponding wildtype sequence, such that the viral capsid protein includes a VP1 sequence comprising the sequence set forth in SEQ ID NO: 17. In one example, the method comprises modifying the VP1 sequence of a viral capsid protein of AAV5 relative to the corresponding wildtype sequence, such that the viral capsid protein includes a VP1 sequence comprising the sequence set forth in SEQ ID NO: 18. In one example, the method comprises modifying the VP1 sequence of a viral capsid protein of AAV6 relative to the corresponding wildtype sequence, such that the viral capsid protein includes a VP1 sequence comprising the sequence set forth in SEQ ID NO: 19. In one example, the method comprises modifying the VP1 sequence of a viral capsid protein of AAV7 relative to the corresponding wildtype sequence, such that the viral capsid protein includes a VP1 sequence comprising the sequence set forth in SEQ ID NO: 20. In one example, the method comprises modifying the VP1 sequence of a viral capsid protein of AAV8 relative to the corresponding wildtype sequence, such that the viral capsid protein includes a VP1 sequence comprising the sequence set forth in SEQ ID NO: 21. In one example, the method comprises modifying the VP1 sequence of a viral capsid protein of AAV9 relative to the corresponding wildtype sequence, such that the viral capsid protein includes a VP1 sequence comprising the sequence set forth in SEQ ID NO: 22. In one example, the method comprises modifying the VP1 sequence of a viral capsid protein of AAV10 relative to the corresponding wildtype sequence, such that the viral capsid protein includes a VP1 sequence comprising the sequence set forth in SEQ ID NO: 23. In one example, the method comprises modifying the VP1 sequence of a viral capsid protein of AAV11 relative to the corresponding wildtype sequence, such that the viral capsid protein includes a VP1 sequence comprising the sequence set forth in SEQ ID NO: 24. In one example, the method comprises modifying the VP1 sequence of a viral capsid protein of AAV12 relative to the corresponding wildtype sequence, such that the viral capsid protein includes a VP1 sequence comprising the sequence set forth in SEQ ID NO: 25. In one example, the method comprises modifying the VP1 sequence of a viral capsid protein of AAV13 relative to the corresponding wildtype sequence, such that the viral capsid protein includes a VP1 sequence comprising the sequence set forth in SEQ ID NO: 26.

The method of improving functionality of an AAV as described herein may further comprise the step of analysing functionality of a modified AAV relative to the corresponding wildtype AAV. That is, the method may further comprise infecting mammalian cells with the modified or wildtype AAVs as described herein and/or produced by the method described herein and determining the level of functionality. For example, functionality of the AAV may be determined by determining the level of expression of the protein or RNA of interest in the mammalian cell following infection with the AAV. Functional assays for determining functionality of virion are known in the art and contemplated for use herein e.g., such as described in Girod et al., (2002) *J. Gen. Viral.*, 83:973-978; Lock et al., (2010) Hum. Gene Ther. 21(10): 1273-1285. Suitable assays for assaying viral infectivity and/or functionality include, but are not limited to: (1) capsid titer by A20 enzyme-linked immunosorbent assay; (2) vector genome titer by quantitative polymerase chain reaction (qPCR); and (3) infectious titer by median tissue culture infective dose (TCID$_{50}$) with qPCR readout and (4) by assaying transduction with a reporter gene, e.g., green fluorescent protein [GFP].

The method of improving functionality of an AAV as described herein may comprise providing a nucleic acid encoding a modified AAV VP1 sequence as described herein or a baculovirus vector comprising same as described herein. Alternatively, or in addition, the method of improving functionality of an AAV as described herein may comprise producing an AAV comprising a capsid protein with a modified VP1 sequence as described herein.

AAV with Modified VP1

The present disclosure also provides an AAV comprising a viral capsid protein with a modified VP1 sequence, said modified VP1 sequence comprising a serine at position 1, a glutamic acid at position 26, an arginine at position 40, an aspartic acid at position 43, a serine at position 44 and a lysine at position 64, wherein the amino acid positions are defined relative to the sequence set forth in SEQ ID NO: 1, wherein the amino acids at any one or more of positions 1, 26, 40, 43, 44 and 64 are modified relative to a corresponding wildtype sequence, and wherein no additional amino acids other than those at sai any one or more positions 1, 26, 40, 43, 44 and 64 are modified relative to the corresponding wildtype sequence.

In one example, the AAV described herein comprises a viral capsid protein with a modified VP1 sequence, wherein the amino acids at any two, three, four, five or six of positions 1, 26, 40, 43, 44 and 64 of the sequence set forth in SEQ ID NO: 1 are modified relative to a corresponding wildtype sequence as described herein.

In one example, the AAV described herein comprises a viral capsid protein with a modified VP1 sequence, wherein the amino acids at any two or more of positions 1, 26, 40, 43, 44 and 64 of the sequence set forth in SEQ ID NO: 1 are modified relative to a corresponding wildtype sequence as described herein.

In one example, the AAV described herein comprises a viral capsid protein with a modified VP1 sequence, wherein the amino acids at any three or more of positions 1, 26, 40, 43, 44 and 64 of the sequence set forth in SEQ ID NO: 1 are modified relative to a corresponding wildtype sequence as described herein.

In one example, the AAV described herein comprises a viral capsid protein with a modified VP1 sequence, wherein the amino acids at any four or more of positions 1, 26, 40, 43, 44 and 64 of the sequence set forth in SEQ ID NO: 1 are modified relative to a corresponding wildtype sequence as described herein.

In one example, the AAV described herein comprises a viral capsid protein with a modified VP1 sequence, wherein the amino acids at any five or more of positions 1, 26, 40, 43, 44 and 64 of the sequence set forth in SEQ ID NO: 1 are modified relative to a corresponding wildtype sequence as described herein.

In one example, the AAV described herein comprises a viral capsid protein with a modified VP1 sequence, wherein the amino acids at each of positions 1, 26, 40, 43, 44 and 64 of the sequence set forth in SEQ ID NO: 1 are modified relative to a corresponding wildtype sequence as described herein.

A viral capsid protein comprising a modified VP1 sequence has been described herein, and any example thereof shall be taken to apply mutatis mutandis to the AAVs of the disclosure comprising said modified VP1 sequence unless specifically stated otherwise.

The AAV described herein may be any one of the AAVs which normally infects humans, other than serotype 2 (e.g., serotypes 1, 3, 4, 5, 6, 7, 8, 9, 10, 11, 12, 13). In one example, the AAV is of serotype 1. In one example, the AAV is of serotype 3. In one example, the AAV is of serotype 4. In one example, the AAV is of serotype 5. In one example, the AAV is of serotype 6. In one example, the AAV is of serotype 7. In one example, the AAV is of serotype 8. In one example, the AAV is of serotype 9. In one example, the AAV is of serotype 10. In one example, the AAV is of serotype 11. In one example, the AAV is of serotype 12. In one example, the AAV is of serotype 13.

The AAV described herein may comprise a capsid protein with modified VP1 comprising a sequence set forth in any one of SEQ ID NOs:15-26. In one example, the AAV is of serotype 1 and the modified VP1 sequence comprises the sequence set forth in SEQ ID NO: 15. In one example, the AAV is of serotype 3 and the modified VP1 sequence comprises the sequence set forth in SEQ ID NO: 16. In one example, the AAV is of serotype 4 and the modified VP1 sequence comprises the sequence set forth in SEQ ID NO: 17. In one example, the AAV is of serotype 5 and the modified VP1 sequence comprises the sequence set forth in SEQ ID NO: 18. In one example, the AAV is of serotype 6 and the modified VP1 sequence comprises the sequence set forth in SEQ ID NO: 19. In one example, the AAV is of serotype 7 and the modified VP1 sequence comprises the sequence set forth in SEQ ID NO: 20. In one example, the AAV is of serotype 8 and the modified VP1 sequence comprises the sequence set forth in SEQ ID NO: 21. In one example, the AAV is of serotype 9 and the modified VP1 sequence comprises the sequence set forth in SEQ ID NO: 22. In one example, the AAV is of serotype 10 and the modified VP1 sequence comprises the sequence set forth in SEQ ID NO: 23. In one example, the AAV is of serotype 11 and the modified VP1 sequence comprises the sequence set forth in SEQ ID NO: 24. In one example, the AAV is of serotype 12 and the modified VP1 sequence comprises the sequence set forth in SEQ ID NO: 25. In one example, the AAV is of serotype 13 and the modified VP1 sequence comprises the sequence set forth in SEQ ID NO: 26.

In each of the foregoing examples, the AAV described herein comprises a viral capsid protein comprising a subunit 2 (VP2) and subunit 3 (VP3) sequences from the same AAV serotype as the modified VP1. Preferably the VP1, VP1 and VP3 are expressed from the same ORF.

As described herein, AAV genome comprises replication (Rep) genes which are the proteins encoded by the virus which function in the replication of the viral genome. Accordingly, in one example, the AAV described herein comprises at least one large AAV Rep protein selected from Rep78 and Rep68 and at least one small AAV Rep protein selected from Rep52 and Rep40. In one example, the AAV described herein comprises Rep78 and Rep52. In one example, the AAV described herein comprises Rep78 and Rep40. In one example, the AAV described herein comprises Rep68 and Rep52. In one example, the AAV described herein comprises Rep68 and Rep40. In one example, the AAV described herein comprises Rep78, Rep68, Rep52 and Rep40. In each of the foregoing examples, the respective small and large Rep proteins may be from the same AAV serotype as the viral capsid protein. Alternatively, the respective small and large Rep proteins may be from an AAV serotype other than that of the viral capsid protein e.g., the Rep proteins may be from AAV2.

The AAV of the disclosure may also comprise a polynucleotide encoding a protein or RNA of interest flanked by AAV inverted terminal repeat (ITR) sequences.

In one example, the AAV ITR sequences are from the same serotype as the viral capsid protein. In another example, the AAV ITR sequences are from a serotype other than that of the viral capsid protein. In one particular example, the ITR sequences are from AAV serotype 2.

As described hereinabove, the polynucleotide encoding the protein or RNA of interest, inclusive of the flanking ITRs, is typically 5,000 nucleotides (nt) or less in length. However, polynucleotide encoding oversized DNA, i.e. more than 5,000 nt in length, are also contemplated. An oversized DNA is herein understood as a DNA exceeding the maximum AAV packaging limit of 5 kbp. Thus, an AAV of the disclosure may be capable of expressing proteins or RNAs from a genome larger than 5.0 kb.

The AAV of the disclosure will preferably comprise a polynucleotide encoding a protein or RNA of interest for expression in a mammalian cell, which is incorporated into its genome. Any nucleotide sequence can be incorporated for later expression in a mammalian cell transfected with the AAV produced in accordance with the present disclosure, as long as the constructs remain within the packaging capacity of the AAV virion. Suitable polynucleotides encoding proteins or RNAs of interest are already described herein and shall be taken to apply mutatis mutandis to the AAVs of the disclosure unless specifically stated otherwise. In one example, the AAV genome comprises a polynucleotide sequence encoding a therapeutic protein of interest as described herein. In one example, the AAV genome comprises a polynucleotide sequence encoding an RNAi agent as described herein. In one example, the AAV genome comprises a polynucleotide sequence encoding a marker protein e.g., to assess cell transformation and expression, as described herein. In one example, the AAV genome comprises a plurality of polynucleotide sequences, said plurality encoding two or more of a proteins of interest, an RNAi agent, and/or a marker protein, as described herein.

The AAV described herein which comprises a modified VP1 sequence will have improved functionality when produced in an insect cell relative to an AAV comprising the corresponding wildtype VP1 sequence.

In one example, the AAV comprising the capsid protein with the modified VP1 sequence is produced using a method of the disclosure.

Kits

The present disclosure also provides a nucleic acid molecule, baculovirus vector, plurality of baculovirus vectors and/or insect cell of the disclosure in the form of a kit. The kit may comprise a container comprising a nucleic acid molecule of the disclosure. In one example, the nucleic acid is comprised within a baculovirus vector. In one example, the kit comprises a first container comprising a nucleic acid molecule of the disclosure and a second container comprising one or more further reagents for producing an AAV. In one example, the nucleic acid is comprised within a baculovirus vector. In one example, the kit comprises the plurality of baculovirus vectors of the disclosure, each comprised within a separate container. The kit may optionally further comprise an insect cell e.g., suitable for production of an AAV in accordance with the present disclosure. The kit may also further comprise instructions for use of the nucleic acid molecule, baculovirus vector, plurality of baculovirus vectors and/or insect cell of the disclosure for production of an AAV using a method as described herein.

EXPERIMENTAL EXAMPLES

Example 1

Design, Production and Testing of Modified AAV VP1 Sequences

In this example, the inventors designed and prepared AAVs having a viral capsid protein subunit 1 (VP1) into which specific sequence modification i.e., amino acid substitutions, were introduced to the phospholipase A2 (PLA2) domain and flanking sequence to restore phospholipase activity and viral functionality of AAVs when produced in insect cells. Further, based on a multiple sequence alignment performed for VP1 subsequences comprising the PLA2 domain and flanking sequences for various representative AAV serotypes, a consensus VP1 subsequence comprising the PLA2 domain and flanking sequence was prepared including the sequence modifications designed to restore phospholipase activity. This consensus VP1 subsequence is set forth in SEQ ID NO: 1.

1.1 Design of Modified AAV8 VP1 and AAV9 VP1 Sequences

Pairwise sequence alignments were performed using the BLASTp alignment tool for the N-terminal 180 amino acids from the viral capsid protein 1 (VP1) protein of AAV8 (SEQ ID NO: 34) and AAV2 (SEQ ID NO: 28), and for the N-terminal 180 amino acids from the VP1 protein of AAV9 (SEQ ID NO: 35) and AAV2 (SEQ ID NO: 26). Based on these alignments, the PLA2 domain and flanking sequences from AAV8 and AAV9 were shown to be highly conserved to the corresponding sequence in AAV2.

Based on these sequence alignments, a modified AAV8 VP1 sequence was designed in silico by substituting amino acids at positions 42, 67, 81, 84, 85 and 105 of the sequence set forth in SEQ ID NO: 34 with the amino acids which occur at the corresponding positions in the AAV2 VP1 sequence set forth in SEQ ID NO 28 i.e., G42S, A67E, Q81R, Q84D, A85S and Q105K within the sequence of SEQ ID NO: 34. Two of the residue positions substituted in the modified AAV8 VP1 sequence were in the region flanking the PLA2 domain (but considered likely to be involved in folding and/or activity of the PLA2 domain), and four of the residue positions modified resided within the PLA2 domain itself.

Similarly, a modified AAV9 VP1 sequence was designed in silico by substituting the amino acids at positions 42, 67, 81, 84 and 85 of the sequence set forth in SEQ ID NO: 35 with the amino acids which occur at the corresponding positions in the AAV2 VP1 sequence set forth in SEQ ID NO 28 i.e., A42S, A67E, Q81R, K84D and A85S within the sequence of SEQ ID NO: 35. One of the positions substituted in the modified AAV9 VP1 sequence was in the region flanking the PLA2 domain (but considered likely to be involved in folding and/or activity of the PLA2 domain), and four of the residue positions modified resided within the PLA2 domain itself.

1.2 Design of a Consensus AAV VP1 Subsequence Including Modified Residues

Based on the sequence alignments performed for complete VP1 sequences for AAV2, AAV8 and AAV9, a multiple sequence alignment was performed for VP1 subsequences comprising the PLA2 domain and flanking sequences for AAV serotypes 1-13 (SEQ ID NOs: 15-26). In addition to those differences identified from the pairwise alignments above, a number of further non-identical residues were identified within the subsequences. However, it was decided not to mutate these positions for identity for the corresponding AAV2 sequence, either because the differences were deemed to be conservative differences and/or because the residues positions were outside of the PLA2 domain and considered unlikely to impact phospholipase activity. Based on the multiple sequence alignment, a consensus VP1 subsequence comprising the PLA2 domain and flanking sequence with the amino acid substitutions described above was prepared in silico (SEQ ID NO: 1).

1.3 Production of a Baculovirus Vector Expressing Structural and Non-Structural AAV8 Proteins A baculovirus vector encoding the modified AAV8 capsid protein comprising subunits VP1, VP2 and VP3 and AAV8 non-structural proteins Rep78 and Rep52 was prepared (BacAAV8-Rep-VPmod, FIG. 1).

Figure 2:
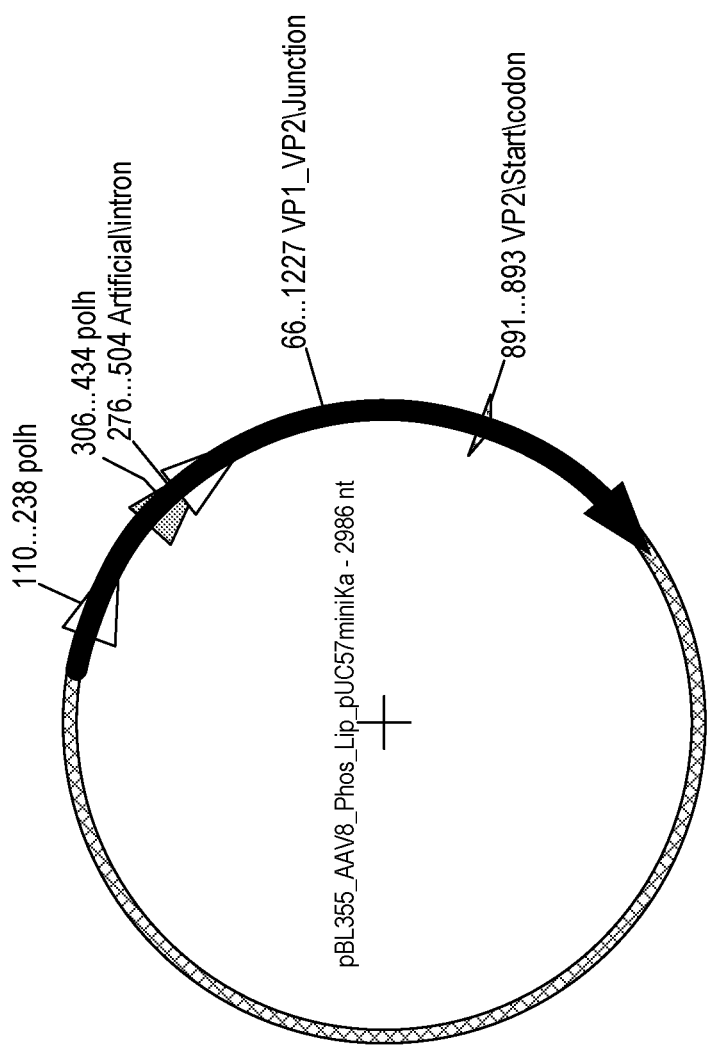
FIG. 2 is a vector map for the DNA construct designated AAV8-VPmod. This DNA construct contains a modified version of the AAV8 capsid gene which was used to prepare AAV8-Rep-VPmod (FIG. 4) and BacAAV8-Rep-VPmod (FIG. 1).
Figure 3:
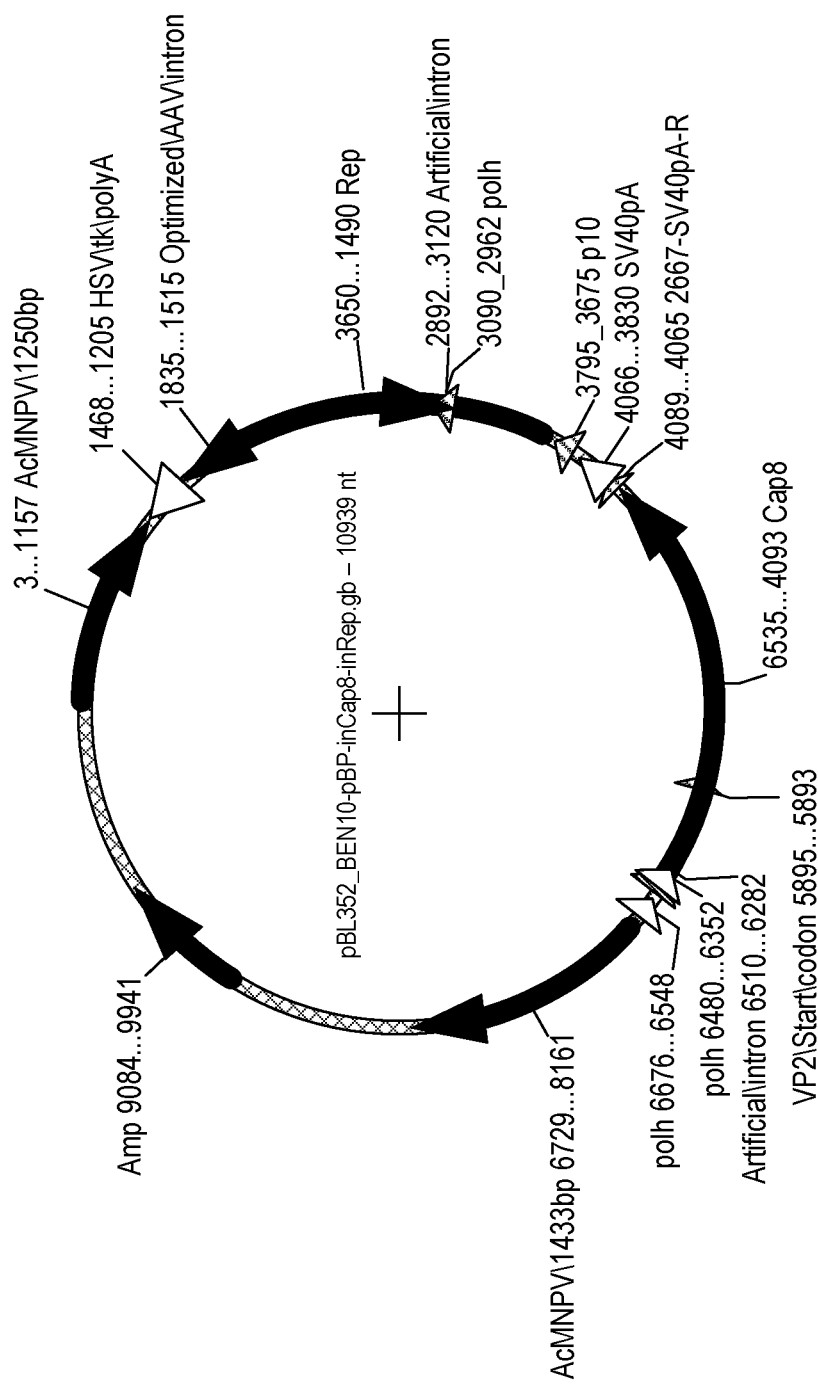
FIG. 3 is a vector map for the DNA construct designated wtAAV8-Rep/Cap. This DNA construct was designed to express AAV Rep proteins and a wt AAV8 capsid in insect cells and was used to prepare AAV containing the wtAAV8 capsid protein.
Figure 4:
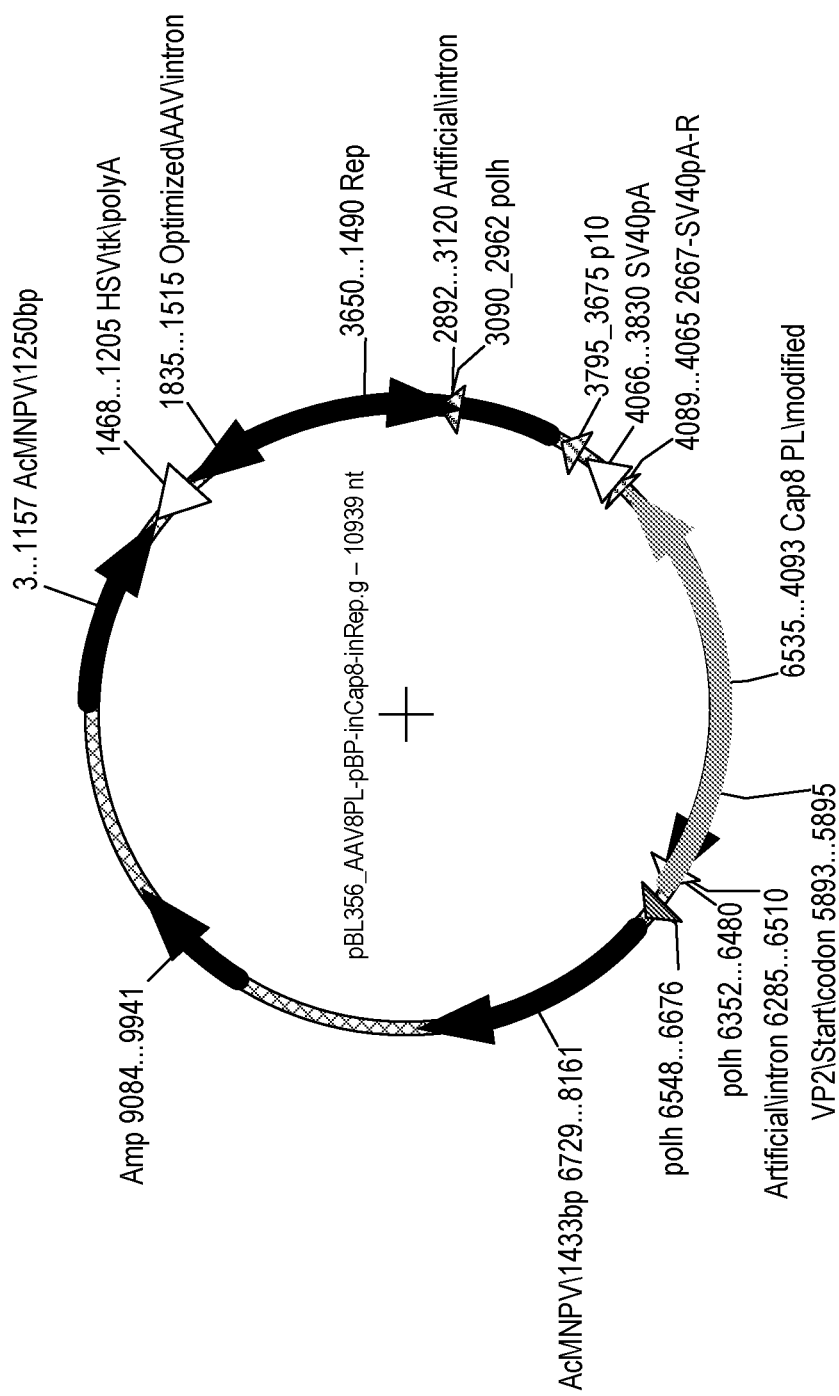
FIG. 4 is a vector map for the DNA construct designated AAV8-Rep-VPmod. This DNA construct was designed to express AAV Rep proteins and a modified AAV8 capsid in insect cells and was used to prepare BacAAV8-Rep-VPmod (FIG. 1).

Briefly, a DNA construct encoding the AAV8 capsid protein (VP1, VP2 and Vp3) with a modified VP1 subunit comprising the sequence set forth in SEQ ID NO: 21, and having flanking NotI and ApaI restriction sites, was synthesized at GenScript (AAV8-VPmod, FIG. 2). A wtAAV8-Rep/Cap plasmid (Virovek, Hayward, Calif.) encoding the non-structural proteins Rep78, Rep68, Rep52 and Rep40 as well as the Capsid Proteins VP1, VP2 and VP3 and the Assembly-Activating Protein (AAP) was used as a backbone to accept the AAV8-VPmod DNA construct. Both the AAV8-VPmod DNA construct and wtAAV8-Rep/Cap plasmid were digested with NotI and ApaI, after which the AAV8-VPmod DNA construct was then ligated into the wtAAV8-Rep/Cap plasmid backbone (FIG. 3) in place of the wt capsid protein encoding sequence to yield AAV8-Rep-VPmod (FIG. 4).

The AAV8-Rep-VPmod intermediate was then cloned into the pOET1 baculovirus transfer vector (Oxford Expression Technologies). To facilitate this, an EcoRV site was inserted into AAV8-Rep-VPmod intermediate using the Quickchange technique to yield the AAV8-Rep-VPmod-EcoRV intermediate. The AAV8-Rep-VPmod-EcoRV intermediate and pOET1 were then digested with NotI and EcoRV and the insert was then ligated into the pOET1 backbone (Oxford Expression Technologies) generating the final AAV8-Rep-VPmod clone (BacAAV8-Rep-VPmod, FIG. 1).

Figure 5:
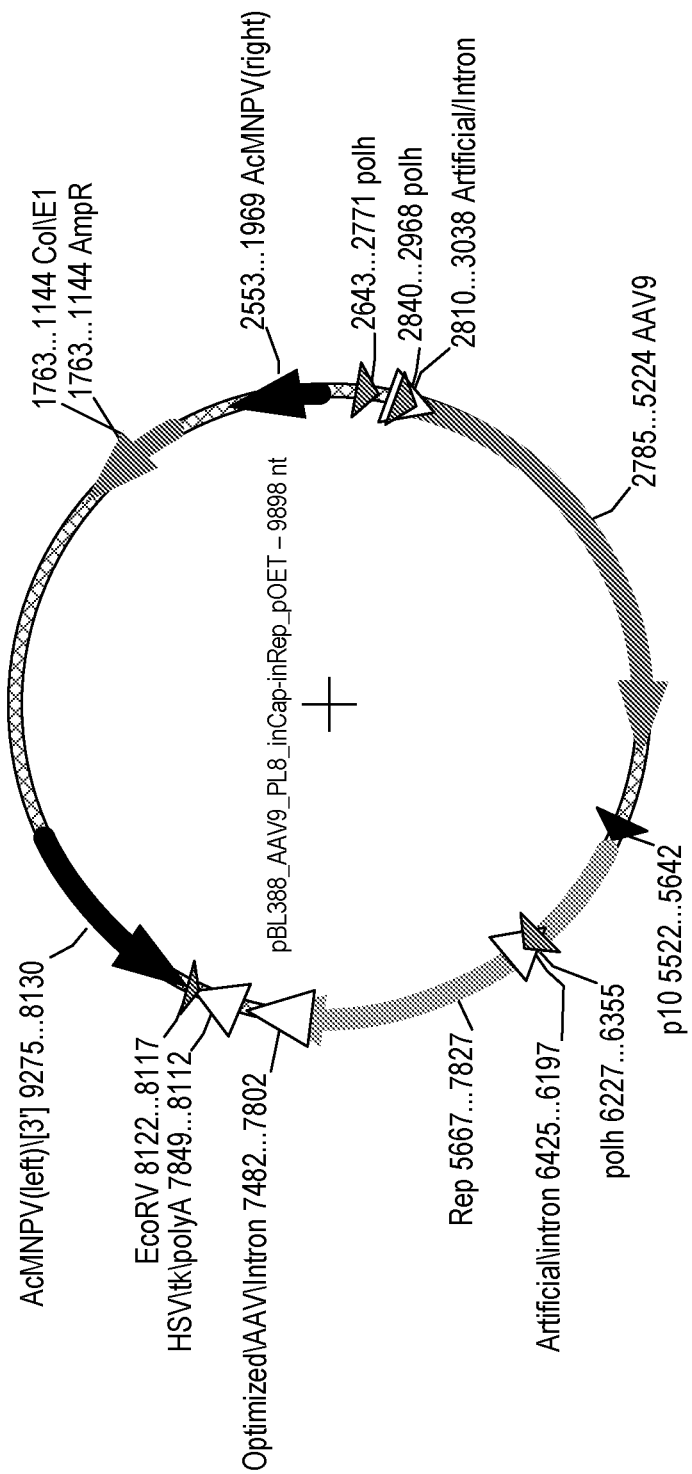
FIG. 5 is a vector map for the DNA construct designated BacAAV9-Rep-VPmod. This DNA construct was designed to express AAV Rep proteins and the modified AAV9 capsid in insect cells. The vector backbone was a baculovirus vector pOET1 backbone (Oxford Expression Technologies) and was used to prepare AAV containing the modified AAV9 capsid protein.

1.4 Production of a Baculovirus Vector Expressing Structural and Non-Structural AAV9 Proteins A baculovirus vector encoding the AAV9 capsid protein comprising subunits VP1, VP2 and VP3 and AAV9 non-structural proteins Rep78, Rep 68, Rep 52 and Rep40 was prepared (BacAAV9-Rep-VPmod, FIG. 5).

Figure 6:
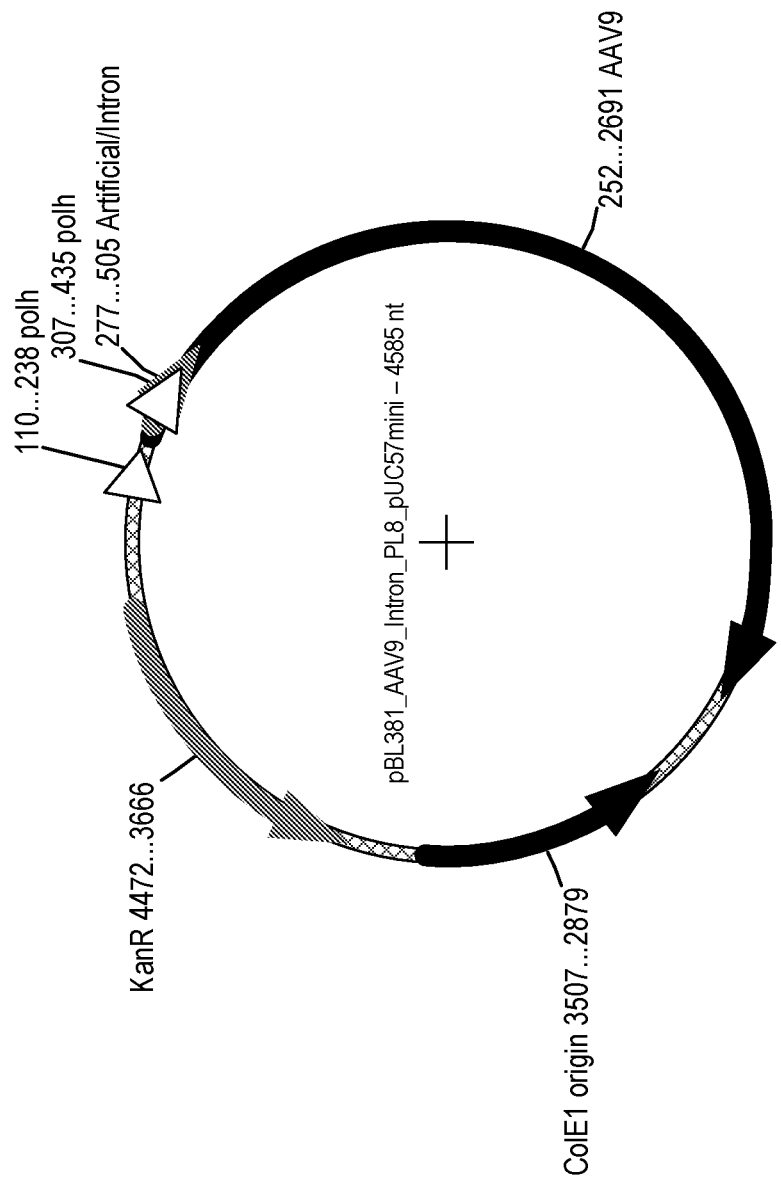
FIG. 6 is a vector map for the DNA construct designated AAV9-VPmod. This DNA construct contains a modified version of the AAV9 capsid gene which was used to prepare BacAAV9-Rep-VPmod (FIG. 5).
Figure 7:
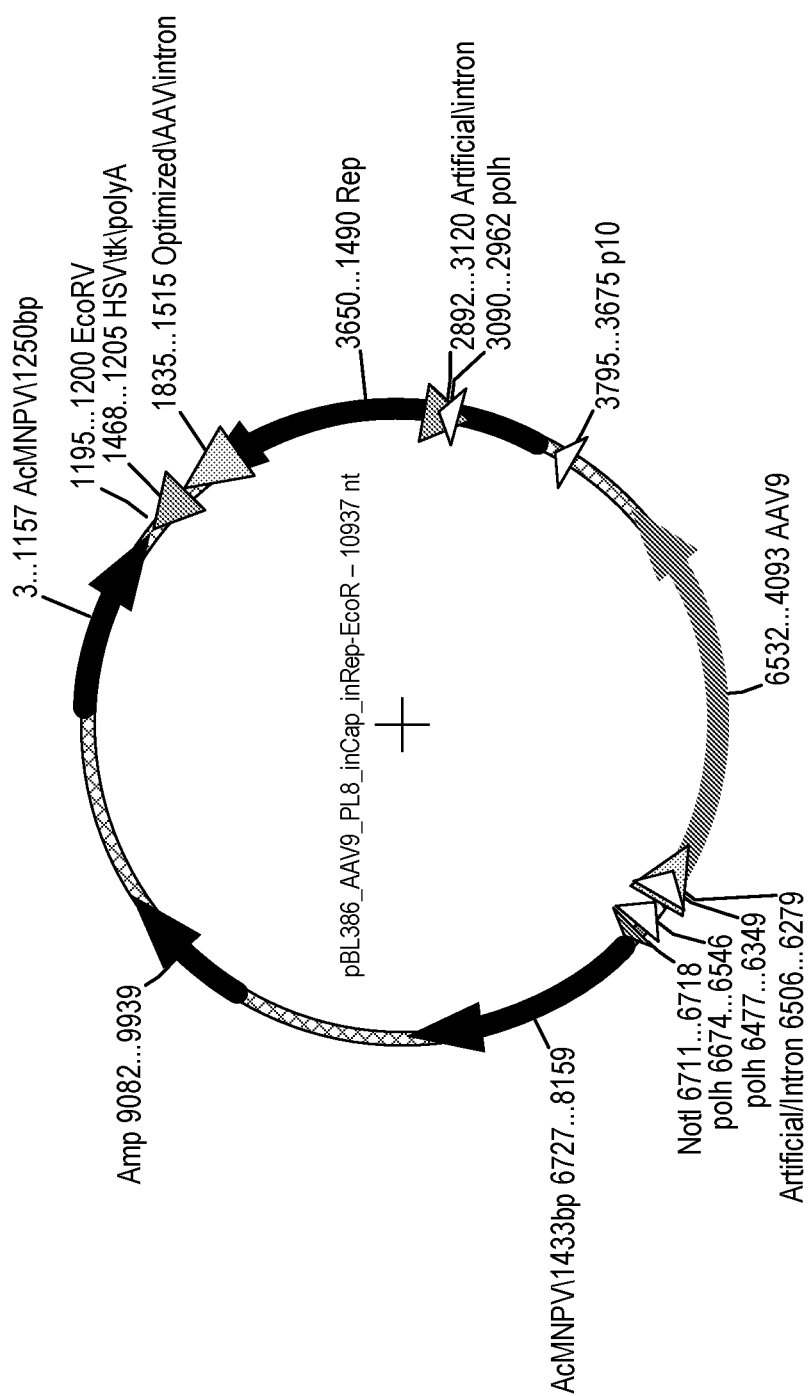
FIG. 7 is a vector map for the DNA construct designated AAV9-Rep-VPmod. This DNA construct was designed to express AAV Rep proteins and a modified AAV9 capsid in insect cells.

Briefly, a DNA construct encoding the AAV9 capsid protein with a modified AAV9 VP1 subunit encoded by the sequence set forth in SEQ ID NO: 22, and having flanking NotI and ApaI restriction sites, was synthesized at GenScript (AAV9-VPmod, FIG. 6). A wtAAV9-Rep plasmid (Virovek, Hayward, Calif.) encoding the non-structural proteins Rep78, Rep68, Rep 52 and Rep40 as well as the Capsid Proteins VP1, VP2 and VP3 and the Assembly-Activating Protein (AAP) was used as a backbone to accept the AAV9-VPmod DNA construct. Both the AAV9-VPmod DNA construct and wtAAV9-Rep plasmid were digested with NotI and ApaI, after which the AAV9-VPmod DNA construct was then ligated into the wtAAV9-Rep plasmid backbone (FIG. 3) in place of the wt capsid protein encoding sequence to yield AAV9-Rep-VPmod (FIG. 7).

The AAV9-Rep-VPmod intermediate was then cloned into the pOET1 baculovirus transfer vector (Oxford Expression Technologies). To facilitate this, an EcoRV site was inserted into AAV9-Rep-VPmod intermediate using the Quickchange technique to yield the AAV9-Rep-VPmod-EcoRV intermediate. The AAV9-Rep-VPmod-EcoRV intermediate and pOET1 (Oxford Expression Technologies) were then digested with NotI and EcoRV and the insert was then ligated into the pOET1 backbone generating the final AAV9-Rep-VPmod clone (BacAAV9-Rep-CapPL, FIG. 5).

1.5 Production of Baculovirus Vectors Expressing Gene of Interest (GOI)

Figure 8:
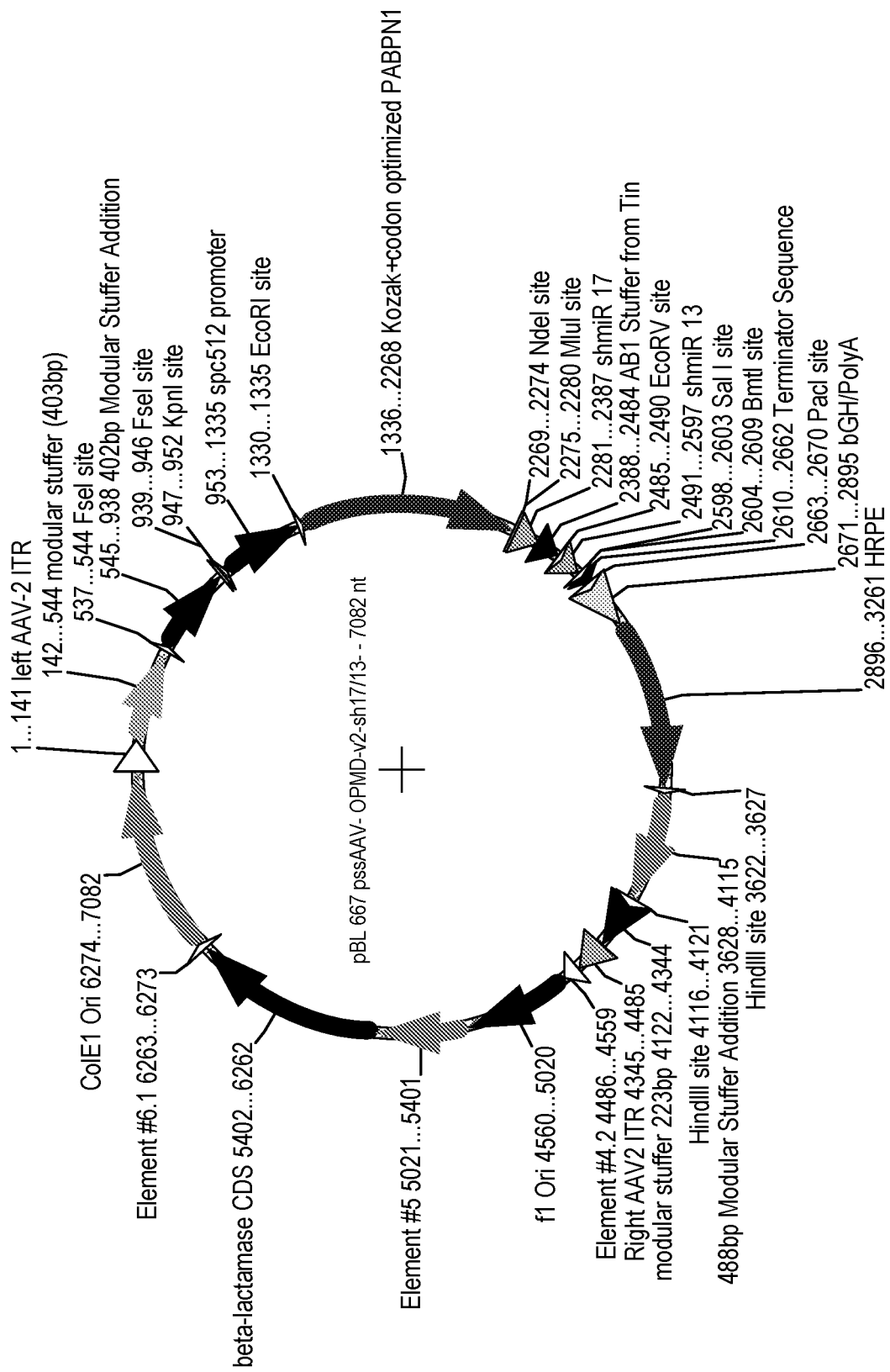
FIG. 8 is a vector map for the DNA construct designated AAV2-GOI. This DNA construct was designed to express two shmiRs flanked by AAV ITRs and was used to prepare BacAAV2-GOI (FIG. 9).
Figure 9:
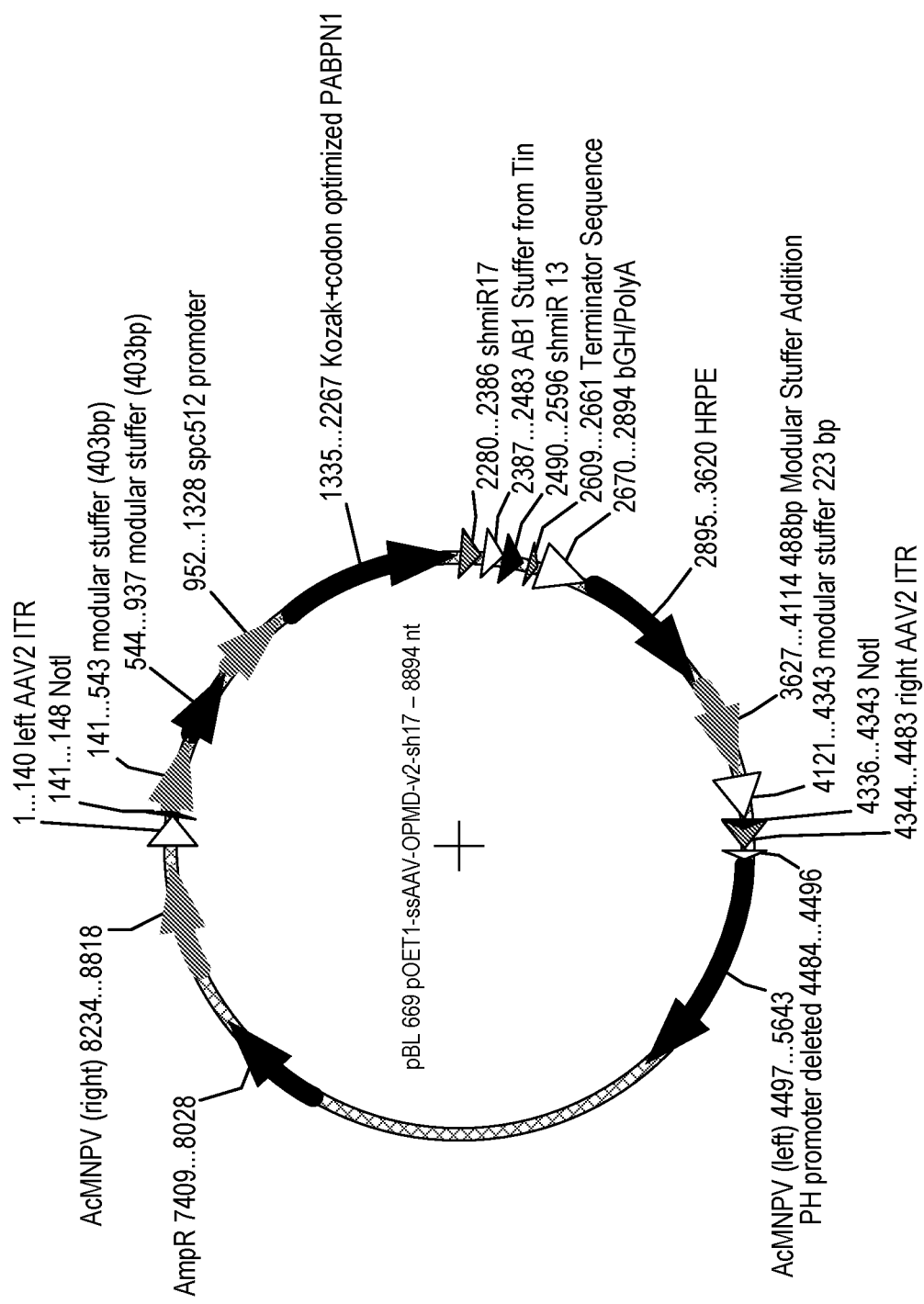
FIG. 9 is a vector map for the DNA construct designated BacAAV2-GOI. This DNA construct was designed to express two shmiRs flanked by AAV ITRs (AAV2-GOI) in the baculovirus vector pOET1 backbone (Oxford Expression Technologies). This construct was used to prepare AAV containing the modified AAV9 capsid protein expressing a GOI encoding two shmiRs.

Baculovirus vectors encoding a gene of interest (GOI) flanked by AAV2 Inverted Terminal Repeats (ITRs) were prepared. Briefly, in one instance a DNA construct encoding two shmiRs targeting a transcript of human PABPN1 flanked by AAV2 ITRs was cloned into the pOET1 baculovirus transfer vector (Oxford Expression Technologies) by digesting the AAV2-GOI construct (FIG. 8) and pOET1 (Oxford Expression Technologies) with NotI, and ligating the AAV2-GOI construct into the pOET1 backbone to generate the final clone (BacAAV2-GOI, FIG. 9). A second GOI was also prepared in an identical fashion to that described above, albeit encoding for three shmiRs targeting various regions of the HBV polymerase gene transcript.

1.6 Generation of P0 Baculovirus Stock

Baculovirus P0 stocks were generated using the Oxford Expression Technologies baculoCOMPLETE system (according to manufacturer's instructions). Briefly, 1 million Sf9 cells were seeded in a 6 well plate 1 hour prior to transfection and allowed to adhere to the plate. In 1 ml of TC100 medium, 500 ng of Bac-AAV2-GOI plasmids, BacAAV8-Rep-CapPL or BacAAV9-Rep-CapPL were mixed with 500 ng flash BAC DNA and baculoFECTIN transfection reagent (according to manufacturer's protocol). Following a 30-minute incubation at room temperature, the transfection mixture was added to the seeded Sf9 cells. The 6 well plate was incubated at 28° C. At 24 hours post transfection, 1 ml of Sf9 media was added to the cells. At 5 days post transfection, the media containing the P0 baculovirus stock was collected and stored at 4° C. P0 baculovirus were thus produced for BacAAV8-Rep-CapPL, BacAAV9-Rep-CapPL and Bac-AAV2-GOI.

1.7 Generation of P1 Baculovirus Stock 500 ul of P0 Baculovirus stock was used to infect 100 ml of Sf9 cell culture at a concentration of 2×10e6 cells/ml. The baculovirus culture was incubated at 28° C. with shaking at 140 rpm for 5 days. At 5 days post infection, the media containing the P1 was harvested and stored at 4° C.

1.8 Generation of P2 Baculovirus Stock 500 ul of P1 Baculovirus stock was used to infect 100 ml of Sf9 cell culture at a concentration of 2×10e6 cells/ml. The baculovirus culture was incubated at 28° C. with shaking at 140 rpm for 5 days. At 5 days post infection, the media containing the P2 was harvested and stored at 4° C.

1.9 Titering P2 Baculovirus Stock

The titer of baculovirus P2 stocks was determined using Oxford Expression Technologies baculoQUANT kit. Baculovirus stocks were serially diluted and lysed with the provided lysis buffer according to manufacturer's instructions. DNA was amplified using qPCR for baculovirus envelope fusion protein, gp64. P2 stocks were quantified using a standard curve and extrapolated to determine the viral pfu/ml.

1.10 Co-Infection to Produce AAV 600 ml of Sf9 cells at a cell density of 2×10e6 cells/ml were co-infected with BacAAV8-Rep-CapPL and BacAAV2-GOI (encoding 3 shmiRs targeting HBV polymerase gene transcript) at an MOI of 0.1, or BacAAV9-Rep-CapPL and BacAAV2-GOI (encoding 2 shmiRs targeting human PABPN1 gene transcript) at an MOI of 0.1. The cell culture was then incubated at 28° C. with shaking at 115 rpm for 6 days.

1.11 Purification of AAV

Six days post-infection, clarified media was collected from the infected cultures. Baculovirus were filtered away from the AAV using 0.2 micron filtering, followed by 0.1 micron filtering. PEG was then added to the baculovirus free media to precipitate the AAV. 24 hours post PEG addition the media was spun at 2500 g for 45 minutes to pellet the AAV. The supernatant was discarded and the pelleted virus was suspended in lysis buffer. Initial purification of the AAV was performed by an iodixanol gradient, from which the 5 ml layer between the 40-60% fraction was collected. This virus containing layer was buffer exchanged to remove the residual iodixanol and the buffer exchanged virus was layered onto a cesium gradient. Overnight centrifugation was then performed on the cesium gradient. AAV containing bands from the cesium gradient were collected with syringes and buffer exchanged to remove the cesium chloride from the purified AAV virus stock.

1.12 Titering AAV

The final AAV titers for all AAV preparations were quantified by qPCR. Briefly, ten microliters of purified AAV virus was DNAse treated (DNAseI, Amplification Grade, 1U/ul, Invitrogen) for 15 minutes at room temperature. The DNAse enzyme was then deactivated by incubation at 65° C. for 10 minutes. The virus was diluted as follows: 1:10; 1:30; 1:100; 1:1,000; 1:3,000; 1:10,000. Each dilution was analyzed by qPCR to determine the total number of viral genomes per ml.

1.13 AAV Prepared in Mammalian Cells

The functionality of AAV prepared in mammalian cells was compared to AAV prepared in insect cells as described above. To compare the biological activity (functionality) of the recombinant AAV prepared in mammalian and insect cells, mammalian cells were infected in vitro with various titres of viruses and expression of processed shmiRs quantified using qRT PCR assays.

For these experiments, recombinant AAV8 particles expressing 3 shmiRs targeting HBV polymerase gene transcripts were prepared in mammalian cells by a commercial supplier (Vector Biolabs; https://www.vectorbiolabs.com). Furthermore, recombinant AAV9 particles expressing 2 shmiRs targeting human PABPN1 were prepared by a second supplier in mammalian cells, namely Nationwide Children's hospital vector core (https://www.nationwidechildrens.org/research/resources-infrastructure/core-facilities/viral-vector-core-clinical-manufacturing-facility).

The biological activity was assessed for (i) AAV8 with unmodified VP1 produced in mammalian cells (Vector Biolabs), (ii) AAV8 with modified VP1 (as described herein using BacAAV8-Rep-VPmod) produced by baculovirus in insect cells, and (iii) AAV8 with unmodified wt VP1 produced by baculovirus in insect cells using wtAAV8-Rep/Cap, (Ben10, Virovek, Hayward, Calif.), each encoding the 3 shmiRs targeting HBV polymerase gene (shmiR1, shmiR2 and shmiR3). Briefly, JHU67 cells were infected with the modified or non-modified recombinant viral preparations described above at MOIs of 4×10e9, 8×10e9 and 1.6×10e10, and shmiR expression quantified for each of the three shmiRs 72 hrs after infection. To quantify expression of shmiRs, RNA was extracted from the infected cells using the Qiagen RNA mini kit (Qiagen). RNA was reverse transcribed using the Qiagen miScript kit (Qiagen). The cDNA was then used in a qPCR reaction with specific primers designed to amplify the shmiR targets to determine the total number of copies present in the sample.

Figure 10B:
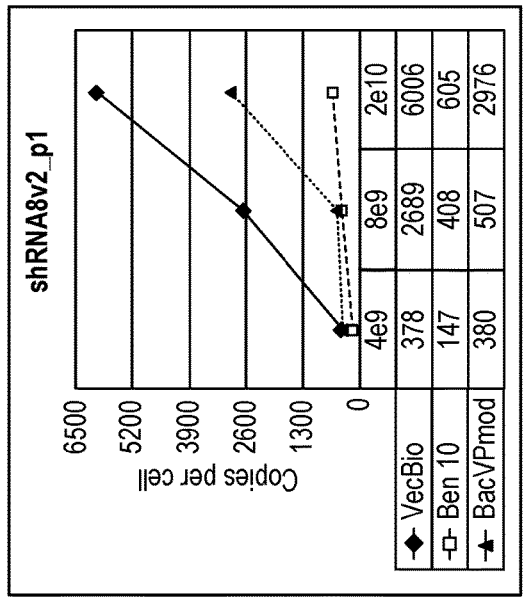
FIGS. 10A-10C show the total number of shmiR copies expressed per cell from JHU67 cells infected with 4×10e9, 8×10e9 and 1.6×10e10 AAV vector genomes of (i) AAV8 with unmodified VP1 produced in mammalian cells (VecBio), (ii) AAV8 with modified VP1 produced by baculovirus in insect cells (BacVPmod), and (iii) AAV8 with unmodified VP1 produced by baculovirus in insect cells (Ben10). AAV having the wildtype capsid produced in mammalian cells express high levels of shmiRs compared to AAV having the wildtype capsid produced in insect cells, where expression is nearly undetectable. AAV having the capsid with the modified VP1 produced in insect cells show a marked increase in expression, and therefore functionality, compared to AAV produced in insect using the unmodified wildtype capsid.
Figure 10C:
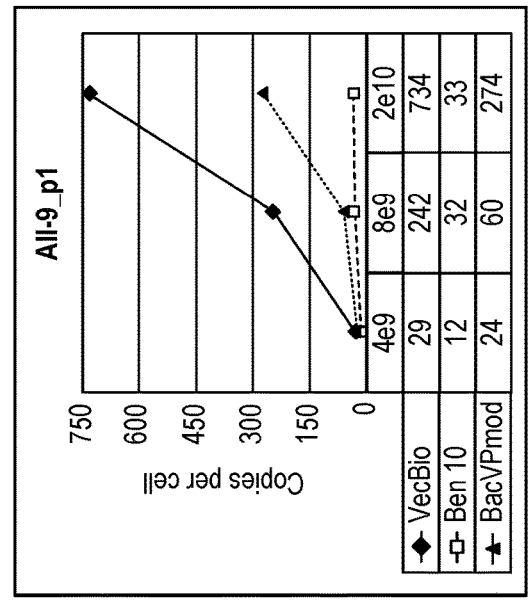
Figure 10A:
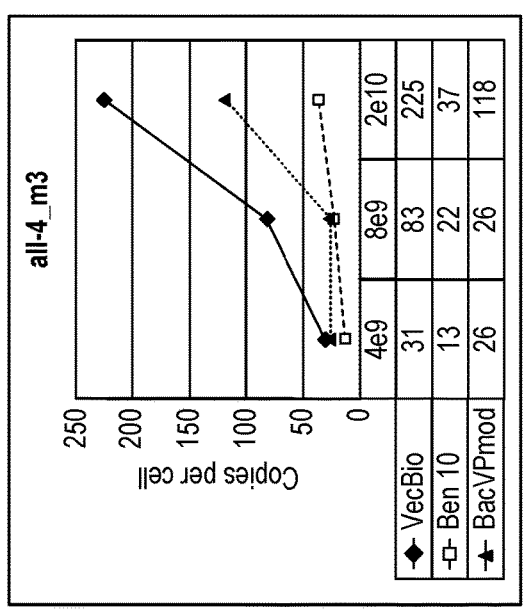

As shown in FIGS. 10A-10C, cells infected with AAV8 with unmodified wt VP1 prepared in mammalian cells produced readily detectable levels of shmiRs, whilst AAV8 with unmodified wt VP1 produced by baculovirus in insect cells produced little, if any, shmiRs. In contrast AAV8 with modified VP1 produced by baculovirus in insect cells produced relatively high levels of shmiRs, indicating an increase in functionality of these AAVs as compare to the AAV8 with unmodified wt VP1 produced by baculovirus in insect cells.

The biological activity was also assessed for (i) AAV9 with unmodified capsid protein produced in mammalian cells (Nationwide), and (ii) AAV9 with modified capsid protein using BACAAV9-Rep-VPmod (as described herein) produced by baculovirus in insect cells, each encoding 2 shmiRs targeting transcripts of human PABPN1 (designated sh13 and sh17). Briefly, C2C12 cells expressing the AAV internalization receptor were infected with 4×10e9, 8×10e9 and 1.6×10e10 vector genomes. Following a 72-hour incubation, cells were harvested, RNA extracted and shmiR expression quantified for the two shmiRs in accordance with the qPCR method described above.

Figure 11:
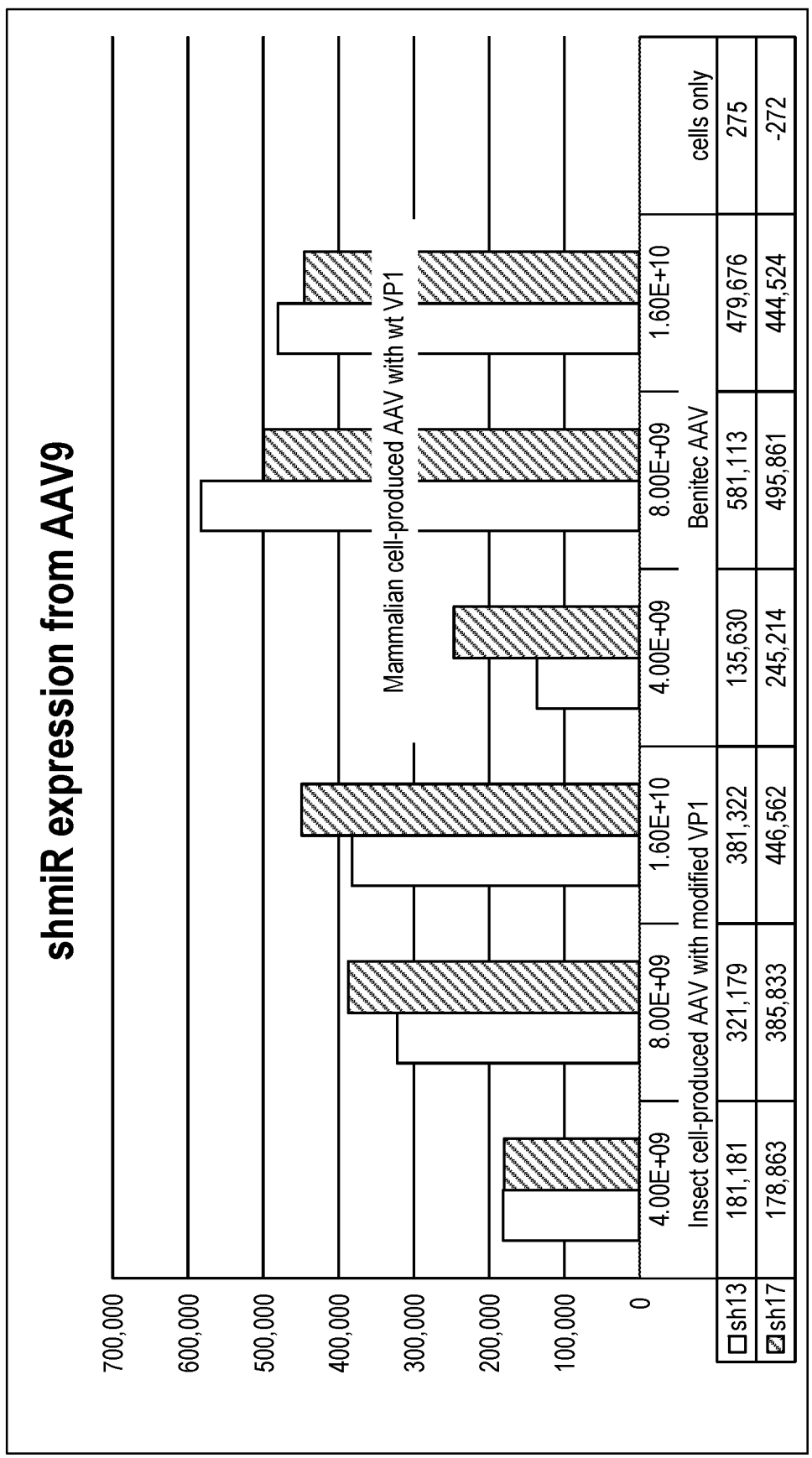
FIG. 11 shows the total number of shmiR copies expressed from C2C12 cells expressing the AAV Internalization Receptor (AAV-R) and infected with 4×10e9, 8×10e9 and 1.6×10e10 AAV vector genomes of (i) AAV9 with unmodified VP1 produced in mammalian cells, and (ii) AAV9 with modified VP1 produced by baculovirus in insect cells. Both recombinant viruses produced equivalent levels of shmiR, demonstrating equivalent functionality.

As shown in FIG. 11, the two preparations showed very similar levels of shmiR expression, indicating very similar viral functionality.

Although demonstrated in the context of AAV from serotypes 8 and 9, it is contemplated that modifying the VP1 subunit sequence of other AAV serotypes (other than serotype 2) in accordance with the approach described herein will restore functionality of AAV when produced from a baculovirus expression system in insect cells.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

We claim:

1. A nucleic acid molecule comprising a polynucleotide sequence encoding an adeno-associated virus (AAV) viral capsid protein, wherein the viral capsid protein comprises a modified subunit 1 (VP1) sequence comprising a serine at position 1, a glutamic acid at position 26, an arginine at position 40, an aspartic acid at position 43, a serine at position 44 and a lysine at position 64, wherein the amino acid positions are defined relative to the sequence set forth in SEQ ID NO: 1, wherein the amino acids at any one or more of positions 1, 26, 40, 43, 44 and 64 are modified relative to a corresponding wildtype sequence, and wherein no additional amino acids other than those at said any one or more positions 1, 26, 40, 43, 44 and 64 are modified relative to the corresponding wildtype sequence.

2. The nucleic acid molecule according to claim 1, wherein the viral capsid protein is selected from the group consisting of:
   a viral capsid protein from AAV1 wherein the modified VP1 sequence comprises the sequence set forth in SEQ ID NO: 15;
   (ii) a viral capsid protein from AAV3 wherein the modified VP1 sequence comprises the sequence set forth in SEQ ID NO: 16;
   (iii) a viral capsid protein from AAV4 wherein the modified VP1 sequence comprises the sequence set forth in SEQ ID NO: 17;
   (iv) a viral capsid protein from AAV5 wherein the modified VP1 sequence comprises the sequence set forth in SEQ ID NO: 18;
   (v) a viral capsid protein from AAV6 wherein the modified VP1 sequence comprises the sequence set forth in SEQ ID NO: 19;
   (vi) a viral capsid protein from AAV7 wherein the modified VP1 sequence comprises the sequence set forth in SEQ ID NO: 20;
   (vii) a viral capsid protein from AAV8 wherein the modified VP1 sequence comprises the sequence set forth in SEQ ID NO: 21;
   (viii) a viral capsid protein from AAV9 wherein the modified VP1 sequence comprises the sequence set forth in SEQ ID NO: 22;
   (ix) a viral capsid protein from AAV10 wherein the modified VP1 sequence comprises the sequence set forth in SEQ ID NO: 23;
   (x) a viral capsid protein from AAV11 wherein the modified VP1 sequence comprises the sequence set forth in SEQ ID NO: 24;
   (xi) a viral capsid protein from AAV12 wherein the modified VP1 sequence comprises the sequence set forth in SEQ ID NO: 25; and
   (xii) a viral capsid protein from AAV13 wherein the modified VP1 sequence comprises the sequence set forth in SEQ ID NO: 26.

3. The nucleic acid molecule according to claim 1, wherein the viral capsid protein is from AAV8 and the modified VP1 sequence comprises the sequence set forth in SEQ ID NO: 21.

4. The nucleic acid molecule according to claim 1, wherein the viral capsid protein is from AAV9 and the modified VP1 sequence comprises the sequence set forth in SEQ ID NO: 22.

5. The nucleic acid molecule according to claim 1 4, wherein the viral capsid protein comprises subunit 2 (VP2) and subunit 3 (VP3) sequences from the same AAV serotype as the modified VP1.

6. The nucleic acid molecule according to claim 1, wherein:
the nucleotide sequence encoding the AAV viral capsid protein is operably-linked to a promoter for expression in an insect cell; and/or
the nucleotide sequence encoding the AAV viral capsid protein is operably-linked to a polyhedron promoter or a p10 promoter.

7. The nucleic acid molecule according to claim 1, comprising a polynucleotide sequence encoding at least one large AAV replication (Rep) protein selected from Rep78 and Rep68 and at least one small AAV Rep protein selected from Rep52 and Rep40, optionally wherein:
the polynucleotide sequence encoding the Rep proteins is operably-linked to a promoter for expression of the Rep proteins in an insect cell; or
the polynucleotide sequence encoding the Rep proteins is operably-linked to a polyhedron promoter or a p10 promoter.

8. A baculovirus vector comprising the nucleic acid molecule of claim 1.

9. A plurality of baculovirus vectors comprising:
(a) (i) a first baculovirus vector comprising the nucleic acid molecule of claim 1 and a polynucleotide sequence encoding at least one large AAV replication (Rep) protein selected from Rep78 and Rep68 and at least one small AAV Rep protein selected from Rep52 and Rep40; and
(ii) a second baculovirus vector comprising a polynucleotide encoding a protein or RNA of interest flanked by AAV inverted terminal repeat (ITR) sequences; or
(b) (i) a first baculovirus vector comprising the nucleic acid molecule of claim 1;
(ii) second baculovirus vector comprising a polynucleotide sequence encoding at least one large AAV replication (Rep) protein selected from Rep78 and Rep68 and at least one small AAV Rep protein selected from Rep52 and Rep40; and
(iii) a third baculovirus vector comprising a polynucleotide encoding a protein or RNA of interest flanked by AAV inverted terminal repeat (ITR) sequences.

10. The plurality of baculovirus vectors according to claim 9, wherein the second baculovirus vector comprises a polynucleotide sequence encoding Rep78 and Rep52.

11. The plurality of baculovirus vectors according to claim 9, wherein the polynucleotide sequence encoding the Rep proteins is operably-linked to a promoter for expression of the Rep proteins in an insect cell.

12. An insect cell comprising the nucleic acid according to claim 1.

13. An insect cell comprising a baculovirus vector according to claim 8,
optionally wherein the polynucleotide sequence encoding the AAV viral capsid protein and the polynucleotide sequence encoding the Rep proteins are expressed from episomally replicating recombinant baculovirus genomes within the insect cell, and/or
optionally wherein a polynucleotide encoding a protein or RNA of interest flanked by AAV inverted terminal repeat (ITR) sequences is expressed from an episomally replicating recombinant baculovirus genome within the insect cell.

14. A method for producing adeno-associated virus (AAV) in an insect cell comprising:
(i) culturing the insect cell according to claim 12 in culture media under conditions sufficient for the cells to produce AAV; and optionally
(ii) recovering and/or purifying the AAV from the culture media and/or cells.

15. A method for producing adeno-associated virus (AAV) in an insect cell comprising:
(i) co-infecting an insect cell with a plurality of baculovirus vectors of claim 9;
(ii) culturing the insect cell infected with the baculoviruses at (i) in culture media under conditions sufficient for the cells to produce AAV; and optionally
(iii) recovering and/or purifying the AAV from the culture media and/or cells.

16. An adeno-associated virus (AAV) comprising a viral capsid protein comprising a modified subunit 1 (VP1) sequence comprising a serine at position 1, a glutamic acid at position 26, an arginine at position 40, an aspartic acid at position 43, a serine at position 44 and a lysine at position 64, wherein the amino acid positions are defined relative to the sequence set forth in SEQ ID NO: 1, wherein the amino acids at any one or more of positions 1, 26, 40, 43, 44 and 64 are modified relative to a corresponding wildtype sequence, and wherein no additional amino acids other than those at said any one or more positions 1, 26, 40, 43, 44 and 64 are modified relative to the corresponding wildtype sequence.

17. The AAV according to claim 16, wherein the AAV is selected from the group consisting of:
(i) an AAV serotype 1, wherein the modified VP1 sequence comprises the sequence set forth in SEQ ID NO: 15;
(ii) an AAV serotype 3, wherein the modified VP1 sequence comprises the sequence set forth in SEQ ID NO: 16;
(iii) an AAV serotype 4, wherein the modified VP1 sequence comprises the sequence set forth in SEQ ID NO: 17;
(iv) an AAV serotype 5, wherein the modified VP1 sequence comprises the sequence set forth in SEQ ID NO: 18;
(v) an AAV serotype 6, wherein the modified VP1 sequence comprises the sequence set forth in SEQ ID NO: 19;
(vi) an AAV serotype 7, wherein the modified VP1 sequence comprises the sequence set forth in SEQ ID NO: 20;
(vii) an AAV serotype 8, wherein the modified VP1 sequence comprises the sequence set forth in SEQ ID NO: 21;
(viii) an AAV serotype 9, wherein the modified VP1 sequence comprises the sequence set forth in SEQ ID NO: 22;
(ix) an AAV serotype 10, wherein the modified VP1 sequence comprises the sequence set forth in SEQ ID NO: 23;
(x) an AAV serotype 11, wherein the modified VP1 sequence comprises the sequence set forth in SEQ ID NO: 24;

(xi) an AAV serotype 12, wherein the modified VP1 sequence comprises the sequence set forth in SEQ ID NO: 25; and (xii) an AAV serotype 13, wherein the modified VP1 sequence comprises the sequence set forth in SEQ ID NO: 26.

18. A method of improving functionality of an adeno-associated virus (AAV) from a serotype other than serotype 2 which is produced in an insect cell, comprising modifying a viral capsid protein of the AAV relative to the corresponding wildtype sequence by substituting one or more amino acids at position 1, 26, 40, 43, 44 and 64 only, wherein the residue positions are determined relative to the sequence set forth in SEQ ID NO: 1, such that the viral capsid protein comprises a serine at position 1, a glutamic acid at position 26, an arginine at position 40, an aspartic acid at position 43, a serine at position 44 and a lysine at position 64, and wherein the AAV has improved functionality relative to the corresponding wildtype AAV which has not been modified and which is produced in insect cells.

19. The method according to claim 18 comprising modifying the viral capsid protein of the AAV relative to the corresponding wildtype sequence, such that:

(i) when the AAV is of serotype 1, the viral capsid protein includes a VP1 sequence comprising the sequence set forth in SEQ ID NO: 15;

(ii) when the AAV is of serotype 3, the viral capsid protein includes a VP1 sequence comprising the sequence set forth in SEQ ID NO: 16;

(iii) when the AAV is of serotype 4, the viral capsid protein includes a VP1 sequence comprising the sequence set forth in SEQ ID NO: 17;

(iv) when the AAV is of serotype 5, the viral capsid protein includes a VP1 sequence comprising the sequence set forth in SEQ ID NO: 18;

(v) when the AAV is of serotype 6, the viral capsid protein includes a VP1 sequence comprising the sequence set forth in SEQ ID NO: 19;

(vi) when the AAV is of serotype 7, the viral capsid protein includes a VP1 sequence comprising the sequence set forth in SEQ ID NO: 20;

(vii) when the AAV is of serotype 8, the viral capsid protein includes a VP1 sequence comprising the sequence set forth in SEQ ID NO: 21;

(viii) when the AAV is of serotype 9, the viral capsid protein includes a VP1 sequence comprising the sequence set forth in SEQ ID NO: 22;

(ix) when the AAV is of serotype 10, the viral capsid protein includes a VP1 sequence comprising the sequence set forth in SEQ ID NO: 23;

(x) when the AAV is of serotype 11, the viral capsid protein includes a VP1 sequence comprising the sequence set forth in SEQ ID NO: 24;

(xi) when the AAV is of serotype 12, the viral capsid protein includes a VP1 sequence comprising the sequence set forth in SEQ ID NO: 25; and (xii) when the AAV is of serotype 13, the viral capsid protein includes a VP1 sequence comprising the sequence set forth in SEQ ID NO: 26.

20. An insect cell comprising a plurality of baculovirus vectors according to claim 9, optionally wherein the polynucleotide sequence encoding the AAV viral capsid protein and the polynucleotide sequence encoding the Rep proteins are expressed from episomally replicating recombinant baculovirus genomes within the insect cell, and/or optionally wherein a polynucleotide encoding a protein or RNA of interest flanked by AAV inverted terminal repeat (ITR) sequences is expressed from an episomally replicating recombinant baculovirus genome within the insect cell.

* * * * *